United States Patent
Spiegel et al.

(10) Patent No.: US 9,745,334 B2
(45) Date of Patent: Aug. 29, 2017

(54) CYTOTOXIC-DRUG DELIVERING MOLECULES TARGETING HIV (CDM-HS), CYTOTOXIC ACTIVITY AGAINST THE HUMAN IMMUNODEFICIENCY VIRUS AND METHODS OF USE

(71) Applicant: YALE UNIVERSITY, New Haven, CT (US)

(72) Inventors: David Spiegel, New Haven, CT (US); Christopher Parker, Medina, OH (US)

(73) Assignee: YALE UNIVERSITY, New Haven, CT (US)

( * ) Notice: Subject to any disclaimer, the term of this patent is extended or adjusted under 35 U.S.C. 154(b) by 93 days.

(21) Appl. No.: 14/396,956

(22) PCT Filed: Mar. 15, 2013

(86) PCT No.: PCT/US2013/032044
§ 371 (c)(1),
(2) Date: Oct. 24, 2014

(87) PCT Pub. No.: WO2013/162757
PCT Pub. Date: Oct. 31, 2013

(65) Prior Publication Data
US 2015/0087609 A1   Mar. 26, 2015

Related U.S. Application Data

(60) Provisional application No. 61/638,569, filed on Apr. 26, 2012.

(51) Int. Cl.
| | | |
|---|---|---|
| *A01N 43/04* | (2006.01) | |
| *A61K 31/70* | (2006.01) | |
| *C07H 15/26* | (2006.01) | |
| *A61K 45/06* | (2006.01) | |
| *A61K 31/67* | (2006.01) | |
| *A61K 31/706* | (2006.01) | |
| *C07D 405/14* | (2006.01) | |
| *A61K 47/48* | (2006.01) | |
| *A61K 31/704* | (2006.01) | |
| *A61K 31/7028* | (2006.01) | |
| *A61K 31/7034* | (2006.01) | |

(52) U.S. Cl.
CPC ............ *C07H 15/26* (2013.01); *A61K 31/67* (2013.01); *A61K 31/706* (2013.01); *A61K 45/06* (2013.01); *A61K 47/481* (2013.01); *A61K 47/48215* (2013.01); *C07D 405/14* (2013.01); *A61K 31/704* (2013.01); *A61K 31/7028* (2013.01); *A61K 31/7034* (2013.01)

(58) Field of Classification Search
None
See application file for complete search history.

(56) References Cited

U.S. PATENT DOCUMENTS

| 8,852,630 B2 | 10/2014 | Spiegel et al. |
| 8,859,509 B2 | 10/2014 | Spiegel et al. |
| 9,296,708 B2 | 3/2016 | Spiegel et al. |
| 9,562,038 B2 | 2/2017 | Spiegel et al. |
| 2007/0243208 A1 | 10/2007 | Berger et al. |
| 2008/0103094 A1 | 5/2008 | Faulk et al. |
| 2011/0201563 A1 | 8/2011 | Spiegel et al. |

FOREIGN PATENT DOCUMENTS

| WO | 2009139863 A2 | 11/2009 | |
| WO | 2011046946 A2 | 4/2011 | |
| WO | WO 2011/046946 A2 * | 4/2011 | ............. A61K 39/42 |
| WO | 2012068366 A2 | 5/2012 | |

OTHER PUBLICATIONS

Newman et al. "Solid-state analysis of the active pharmaceutical ingredient in drug products", DDT (2003), vol. 8, pp. 898-905.*
Muro Journal of Controlled Release (2012), vol. 164, pp. 125-137.*
Parker, C.G. et al.; An Antibody-Recruiting Small Molecule that Targets HIV gp120. J. Am. Chem. Soc. 2009, vol. 131, pp. 16392-16394.
Wang J, et al. Modification and structure-activity relationship of a small molecule HIV-1 inhibitor targeting the viral envelope glycoprotein gp120. Organic & Biomolecular Chemistry, 2005;3(9):1781-1786.
Narumi T, et al. CD4 mimics targeting the HIV entry mechanism and their hybrid molecules with a CXCR4 antagonist. Bioorganic & Medicinal Chemistry Letters, 2010;20(19):5853-5858.
Johansson S, et al. Elimination of HIV-1 infection by treatment with a doxorubicin-conjugated anti-envelop antibody. AIDS, 2006;20(15):1911-1915.
Vever-Bizet C, et al. Targeting of HIV gp120 by oligonucleotide-photosensitizer conjugates—Light induced damages. FEBS Letters, 1999;467-471.
Griffiths GL, et al. Cure of SCID Mice Bearing Human B-Lymphoma Xenografts by an Anti-CD74 Antibody-Anthracycline Drug Conjugate. Clinical Cancer Research, 2003;9:6567-6571.
Pitts TW, et al. Soluble CD4-PE40 Is Cytotoxic for a Transfected Mammalian Cell Line Stably Expressing the Envelope Protein of Human Immunodeficiency Virus (HIV-1), and Cytotoxicity Is Variably Inhibited by the Sera of HIV-1-Infected Patients. AIDS Research and Human Retroviruses, 1991;7(9):741-750.
Reddy MM, et al. Identification of Candidate IgG Biomarkers for Alzheimer's Disease via Combinatorial Library Screening. Cell, 2011;144:132-142.

(Continued)

*Primary Examiner* — Patrick Lewis
(74) *Attorney, Agent, or Firm* — Henry D. Coleman; R. Neil Sudol

(57) ABSTRACT

The present invention is directed to new bifunctional compounds and methods for treating HIV infections. The bifunctional small molecules, generally referred to as CDM-Hs, function through orthogonal pathways, by inhibiting the gp120-CD4 interaction, and by introducing cytotoxic moieties to gp120-expressing cells, thereby causing cell death and preventing cell infection and spread of HIV. It is shown that CDM-Hs bind to gp120 and gp-120 expressing cells competitively with CD4, and these compounds cause cell death of HIV-infected cells, thereby decreasing viral infectivity. Compounds and methods are described herein.

47 Claims, 18 Drawing Sheets

(56) References Cited

OTHER PUBLICATIONS

Weber, et al. T Cell epitope: Friend or Foe? Immunogenicity of biologics, in context. Advanced Drug Delivery Reviews, 2009;61:965-976.
Volberding PA, Deeks SG. Antiretroviral therapy and management of HIV infection. Lancet, 2010;376:49-62.
Le Douce V, et al. Achieving a cure for HIV infection: do we have reasons to be optimistic? J Antimicrob Chemother, 2012;67:1063-1074.
Finzi D, et al. Identification of a Reservoir for HIV-1 in Patients on Highly Active Antiretroviral Therapy. Science, 1997;278:1295-1300.
Wong JK, et al. Recovery of Replication-Competent HIV Despite Prolonged Suppression of Plasma Viremia. Science, 1997;278:1291-1295.
Carter CC, et al. HIV-1 infects multipotent progenitor cells causing cell death and establishing latent cellular reservoirs. Nature Medicine, 2010;16(4):446-451.
Berger EA, Pastan I. Immunotoxin Complementation of HAART to Deplete Persisting HIV-Infected Cell Reservoirs. PLoS Pathogens, 2010;6(6):1-6.
Chaudhary VK, et al. Selective killing of HIV-infected cells by recombinant human CD4-Pseudomonas exotoxin hybrid protein. Nature, 1988;335:369-372.
Berger EA, et al. Recombinant CD4-Pseudomonas Exotoxin Hybrid Protein Displays HIV-Specific Cytotoxicity without Affecting MHC Class II-Dependent Functions. AIDS Research and Human Retroviruses, 1990;6(6):795-804.
Ashorn P, et al. Activity of CD4-Pseudomonas Exotoxin Against Cells Expressing Diverse Forms of the HIV and SIV Envelope Glycoproteins. Journal of Acquired Immune Deficiency Syndromes, 1992;5:70-77.
Bera TK, et al. Specific Killing of HIV-Infected Lymphocytes by a Recombinant Immunotoxin Directed against the HIV-1 Envelope Glycoprotein. Molecular Medicine, 1998;4:384-391.
Kennedy PE, et al. Primary HIV-1 Isolates Refractory to Neutralization by Soluble CD4 Are Potently Inhibited by CD4-Pseudomonas Exotoxin. Virology, 1993;192:375-379.
Berger EA, et al. Reconsidering targeted toxins to eliminate HIV infection: You gotta have HAART. Proc Natl Acad Sci USA, 1998;95:11511-11513.
Davey RT, et al. Use of Recombinant Soluble CD4 Pseudomonas Exotoxin, a Novel Immunotoxin, for Treatment of Persons Infected with Human Immunodeficiency Virus. The Journal of Infectious Diseases, 1994;178:1180-1188.
Lueders KK, et al. A Potent Anti-HIV Immunotoxin Blocks Spreading Infection by Primary HIV Type 1 Isolates in Multiple Cell Types. AIDS Research and Human Retroviruses, 2004;20(2):145-150.
Goldstein H, at al. Chimeric Toxins Targeted to the Human Immunodeficiency Virus Type 1 Envelope Glycoprotein Augment the in Vivo Activity of Combination Antiretroviral Therapy in thy/live-SCID-Hu Mice. The Journal of Infectious Diseases, 2000;181:921-926.
Johansson S, et al. Elimination of HIV-1 infection by treatment with a doxorubicin-conjugated anti-envelope antibody. AIDS, 2006;20:1911-1915.
Allen TM. Ligand-Targeted Therapeutics in Anticancer Therapy. Nature, 2002;2:750-763.
Hansel TT, et al. The safety and side effects of monoclonal antibodies. Nature Reviews, 2010;9:325-338.
Egan MA, et al. Human Immunodeficiency Virus Type 1 Envelope Protein Endocytosis Mediated by a Highly Conserved Intrinsic Internalization Signal in the Cytoplasmic Domain of gp41 Is Suppressed in the Presence of the Pr55gag Precursor Protein. Journal of Virology, 1996;70(10):6547-6556.
Cervantes-Acosta G, at al. Influence of Human Immunodeficiency Virus Type 1 Envelope Glycoprotein YXXL Endocytosis/Polarization Signal on Viral Accessory Protein Functions. Journal of Human Virology, 2001;4:249-259.
Fultz PN, et al. In Vivo Attenuation of Simian Immunodeficiency Virus by Disruption of a Tyrosine-Dependent Sorting Signal in the Envelope Glycoprotein Cytoplasmic Tail. Journal of Virology, 2001;75(1):278-291.
Doherty GJ, McMahon HT. Mechanisms of Endocytosis. Annu Rev Biochem, 2009;78:857-902.
Rajendran L, et al. Subcellular targeting strategies for drug design and delivery. Nature Reviews, 2010;9:29-42.
Kovtun YV, Goldmacher. Cell Killing by antibody-drug conjugates. Cancer Letters, 2007;255:232-240.
Luzio JP, et al. Lysosomes: fusion and function. Nature Reviews, 2007;8:622-632.
King HD, et al. Monoclonal Antibody Conjugates of Doxorubicin Prepared with Branched Linkers: A Novel Method for Increasing the Potency of Doxorubicin Immunoconjugates. Bioconjugate Chem, 1999;10:279-288.
Che C, et al. New Angiopep-Modified Doxorubicin (ANG1007) and Etoposide (ANG1009) Chemotherapeutics With Increased Brain Penetration. J Med Chem, 2010;53:2814-2824.
Kasiotis KM, et al. Synthesis and biological evaluation of novel daunorubicin-estrogen conjugates. Steroids, 2001;66:785-791.
Meyer-Losic F, et al. Improved Therapeutiv Efficacy of Doxorubicin through Conjugation with a Novel Peptide Drug Delivery Technology (Vectocell). J Med Chem, 2006;49:6908-6916.
Kratz F, et al. Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound. J Med Chem, 2002;45:5523-5533.
Kaneko T, et al. New Hydrazone Derivatives of Adriamycin and Their Immunoconjugates—a Correlation between Acid Stability and Cytotoxicity. Bioconjugate Chemistry, 1991;2(3):133-141.
Lee CC, et al. An Intramolecular Cyclization Reaction Is Responsible for the in Vivo Inefficacy and Apparent pH Insensitive Hydrolysis Kinetics of Hydrazone Carboxylate Derivatives of Doxorubicin. Bioconjugate Chem, 2006;17:1364-1368.
Sun C, et al. The design, synthesis, and evaluation of two universal doxorubicin-linkers: Preparation of conjugates that retain topoisomerase II activity. Bioorganic and Medicinal Chemistry Letters, 2006;16:104-107.
Carlson CB, et al. Selective Tumor Cell Targeting Using Low-Affinity, Multivalent Interactions. ACS Chemical Biology, 2006;2(2):119-127.
Pillay CS, et al. Endolysosomal proteolysis and its regulation. Biochem J, 2002;363:417-429.
Ickenstein LM, et al. A novel 125l-labeled daunorubicin derivative for radionuclide-based cancer therapy. Nuclear Medicine and biology, 2006;33:773-783.
Decuzzi P, Ferrari M. The role of specific and non-specific interactions in receptor-mediated endocytosis of nanoparticles. Biomaterials, 2007;28:2915-2922.
Sahay G, at al. Different Internalization Pathways of Polymeric Micelles and Unimers and Their Effects on Vesicular Transport. Bioconjugate Chem, 2008;19:2023-2029.
Wang J, et al. Delivery of drugs to cell membranes by encapsulation in PEG-PE micelles. Journal of Controlled Release, 2012;160:637-651.
Arlen PA, et al. Rapid Expression of Human Immunodeficiency Virus following Activation of Latently Infected Cells. Journal of Virology, 2006;80(3):1599-1603.
Korin YD, et al. Effects of Prostratin on T-Cell Activation and Human Immunodeficiency Virus Latency. Journal of Virology, 2002;76(16):8118-8123.
Kulkosky J, et al. Prostratin: activation of latent HIV-1 expression suggests a potential inductive adjuvant therapy for HAART. Blood, 2001;98(10):3006-3015.

(56) References Cited

OTHER PUBLICATIONS

Wender PA, et al. Practical Synthesis of Prostratin, DPP, and Their Analogs, Adjuvant Leads Against Latent HIV. Science, 2008;320:649-652.
Burke B, et al. Primary Cell Model for Activation-Inducible Human Immunodeficiency Virus. Journal of Virology, 2007;81(14):7424-7434.
Marsden MD, et al. HIV Latency in the Humanized, BLT Mouse. Journal of Virology, 2012;86(1):339-347.
Yang HC, et al. Small-molecule screening using a human primary cell model of HIV latency identifies compounds that reverse latency without cellular activation. J Clin Invest, 2009;119:3473-3485.
Cruz-Morales JA, Guadarrama P. Synthesis, characterization and computational modeling of cyclen substituted with dendrimeric branches. Dendrimeric and macrocyclic moieties working together in a collective fashion. Journal of Molecular Structure, 2005;779:1-10.
Kruger M, et al. Synthesis and Stability of Four Maleimide Derivatives of the Anticancer Drug Doxorubicin for the Preparation of Chemoimmunoconjugates. Chem Pharm Bull, 1997;45(2):399-401.

\* cited by examiner

FIGURE 2
Compound 4.19 (as formate salt)
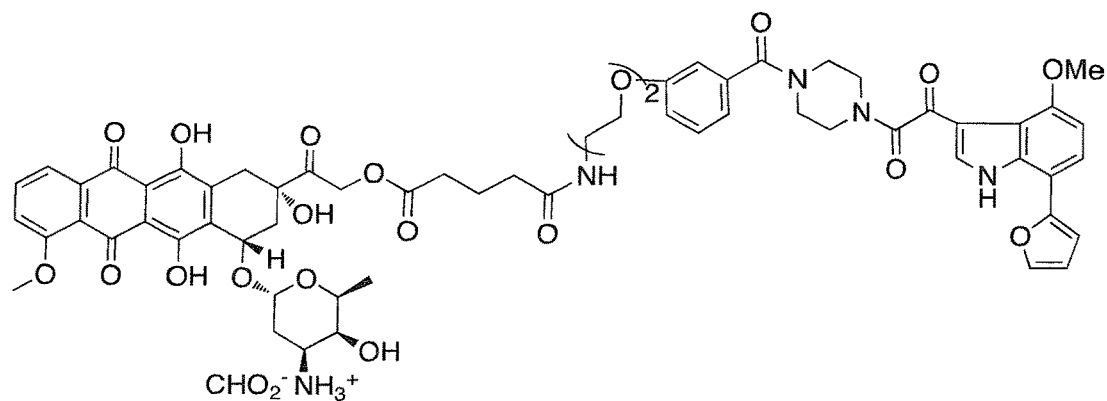
Compound 4.20 (as ammonium acetate salt)
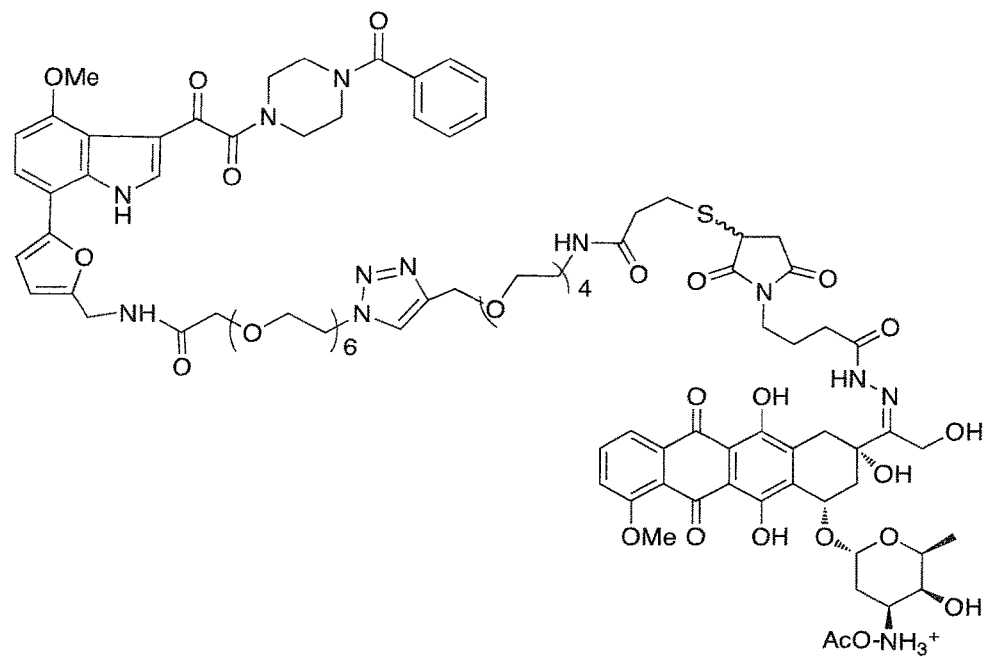

SOME LATENT HIV ACTIVATOR COMPOUNDS

SCHEME 1

Scheme 4.4

Scheme 4.5

Scheme 5

Scheme 6

FIGURE 17
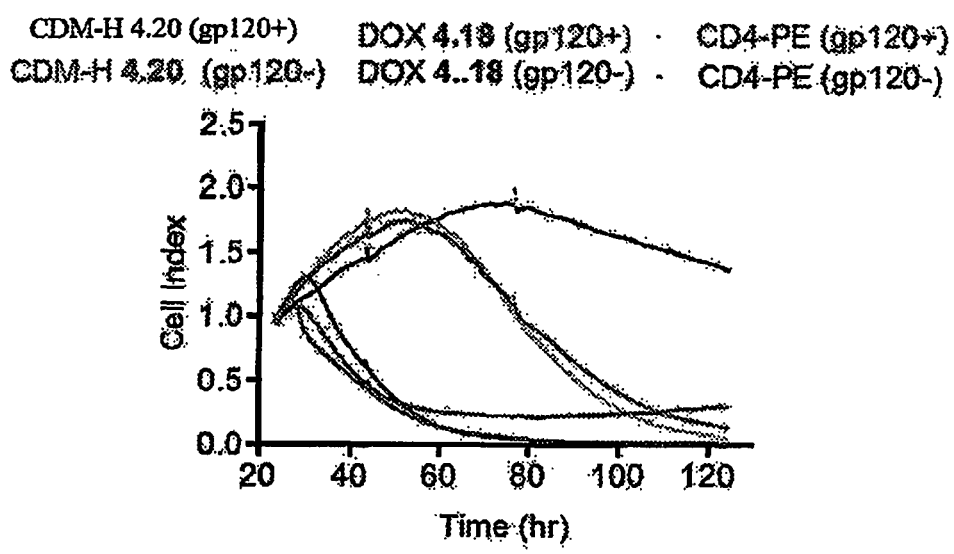
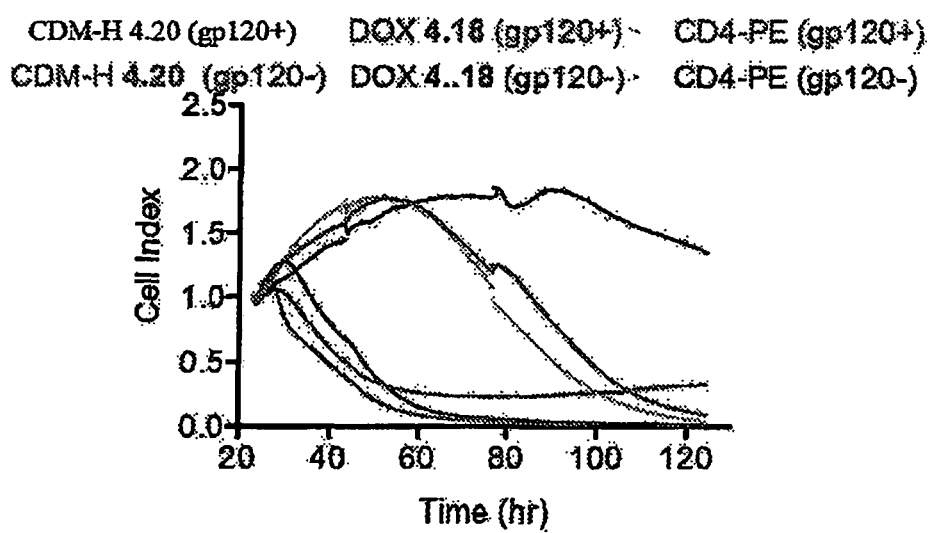

CYTOTOXIC-DRUG DELIVERING MOLECULES TARGETING HIV (CDM-HS), CYTOTOXIC ACTIVITY AGAINST THE HUMAN IMMUNODEFICIENCY VIRUS AND METHODS OF USE

PRIORITY CLAIM AND GRANT SUPPORT

This application is a United States national phase application of and claims priority from international patent application no. PCT/US2013/032044 filed 15 Mar. 2013, which claims priority from provisional application serial number U.S. 61/638,569 entitled, "Cytotoxic-drug Delivering Molecules Targeting HIV", filed Apr. 26, 2012, the entire contents of said applications being incorporated by reference herein.

This invention was made with government support under grant number OD002913 awarded by National institutes of Health. The government has certain rights in the invention.

FIELD OF THE INVENTION

The present invention relates to a novel class of small molecules that have the capacity to deliver cytotoxic therapeutics to HIV infected cells. These molecules, called cytotoxic-drug delivering molecules targeting HIV (CDM-Hs) contain an HIV gp 120 binding terminus referred to as the HIV binding terminus (VICB) that binds to the CD4 pocket on gp120. The VICB is covalently linked, through a specifically labile linker (in preferred embodiments, through a primary linker), to a cytotoxic agent (CYT), such as doxorubicin, chlorambucil or other cytotoxic agent as otherwise described herein. These bifunctional cytotoxic-drug delivering molecules of the present invention mechanistically target and inhibit human immunodeficiency virus (HIV) infection through binding to the HIV glycoprotein gp 120, while also delivering a cytotoxic agent to enhance therapy of HIV.

BACKGROUND AND GENERAL DISCUSSION OF THE INVENTION

The use of highly active antiretroviral therapy (HAART) can reduce HIV viremia to nearly undetectable levels in infected individuals through suppression of the viral lifecycle, however there are increasing problems associated with long-term toxicity, therapeutic compliance, high cost and the emergence of resistant strains.[1,2] In addition, suppressive treatment strategies lead to the formation of latent reservoirs of low-level HIV-1 replication. Upon treatment cessation, these persistent sources lead to rapid HIV-1 rebound;[3-5] thus, strict adherence to rigorous life-long treatment is required. Given these major barriers, new therapeutic strategies that are capable of eliminating these persistent reservoirs are critical to eradication of HIV infection.

Currently, one of the most investigated strategies aimed to cure HIV infection is the development of an HIV vaccine, however, as discussed in Chapter 2, major barriers have thwarted these efforts in the past quarter century. These barriers include HIV's enormous genetic diversity and propensity for genetic recombination, its detrimental toll on the immune system through the destruction of T cells, HIV's highly-evolved immune evasion strategies, and lastly, the establishment of latent reservoirs in which HIV is immunologically silent.[6] The major feature of HAART is its ability to block HIV replication and prevent new infection, however it fails at killing cells that are already infected. Thus, strategies that complement HAART-induced suppression by directly killing infected cells (including elimination of latent reservoirs) represent enormous potential towards efforts to cure HIV.[7]

Targeting HIV-Infected Cells with Cytotoxic Conjugates

Because Env resides on the surfaces of free virions and infected cells, and also mediates virus entry into host cells, numerous strategies for cytotoxic targeting of Env-expressing cellular reservoirs have been investigated. As discussed throughout the entirety of this thesis, ARM-Hs have the promise of being such a strategy, as we have demonstrated their success at not only inhibiting viral fusion, and therefore suppressing replication, but also at targeting HIV-1 gp120 expressing cells for immune-mediated toxicity. In addition, pioneering work focused on developing "immunotoxins," Env-targeting protein constructs conjugated to potent cellular toxins. Berger and colleagues published the first example of this class with their gp120-targeting CD4-*Pseudomonas* exotoxin A (PE) chimera, CD4-PE40.[8] Significant gp120-specific cellular toxicity (of both Env-transfected cells and constitutively HIV-infected cell lines) and inhibition of spreading infection by CD4-PE40 was demonstrated in vitro.[9-12, 96] This early success made it the only immunotoxin to enter Phase I clinical trials, where it failed due to a complete lack of antiviral activity at the maximum dosage which was limited by severe hepatocellular injury.[13-15] More recently, Pastan and co-workers conjugated PE to the single-chain Fv fragment of the broadly neutralizing 3B3 anti-gp120 antibody, yielding an antibody-toxin chimera, PE38, which demonstrated potent specific toxicity to Env-transfected cells as well as a chronically HIV-infected lymphocytic cell line.[11, 16] Importantly, PE38 demonstrated 20-30-fold more effective killing of HIV-infected cells than CD4-PE40 and is hypothesized to possess significantly less hepatotoxcity.[11, 17] Most recently, it has been demonstrated that these chimeras dramatically augment the antiviral activity of HAART in thy/liv-SCID-Hu mice,[17] providing promising evidence that such synergistic clinical strategies may indeed lead to an eradication strategy for HIV infection.[7] Other notable examples include work by Root et al. who recently developed a 5-Helix protein-PE chimera that binds to HIV-1 gp41, demonstrating potent cytotoxicity towards HIV-1 infected cells. In work by Johansson et. al., the potent DNA-intercalating small molecule drug doxorubicin was conjugated to an anti-gp120 mAb and then administered to mice possessing HIV-1/MuLV-infected splenocytes, resulting in the elimination of the infection.[18]

Collectively, this work demonstrates the overwhelming promise of strategies to direct targeted cytotoxicity against HIV-infected cells. However, all previously reported strategies utilize protein constructs, which have shown acute toxicity and immunogenicity in cellular systems[7, 19] and are inherently limited by the characteristics of all protein therapeutics.[20] These limitations include the potential for life-threatening allergic reactions, poor tissue penetration, immunogenicity (even in the case of "humanized" proteins),[21] lack of oral bioavailability, requirement for low-temperature storage, and high cost.[22] Given the promise of such approaches, we sought to overcome their limitations by utilizing our gp120-targeting small molecule scaffold to deliver cytotoxic compounds to HIV-infected cells. In addition, such agents might prove particularly useful if antibody-mediated killing (via ARM-Hs) proves ineffective in vivo, or in patients with highly compromised immune systems.

SUMMARY OF THE INVENTION

The present invention relates to Cytotoxic-drug Delivering Molecules Targeting HIV (CDM-Hs) compounds according to the general formula:

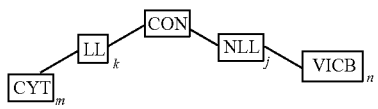
Where CYT is a moiety of a cytotoxic agent capable of causing death of a cell into which it is introduced;

VICB is a virus invasion cell binding moiety comprising a group which is capable of binding to gp120 envelope protein on HIV virus or a cell surface of CD4 cells which are infected with HIV (HIV+) in said patient;

LL is a labile linker molecule which chemically links CYT to CON in a molecule either directly or optionally, through a non-labile linker and is labile when said compound enters a cell;

NLL is a non-labile linker molecule which chemically links VICB to CON in a molecule;

CON is a bond or a connector molecule (which may be bifunctional or multifunctional) which links LL or NLL to CYT and/or VICB;

Each m in a molecule is independently an integer from 1 to 25, 1 to 20, 1 to 15, 1 to 10, 1 to 5, 1 to 4, 1 to 3, 2 to 3, 2 to 5, 1 to 2 or 1 (often, m is 1, 2 or 3, more often 1);

Each n in a molecule is independently an integer from 1 to 15, 1 to 10, 1 to 5, 1 to 3, 2 to 3, 2 to 5, 1 to 2 or 1 (often, n is 1);

Each j is independently 0, 1, 2, 3, 4 or 5 (preferably 0 or 1, more preferably 1); and Each k is independently 0, 1, 2, 3, 4 or 5 (preferably 0 or 1, more preferably 1), with the proviso that k and/or j (preferably k, often k and j) is at least 1 when CON is a bond.

or a pharmaceutically acceptable salt, stereoisiomer, solvate or polymorph thereof.

In certain aspects of the invention, compounds according to the present invention are represented by the chemical formula:

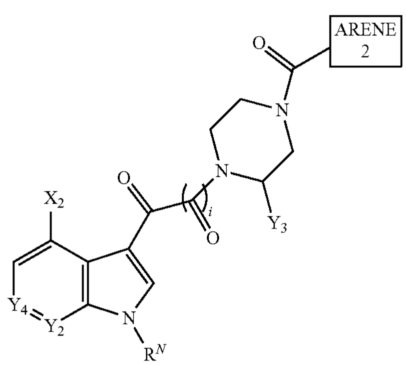

Where $Y_2$ is N or a C—$R^Y$ group;

$R^Y$ is H, $C_1$-$C_6$ alkyl, O—($C_1$-$C_6$ alkyl), a halogen (preferably F, Br or Cl) or a 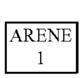 group;

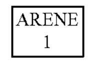

is an optionally substituted aryl or heteroaryl group, preferably a group according the chemical structure:

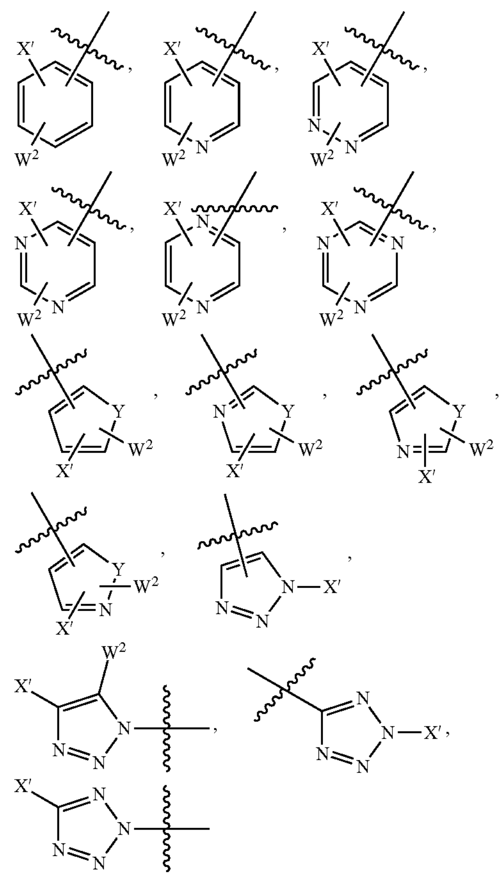

where $W^2$ is H, —$(CH_2)_n$OH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$NHC(O)—$R_1$, —$(CH_2)_n$C(O)—$NR_1R_2$, —$(CH_2O)_n$H, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(CH_2O)_n$NHC(O)—$R_1$, —$(CH_2O)_n$C(O)—$NR_1R_2$, $NO_2$, CN or halogen (preferably F or Cl);

$R_1$ and $R_2$ are each independently H or a $C_1$-$C_6$ alkyl group;

X' is H, $C_1$-$C_6$ alkyl, O—$C_1$-$C_6$ alkyl (preferably OMe), halogen (F, Cl, Br) or a 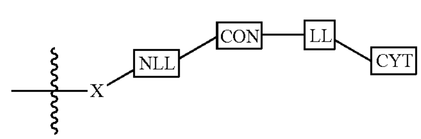 group;

Where X is —$NR^{1N}$—, —$NR^{1N}$CO—, —O—, —$CH_2$—, —S—, —OCONH— or —NHCONH—;

NLL is a non-labile linker;

LL is a labile linker which is cleavable upon entry of the compound into a cell and is optionally linked to [CON] through a second non-labile linker [NLL];

CON is a connector moiety which connects said non-labile linker (NLL) with said labile-linker (LL);

CYT is a cytotoxic moiety which is capable of causing cell death upon entry of the compound into a cell;

$R^{1N}$ is H or a $C_1$-$C_3$ alkyl group optionally substituted with one or two hydroxyl groups (most often H);

$Y_3$ is H or a $C_1$-$C_3$ alkyl group (disposed out of or into the plane, preferably out of the plane on the chiral carbon), preferably H or $CH_3$;

$Y_4$ is N or C—H;

$R^N$ is H or a $C_1$-$C_3$ alkyl group which is optionally substituted with one or two hydroxyl groups;

$X_2$ is H, $C_1$-$C_6$ alkyl, O—$C_1$-$C_6$ alkyl (preferably OMe), halogen (F, Cl, Br) or a

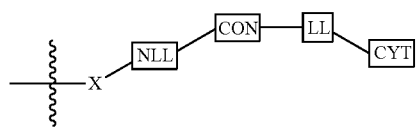

group as described above;

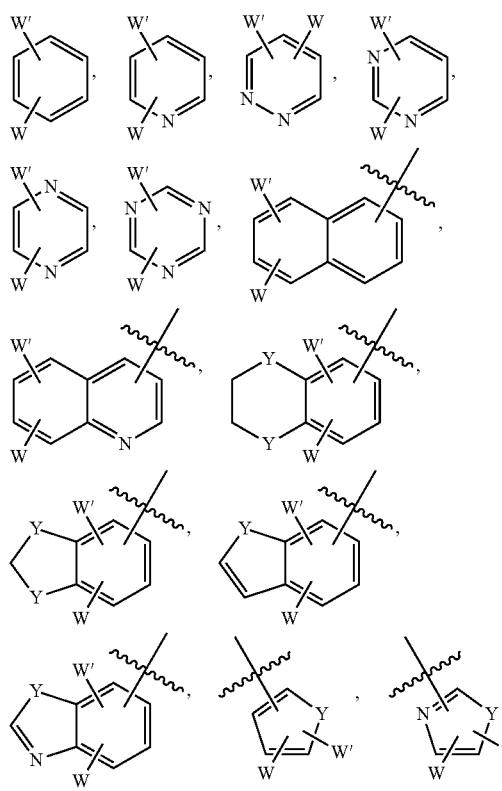

is an optionally substituted aryl or heteroaryl group preferably a group according to the chemical structure:

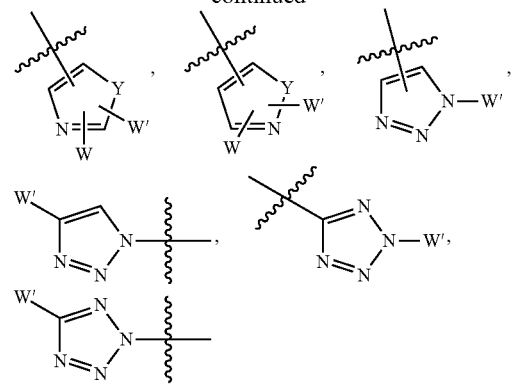

where Y is O, S or N—R where R is H or a $C_1$-$C_3$ alkyl group;

W and W' are each independently H, —$(CH_2)_n$OH, —$(CH_2)_n$COOH, —$(CH_2)_n$O—$(C_1$-$C_6$ alkyl), —$(CH_2)_n$C(O)—$(C_1$-$C_6$ alkyl), —$(CH_2)_n$—$NR_1R_2$, —$(CH_2)_n$NHC(O)—$R_1$, —$(CH_2)_n$C(O)—$NR_1R_2$, —$(CH_2O)_n$H, $(OCH_2)_n$NR_1R_2$, $(OCH_2)_n$NR_1R_2$, $(OCH_2)_n$CONR_1R_2$, $(OCH_2)_n$CO_2R_1$, —$(CH_2O)_n$COOH, $C_1$-$C_6$ alkyl, —$(CH_2O)_n$O—$(C_1$-$C_6$ alkyl), —$(CH_2O)_n$C(O)—$(C_1$-$C_6$ alkyl), —$(OCH_2)_n$OR_1$, —$(OCH_2)_n$NHC(O)—$R_1$, —$(CH_2O)_n$C(O)—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group), or a

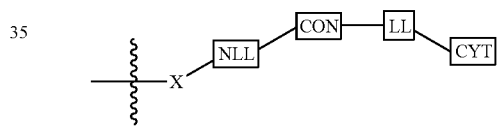

group as described above;

$R_1$ and $R_2$ are the same as above;

Each i is 0 or 1 (preferably 1);

Each n is independently 0, 1, 2, 3, 4, 5, or 6 (preferably 0 or 1), or a pharmaceutically acceptable salt, stereoisomer, solvate or polymorph thereof.

In certain embodiments, the compound according to the present invention is represented by the chemical formula:

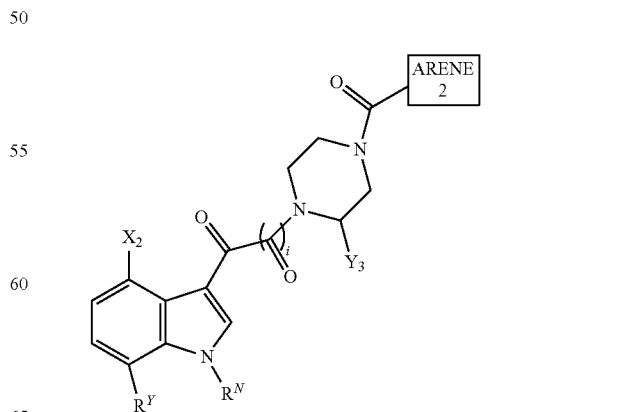

Where $R^N$ is H or a $C_1$-$C_3$ alkyl group;

$R^Y$ is a

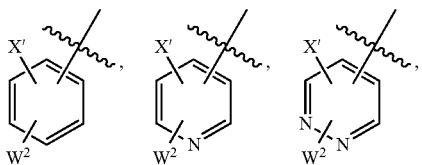

group;

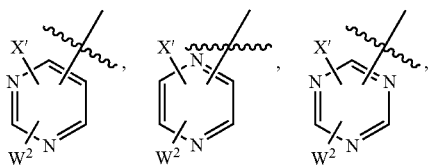

is a group according the chemical structure:

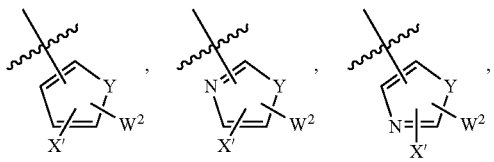

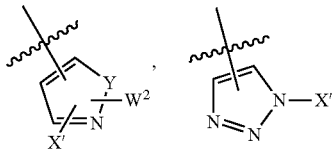

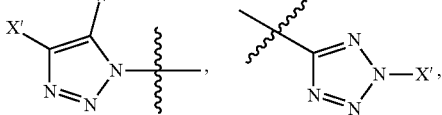

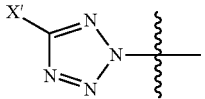

where $W^2$ is H, —$(CH_2)_n$OH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$NHC(O)—$R_1$, —$(CH_2)_n$C(O)—$NR_1R_2$, —$(CH_2O)_n$H, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(CH_2O)_n$NHC(O)—$R_1$, —$(CH_2O)_n$C(O)—$NR_1R_2$, $NO_2$, CN or halogen (preferably F or Cl);

$R_1$ and $R_2$ are each independently H or a $C_1$-$C_6$ alkyl group; and $X'$ is a

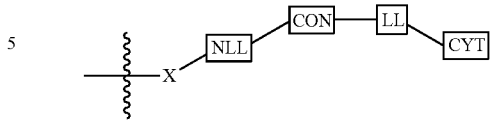

group;
where X is —$NR^{1N}$—, —$NR^{1N}$CO—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;
$Y_3$ is H or $CH_3$ (disposed out of or into the plane, preferably out of the plane on the chiral carbon);
$X_2$ is H, $C_1$-$C_6$ alkyl, O—$C_1$-$C_6$ alkyl (preferably OMe) or halogen (F, Cl, Br), preferably $X_2$ is OMe;

ARENE 2 is a group according to the chemical structure:

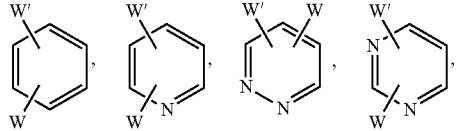

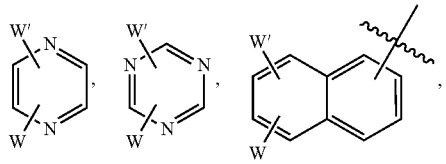

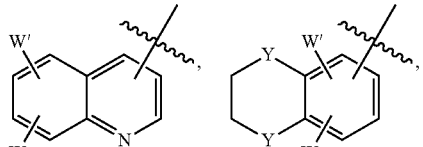

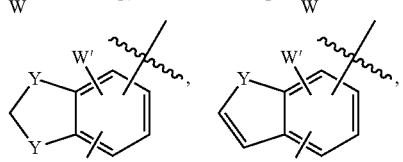

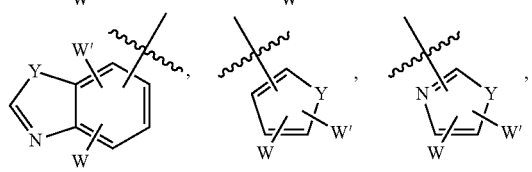

-continued

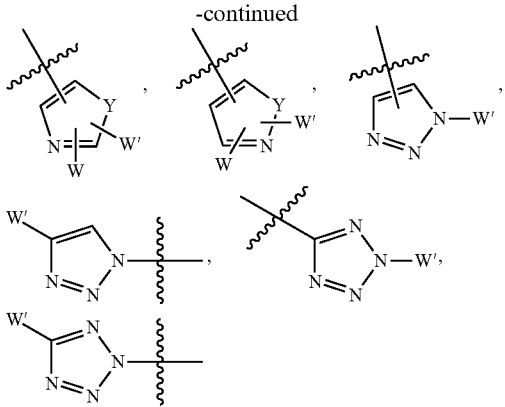

where Y is O, S or N—R where R is H or a $C_1$-$C_3$ alkyl group;

W and W' are each independently H, —$(CH_2)_n$OH, —$(CH_2)_n$COOH, —$(CH_2)_n$O—($C_1$-$C_6$ alkyl), —$(CH_2)_n$C(O)—($C_1$-$C_6$ alkyl), —$(CH_2)_n$—$NR_1R_2$, —$(CH_2)_n$NHC(O)—$R_1$, —$(CH_2)_n$C(O)—$NR_1R_2$, —$(CH_2O)_n$H, $(OCH_2)_n$$NR_1R_2$, $(OCH_2)_n$$NR_1R_2$, $(OCH_2)_n$$CONR_1R_2$, $(OCH_2)_n$$CO_2R_1$, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(OCH_2)_n$$OR_1$, —$(OCH_2)_n$NHC(O)—$R_1$, —$(CH_2O)_n$C(O)—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);

$R_1$ and $R_2$ are the same as above;

Each i is 0 or 1 (preferably 1);

Each n is independently 0, 1, 2, 3, 4, 5, or 6 (preferably 0 or 1), or a pharmaceutically acceptable salt, stereoisomer, solvate or polymorph thereof.

In other preferred embodiments of the invention, compounds according to the present invention may be represented by the chemical structure:

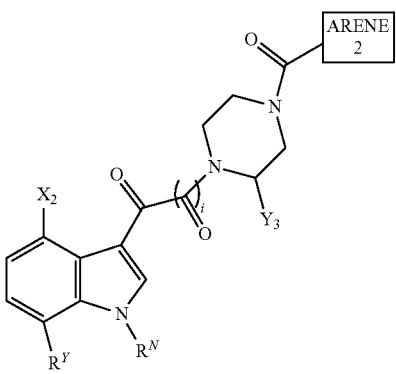

where $R^N$ is H or a $C_1$-$C_3$ alkyl group;
$R^Y$ is a

group;

is a group according the chemical structure:

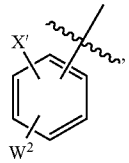

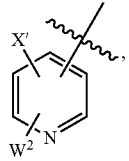

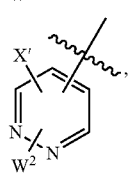

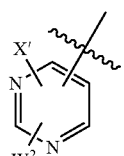

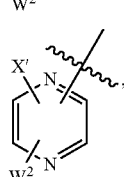

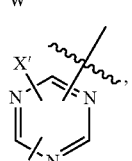

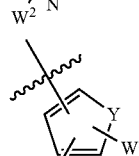

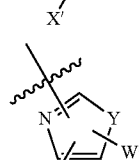

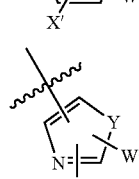

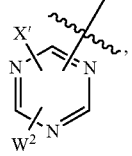

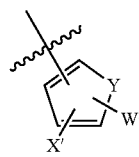

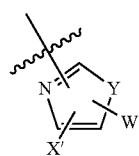

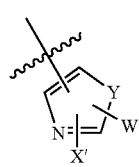

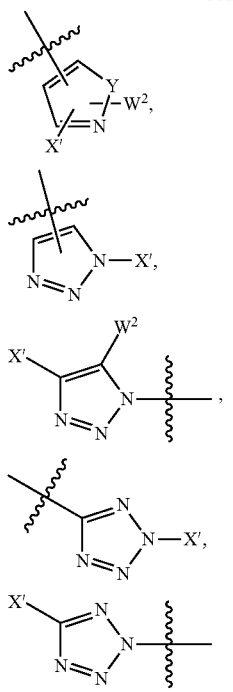

where $W^2$ is H, —$(CH_2)_nOH$, —$(CH_2)_nCOOH$, $C_1$-$C_6$ alkyl, —$(CH_2)_nO$—($C_1$-$C_6$ alkyl), —$(CH_2)_nC(O)$—($C_1$-$C_6$ alkyl), —$(CH_2)_nNHC(O)$—$R_1$, —$(CH_2)_nC(O)$—$NR_1R_2$, —$(CH_2O)_nH$, —$(CH_2O)_nCOOH$, $C_1$-$C_6$ alkyl, —$(CH_2O)_n$O—($C_1$-$C_6$ alkyl), —$(CH_2O)_nC(O)$—($C_1$-$C_6$ alkyl), —$(CH_2O)_nNHC(O)$—$R_1$, —$(CH_2O)_nC(O)$—$NR_1R_2$, $NO_2$, CN or halogen (preferably F or Cl);

$R_1$ and $R_2$ are each independently H or a $C_1$-$C_6$ alkyl group (preferably $W^2$ is H); and X' is H, $C_1$-$C_6$ alkyl, O—$C_1$-$C_6$ alkyl (preferably OMe) or halogen (F, Cl, Br), preferably X' is H;

$X_2$ is H, $C_1$-$C_6$ alkyl, O—$C_1$-$C_6$ alkyl (preferably OMe) or halogen (F, Cl, Br), preferably $X_2$ is OMe;

$Y_3$ is H or $CH_3$ (disposed out of or into the plane, preferably out of the plane on the chiral carbon);

ARENE 2 is a group according to the chemical structure:

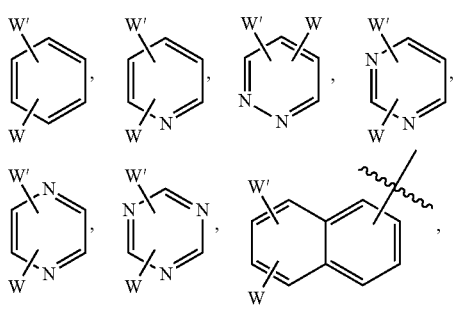

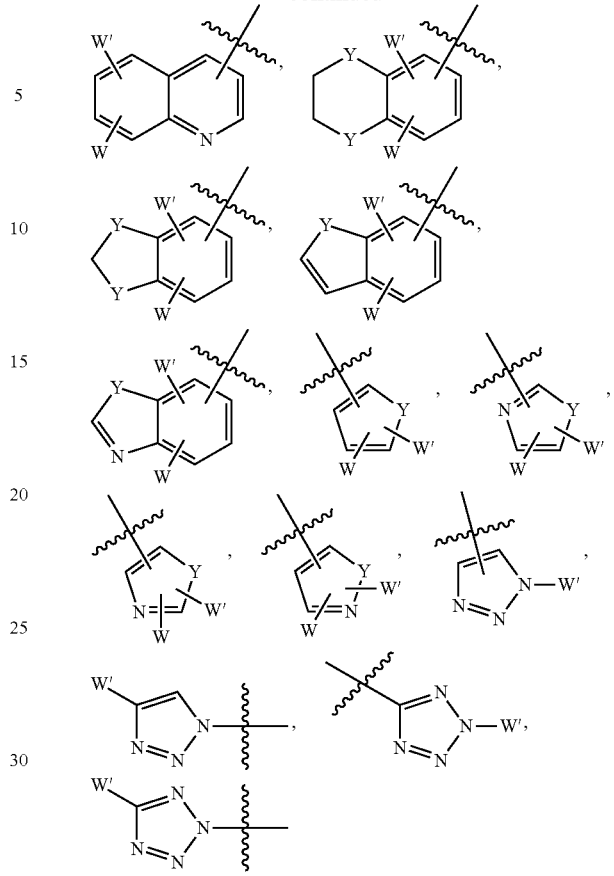

where Y is O, S or N—R where R is H or a $C_1$-$C_3$ alkyl group;

W is H, —$(CH_2)_nOH$, —$(CH_2)_nCOOH$, —$(CH_2)_nO$—($C_1$-$C_6$ alkyl), —$(CH_2)_nC(O)$—($C_1$-$C_6$ alkyl), —$(CH_2)_n$—$NR_1R_2$, —$(CH_2)_nNHC(O)$—$R_1$, —$(CH_2)_nC(O)$—$NR_1R_2$, —$(CH_2O)_nH$, $(OCH_2)_nNR_1R_2$, $(OCH_2)_nNR_1R_2$, $(OCH_2)_n$CONR$_1R_2$, $(OCH_2)_nCO_2R_1$, —$(CH_2O)_nCOOH$, $C_1$-$C_6$ alkyl, —$(CH_2O)_nO$—($C_1$-$C_6$ alkyl), —$(CH_2O)_nC(O)$—($C_1$-$C_6$ alkyl), —$(OCH_2)_nOR_1$, —$(OCH_2)_nNHC(O)$—$R_1$, —$(CH_2O)_nC(O)$—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);

$R_1$ and $R_2$ are the same as above;

W' is a

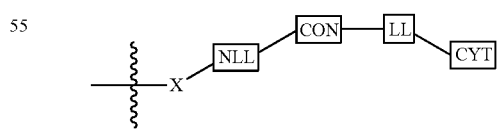

group;

where X is —$NR^{1N}$—, —$NR^{1N}CO$—, —O—, —$CH_2$—, —S—, —OCONH— or —NHCONH—;

NLL is a non-labile linker;

LL is a labile linker which is cleavable upon entry of the compound into a cell and is optionally linked to [CON] through a second non-labile linker [NLL];

CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;
Each i is 0 or 1 (preferably 1); and
Each n is independently 0, 1, 2, 3, 4, 5, or 6 (preferably 0 or 1),
or a pharmaceutically acceptable salt, stereoisomer, solvate or polymorph thereof.

In other preferred embodiments of the invention, compounds according to the present invention may be represented by the chemical structure:

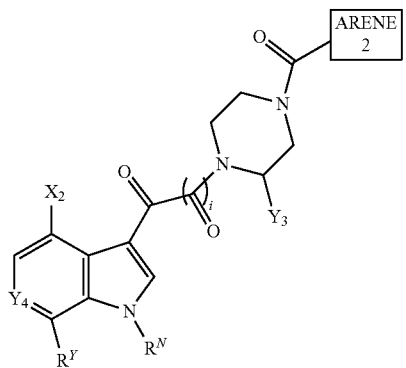

where $R^N$ is H or a $C_1$-$C_3$ alkyl group;
$R^Y$ is H, $C_1$-$C_6$ alkyl, O—$C_1$-$C_6$ alkyl (preferably OMe) or halogen (F, Cl, Br), preferably $R^Y$ is OMe;
$X_2$ is H, $C_1$-$C_6$ alkyl, O—$C_1$-$C_6$ alkyl (preferably OMe) or halogen (F, Cl, Br), preferably $X_2$ is OMe;
$Y_3$ is H or $CH_3$ (disposed out of or into the plane, preferably out of the plane on the chiral carbon);
$Y^4$ is N or C—H (preferably N);

is a group according to the chemical structure:

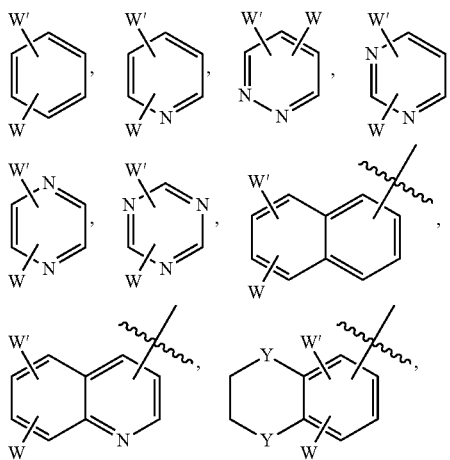

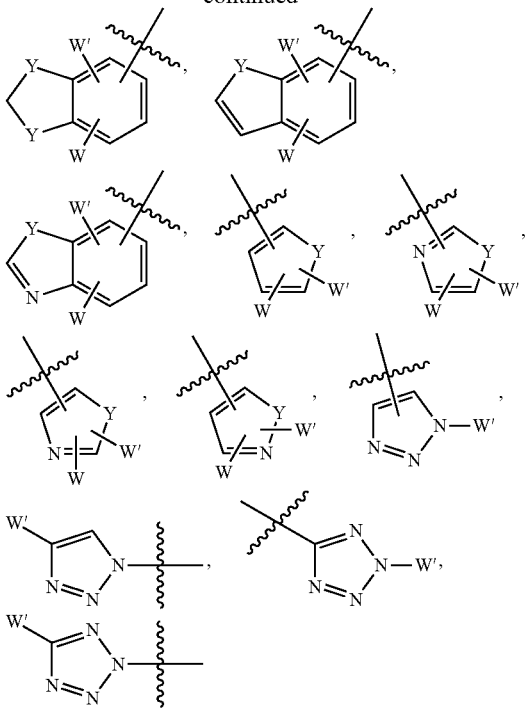

where Y is O, S or N—R where R is H or a $C_1$-$C_3$ alkyl group;
W is H, —$(CH_2)_n$OH, —$(CH_2)_n$COOH, —$(CH_2)_n$O—($C_1$-$C_6$ alkyl), —$(CH_2)_n$C(O)—($C_1$-$C_6$ alkyl), —$(CH_2)_n$—$NR_1R_2$, —$(CH_2)_n$NHC(O)—$R_1$, —$(CH_2)_n$C(O)—$NR_1R_2$, —$(CH_2O)_n$H, $(OCH_2)_n$$NR_1R_2$, $(OCH_2)_n$$NR_1R_2$, $(OCH_2)_n$CONR$_1$R$_2$, $(OCH_2)_n$CO$_2$R$_1$, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(OCH_2)_n$OR$_1$, —$(OCH_2)_n$NHC(O)—$R_1$, —$(CH_2O)_n$C(O)—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);
$R_1$ and $R_2$ are the same as above;
W' is a

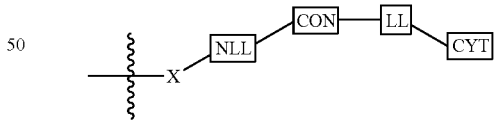

group;
where X is —$NR^{1N}$—, —$NR^{1N}$CO—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;

Each i is 0 or 1 (preferably 1); and
Each n is independently 0, 1, 2, 3, 4, 5, or 6 (preferably 0 or 1),
or a pharmaceutically acceptable salt, stereoisomer, solvate or polymorph thereof.

In still other preferred embodiments, compounds according to the present invention may be represented by the chemical structure:

In certain embodiments according to the invention, compounds according to the present invention are represented by the chemical formula:

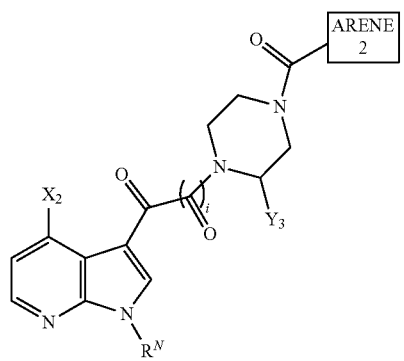

where $R^N$ is H or a $C_1$-$C_3$ alkyl group (preferably H);
$X_2$ is H, $C_1$-$C_6$ alkyl, O—$C_1$-$C_6$ alkyl (preferably OMe) or halogen (F, Cl, Br), preferably $X_2$ is OMe;
$Y_3$ is H or $CH_3$ (disposed out of or into the plane, preferably out of the plane on the chiral carbon);

ARENE 2 is a group according to the chemical structure:

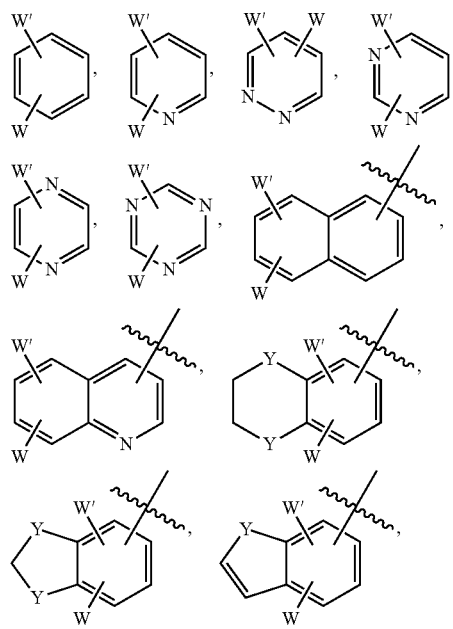

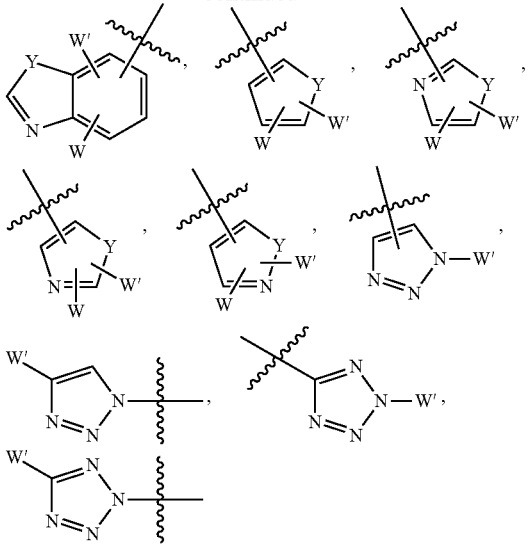

where Y is O, S or N—R where R is H or a $C_1$-$C_3$ alkyl group;
W is H, —$(CH_2)_n$OH, —$(CH_2)_n$COOH, —$(CH_2)_n$O—($C_1$-$C_6$ alkyl), —$(CH_2)_n$C(O)—($C_1$-$C_6$ alkyl), —$(CH_2)_n$—$NR_1R_2$, —$(CH_2)_n$NHC(O)—$R_1$, —$(CH_2)_n$C(O)—$NR_1R_2$, —$(CH_2O)_n$H, $(OCH_2)_n$$NR_1R_2$, $(OCH_2)_n$$NR_1R_2$, $(OCH_2)_n$$CONR_1R_2$, $(OCH_2)_n$$CO_2R_1$, —$(CH_2O)_n$COOH, $C_1$-$C_6$ alkyl, —$(CH_2O)_n$O—($C_1$-$C_6$ alkyl), —$(CH_2O)_n$C(O)—($C_1$-$C_6$ alkyl), —$(OCH_2)_n$$OR_1$, —$(OCH_2)_n$NHC(O)—$R_1$, —$(CH_2O)_n$C(O)—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);
$R_1$ and $R_2$ are the same as above;
W' is a

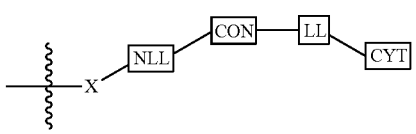

group;
where X is —$NR^{1N}$—, —$NR^{1N}$CO—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;
Each i is 0 or 1 (preferably 1); and
Each n is independently 0, 1, 2, 3, 4, 5, or 6 (preferably 0 or 1),
or a pharmaceutically acceptable salt, stereoisomer, solvate or polymorph thereof.

In still other embodiments, compounds according to the present invention may be represented by the following chemical structure:

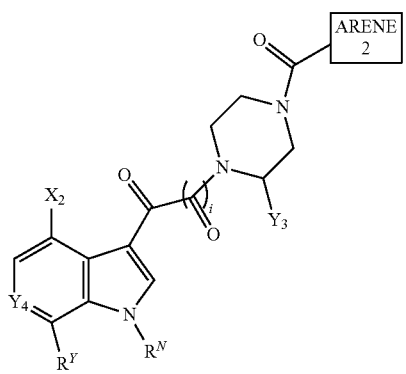

where $R^N$ is H or a $C_1$-$C_3$ alkyl group;
$R^Y$ is H, $C_1$-$C_6$ alkyl, O—$C_1$-$C_6$ alkyl (preferably OMe) or halogen (F, Cl, Br), preferably $R^Y$ is OMe;
$X_2$ is a

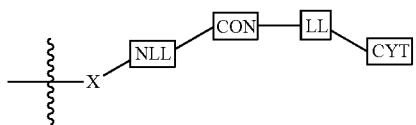

group;
where X is —$NR^{1N}$—, —$NR^{1N}CO$—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;
$Y_3$ is H or $CH_3$ (disposed out of or into the plane, preferably out of the plane on the chiral carbon);
$Y^4$ is N or C—H (preferably N);

is a group according to the chemical structure:

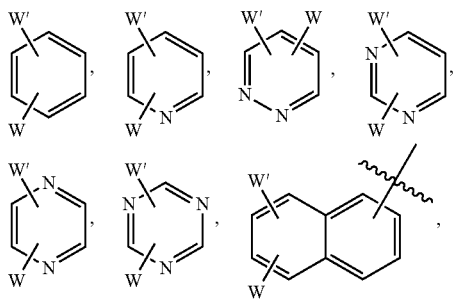

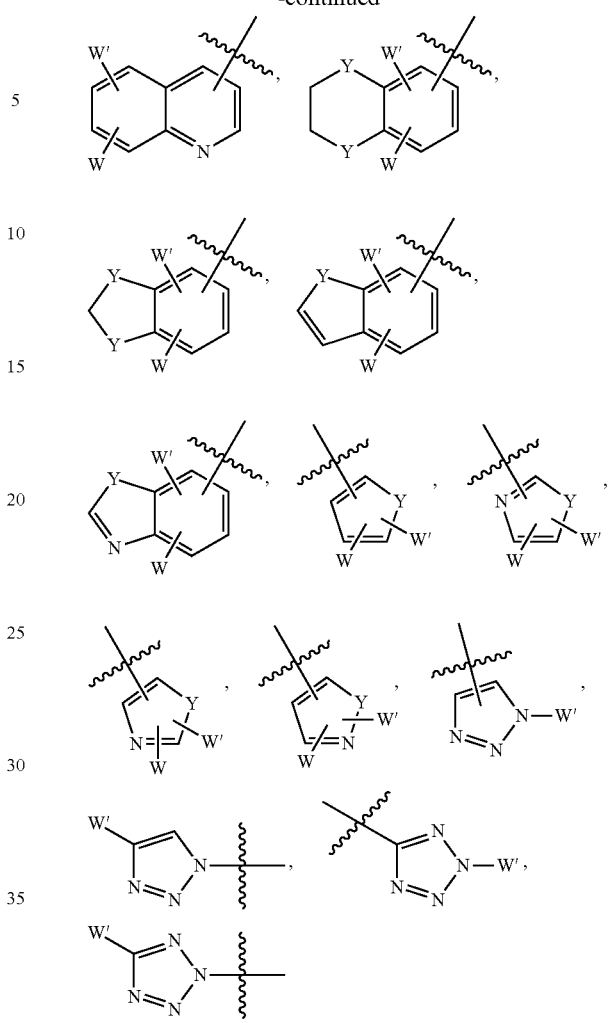

where Y is O, S or N—R where R is H or a $C_1$-$C_3$ alkyl group;
W and W' are each independently H, —$(CH_2)_nOH$, —$(CH_2)_nCOOH$, —$(CH_2)_nO$—$(C_1$-$C_6$ alkyl), —$(CH_2)_nC(O)$—$(C_1$-$C_6$ alkyl), —$(CH_2)_n$—$NR_1R_2$, —$(CH_2)_nNHC(O)$—$R_1$, —$(CH_2)_nC(O)$—$NR_1R_2$, —$(CH_2O)_nH$, $(OCH_2)_nNR_1R_2$, $(OCH_2)_nNR_1R_2$, $(OCH_2)_nCONR_1R_2$, $(OCH_2)_nCO_2R_1$, —$(CH_2O)_nCOOH$, $C_1$-$C_6$ alkyl, —$(CH_2O)_nO$—$(C_1$-$C_6$ alkyl), —$(CH_2O)_nC(O)$—$(C_1$-$C_6$ alkyl), —$(OCH_2)_nOR_1$, —$(OCH_2)_nNHC(O)$—$R_1$, —$(CH_2O)_nC(O)$—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);
$R_1$ and $R_2$ are the same as above;
Each i is 0 or 1 (preferably 1); and
Each n is independently 0, 1, 2, 3, 4, 5, or 6 (preferably 0 or 1),
or a pharmaceutically acceptable salt, stereoisomer, solvate or polymorph thereof.

In still other embodiments, compounds according to the present invention may be represented by the chemical structure:

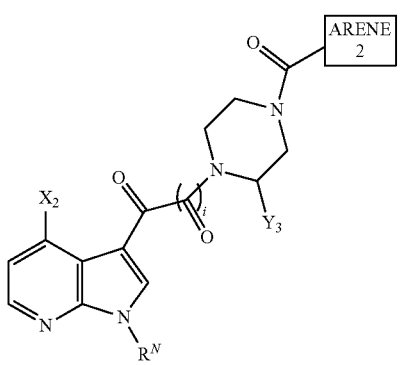

where $R^N$ is H or a $C_1$-$C_3$ alkyl group (preferably H);
$X_2$ is a

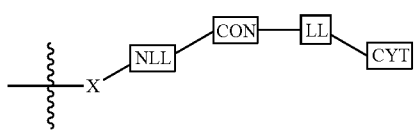

group;
where X is —$NR^{1N}$—, —$NR^{1N}CO$—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups, preferably H;
$Y_3$ is H or $CH_3$ (disposed out of or into the plane, preferably out of the plane on the chiral carbon);

is a group according to the chemical structure:

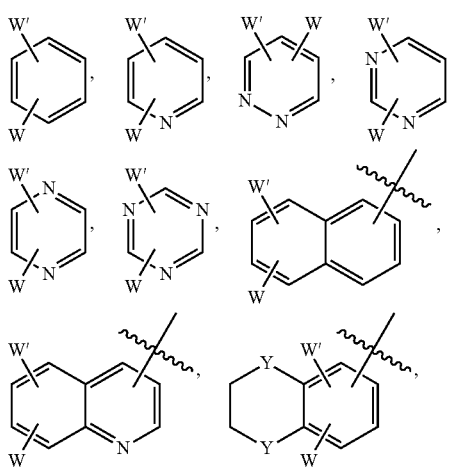

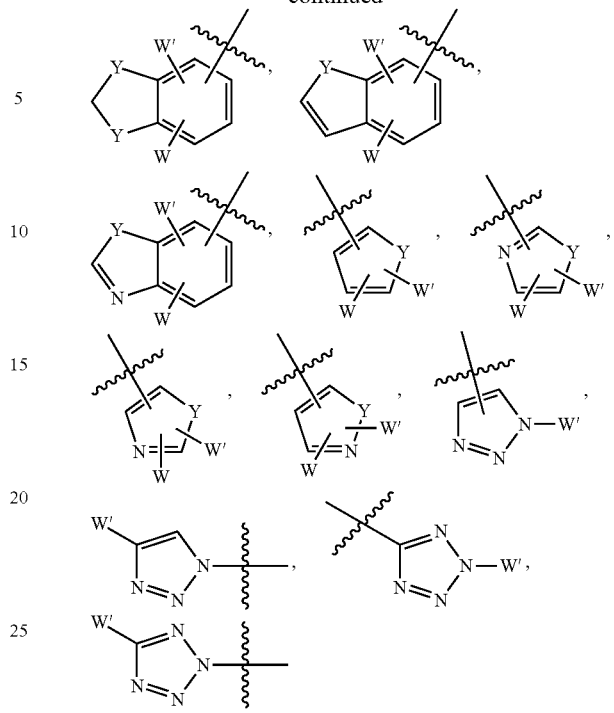

where Y is O, S or N—R where R is H or a $C_1$-$C_3$ alkyl group;
W and W' are each independently H, —$(CH_2)_n$OH, —$(CH_2)_n$COOH, —$(CH_2)_n$O—$(C_1$-$C_6$ alkyl), —$(CH_2)_n$C(O)—$(C_1$-$C_6$ alkyl), —$(CH_2)_n$—$NR_1R_2$, —$(CH_2)_n$NHC(O)—$R_1$, —$(CH_2)_n$C(O)—$NR_1R_2$, —$(CH_2O)_n$H, $(OCH_2)_n$$NR_1R_2$, $(OCH_2)_n$$NR_1R_2$, $(OCH_2)_n$$CONR_1R_2$, $(OCH_2)_n$$CO_2R_1$, —$(CH_2O)_n$COOH, $C_1$-$C_6$ alkyl, —$(CH_2O)_n$O—$(C_1$-$C_6$ alkyl), —$(CH_2O)_n$C(O)—$(C_1$-$C_6$ alkyl), —$(CH_2O)_n$$OR_1$, —$(OCH_2)_n$NHC(O)—$R_1$, —$(CH_2O)_n$C(O)—$NR_1R_2$, $NO_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group);
$R_1$ and $R_2$ are the same as above;
Each i is 0 or 1 (preferably 1); and
Each n is independently 0, 1, 2, 3, 4, 5, or 6 (preferably 0 or 1),
or a pharmaceutically acceptable salt, stereoisomer, solvate or polymorph thereof.

In certain embodiments, $R^Y$ is an optionally substituted phenyl, naphthyl, pyridyl, thiazolyl, isothiazolyl, oxazolyl, isoxazolyl, furanyl or thiophenyl group. Often, $R^Y$ is an optionally substituted 2- or 3-furanyl group, including a furanyl group which is substituted with a group

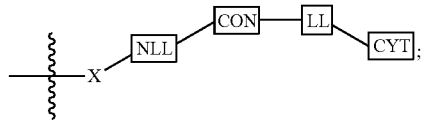

where X is —$NR^{1N}$—, —$NR^{1N}CO$—, —O—, —$CH_2$—, —S—, —OCONH— or —NHCONH—;
NLL is a non-labile linker;
LL is a labile linker which is cleavable upon entry of the compound into a cell and is optionally linked to [CON] through a second non-labile linker [NLL];

CON is a connector moiety which connects said non-labile linker (NLL) with said labile-linker (LL);

CYT is a cytotoxic moiety which is capable of causing cell death upon entry of the compound into a cell; and $R^{1N}$ is H or a $C_1$-$C_3$ alkyl group optionally substituted with one or two hydroxyl groups, preferably H;

In certain of these embodiments the $R^Y$ group is optionally substituted with a —NH—, —NHCO—, —O—, —CH$_2$—, —S—, —OCONH or —NHC(O)NH— group which links the $R^Y$ group to the linker group and/or the connecting (CON) group.

The non-labile linker (NLL) for use in the present invention is represented by any chemical structure which is compatible with the chemistry of the bifunctional compounds and its administration to a patient and does not readily cleave in a cell in which the bifunctional molecule is introduced. In general, the NLL for use in compounds according to the present invention is at least one chemical moiety, more often at least two chemical moieties in length to upwards of 100 or more moieties in length. These linkers are presented in detail hereinbelow. Preferred non-labile linkers include, for example, (poly)ethylene glycol linkers ranging in length from 2 to about 100 ethylene glycol units, preferably about 2 to 10 ethylene glycol units, about 2 to about 25, about 2 to about 15, about 2 to about 14, about 4 to about 10 units. In other preferred embodiments, the non-labile linker (NLL) is a polyethylene-co-polypropylene (PEG/PPG block copolymer) linker ranging from 2 to about 100, about 2 to about 25, about 2 to about 15, about 2 to about 14, about 2 to about 10, about 4 to about 10, combined ethylene glycol and propylene glycol units.

(Poly)alkylene chains and polyaminoacid chains as otherwise described herein are also preferred NLL for use in the present invention. When present, these have 1 to about 100 units, often about 2 to 10 units, about 2 to about 25, about 2 to about 15, about 2 to about 14, about 4 to about 10 units. NLL for use in the present invention may also contain one or more connector CON moieties as otherwise described herein which chemically connect separate (two or more) NLL portions, the entire portion being labeled a NLL.

In certain preferred embodiments, the non-labile linker (NLL) is represented by the following exemplary structures (note that the NLL may contain one or more CON moieties):

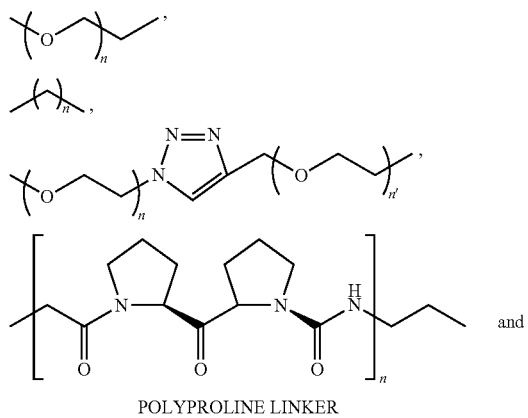

POLYPROLINE LINKER

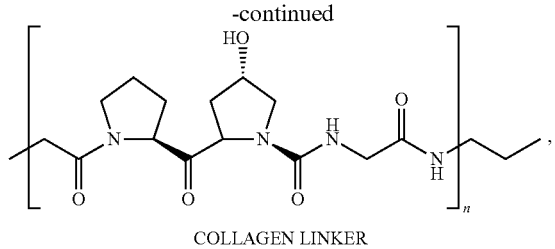

COLLAGEN LINKER among numerous others, as described herein.

where n and n' are each independently 0 to 100, preferably 1 to 100, more preferably about 2 to about 20, about 2 to about 10, about 4 to about 10, about 4 to about 8.

Other non-labile linkers are presented in greater detail hereinbelow.

The labile linker (LL) for use in the present invention is represented by any chemical structure which is compatible with the chemistry of the bifunctional compounds and its administration to a patient and readily cleaves in a cell in which the bifunctional molecule is introduced, thus releasing the cytotoxic agent within the cell. In general, the LL for use in compounds according to the present invention is at least two moieties in length and functionally contains a group which is readily cleaved within a cell. The cleavable moieties may be hydrolytically cleaved (acid labile), and include, for example, amides, esters, thioesters, vinyl ethers, urethanes, ketals, diketals, ketal ethers, diketal ethers, thioketals, iminoamides, succinimido iminoamides, trityl amide amine, methoxytrityl amide amine, imides, including succinimide, reductively cleaved (i.e., reductively labile), e.g., disulfide groups) or enzymatically cleaved (e.g., protease substrates, including numerous di-, tri-, tetra- and pentapeptides).

Exemplary acid labile linkers pursuant to the present invention include, for example moieties according to the chemical structure:

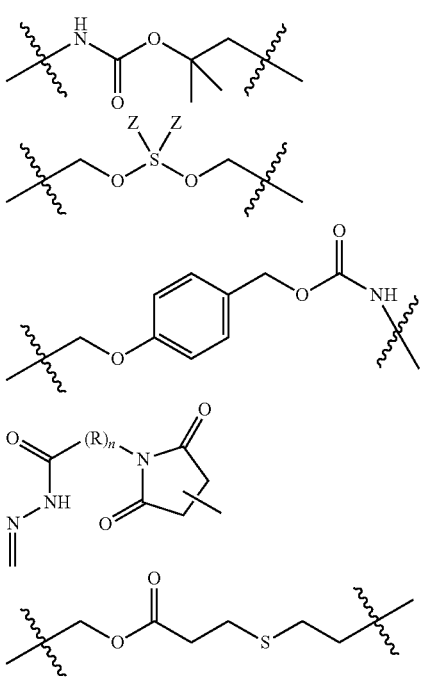

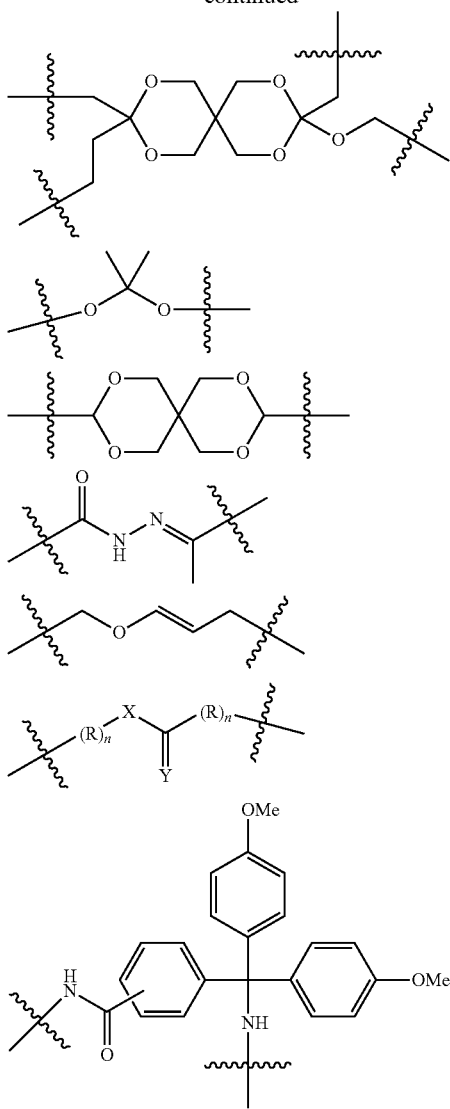

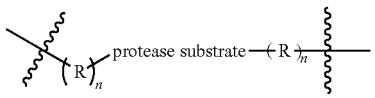

Where R and n are the same as above.

Exemplary enzymatically cleaved labile linkers include those according to the chemical structure:

Where the protease substrate is a peptide containing from 2 to 50 amino acid units, often 2 to 25 amino acid units, 2 to 15 amino acid units, 2 to 10 amino acid units, 2 to 6 amino acids, 2 to 4 amino acids, 2,3 or 4. Often, the protease substrate contains or comprises the following peptides:
-Gly-Phe-Leu-Gly-; (SEQ ID NO:1)
-Ala-Leu-Ala-Leu; (SEQ ID NO: 2)
-Phe-Arg-;
-Phe-Lys-;
-Val-Cit- (valine-citrillune);
-Val-Lys-;
-Val-Ala-;

These groups are identified and described in greater detail hereinbelow.

The cytotoxic moiety is preferably a moiety derived from an agent which exhibits cytotoxicity upon its introduction into a cell in effective amounts. These include doxorubicin, daunorubicin, carbocisplatin, mertansine, monomethylauristatin E (MME), calicheamicin, methotrexate, chlorambucil and lomaiviticin which are effective to cause cell death, including cell death of CD4 cells which have been infected with HIV. Cytotoxic moieties used in the present invention are described in greater detail herein.

In an additional aspect of the invention, a pharmaceutical composition comprises an effective amount of a bifunctional compound as described herein, optionally and preferably in combination with a pharmaceutically acceptable carrier, additive or excipient. In alternative aspects, pharmaceutical combination compositions comprise an effective amount of a bifunctional compound as described herein, in combination with at least one additional agent which is used to treat HIV (an additional anti-HIV agent).

In a further aspect of the invention, compounds according to the present invention are used to treat and/or reduce the likelihood of an HIV infection or a secondary effect of HIV (such as AIDS, ARC and related disease states or conditions which occur secondary to an HIV infection) in a patient. The method of treating and/or reducing the likelihood of an HIV infection or secondary effect of an HIV cancer comprises administering to a patient in need an effective amount of a bifunctional compound as otherwise described herein in combination with a pharmaceutically acceptable carrier, additive or excipient, optionally in further combination with at least one additional agent which is effective in treating and/or reducing the likelihood of an HIV infection, or one or more of its secondary conditions or effects.

where R is an ethylene glycol group, or a methylene group and n in this labile linker is from 0 to 10, often from 1 to 6, or 1 to 3 and where points of attachment (as indicated) are to other portions of the labile linker, a connector moiety (CON), a non-labile linker (NLL), a virus invasion cell binding moiety (VICB) or a cytotoxic moiety (CYT) as otherwise described herein;

X is O, N—$R^{AL}$ or S;

$R^{AL}$ is H or a $C_1$-$C_3$ alkyl group (often H or Me, most often H);

Y is O or S and

Z=Me, Et, iPr, tBu, Ph, each of which may be optionally substituted with one or more halogen groups (especially from three up to five Fs, preferably no more than three Fs) and where said Ph group may be further optionally substituted with a $C_1$-$C_3$ alkyl group (which may be substituted with up to three halogens, preferably F) or OMe.

Exemplary reductively cleaved moieties (by glutathione, other reductive species within the cell) include moieties according to the chemical formula:

The present invention also relates to instances in which destruction of CD4 cells which are infected with HIV (HIV+CD4 cells) may be useful to inhibit latent HIV infections from becoming active. In this aspect of the invention, destruction of HIV+CD4 cells in an HIV positive patient may be used to inhibit or more completely eradicate an HIV infection and/or reduce the likelihood of an occurrence or recurrence of HIV in a patient who is HIV positive.

The present invention also relates to a method for binding and eliminating HIV in a patient comprising administering to a patient infected with HIV, an effective amount of a bifunctional compound as otherwise described herein.

The present invention also relates to a method for binding and eliminating HIV in a patient having a latent HIV infection comprising administering to a patient infected with latent HIV an effective amount of a bifunctional compound as otherwise described herein in combination with an HIV latency activator molecule, including for example, prostratin, bradystatin 1, and related analogues as set forth in FIG. 4, hereof (see De Christopher, et al., *Nature Chemistry*, published online Jul. 15, 2012, pages 1-6), bryostatin 1, bryostatin 2, IL-7, histone deacetylase inhibitors, including zolinza (vorinostat), DNA methylation inhibitors including decogen (decitabine) and mixtures thereof.

Thus, the present invention presents unique bifunctional molecules which can operate through the bifunctional mechanisms specified above in treating HIV, including treating latent HIV infections.

The realization that viruses may exert cell and tissue tropism by attachment at highly specific sites on cell membrane receptors has encouraged investigators in the past to seek agents which would bind at the viral receptor sites of cell membranes and thus prevent binding of a specific virus to these cells.

Specifically, HIV has been shown to bind to a surface molecule known as the CD4 or T4 receptor which is present on various cells susceptible to HIV infection, including T lymphocytes and macrophages. The binding occurs via the HIV envelope protein, gp120.

Thus, it is a principal object of the present invention to provide bifunctional compounds that would act to alleviate the symptoms of AIDS by binding a bifunctional molecule which has a first terminus for binding to the gp120 envelope protein, the bifunctional molecule having a second cytotoxic terminus which causes cell death upon introduction to the cell to which the compound binds. Without being limited by way of theory, it is believed that compounds according to the present invention bind to cells to which HIV gp120 binds and/or which express gp120 cells and upon binding to gp120 containing cells, are introduced into the cell whereupon the cytotoxic moiety can cause cell death. Bifunctional compounds according to the present invention are introduced into cells by a variety of possible mechanisms including passive diffusion, endocytosis (including clathnin-mediated, caveolae-mediated and phagocytosis) and pinocytosis. These bifunctional (which term also includes multifunctional) molecules are thus generically referred to herein as "cytotoxic-drug delivering molecules targeting HIV" or (CDM-Hs).

The inventive CDM-Hs molecules are "bifunctional" in that they possess a at least one virus invasion cell binding terminus (VICB) and at least cytotoxicity terminus (CYT) connected by at least one linker (preferably at least one labile linker) and an optional connector molecule CON. The VICB is designed to bind to the HIV glycoprotein gp120 (gp120 on the viral membrane as well as gp120 displayed on infected cells). The CYT contains a cytotoxicity moiety which is designed to cause the death of any cell to which the bifunctional molecule binds, thus inhibiting and in certain cases eradicating HIV from a patient or subject in need.

In one embodiment of the invention, a bifunctional CDM-H molecule is described which is capable of delivering a population of cytotoxic agents to the HIV gp120 Env gene product, in particular, which are expressed on CD4 cells. The Env glycoprotein, a complex between gp120 and membrane-bound gp 41, is expressed on both the surface of the HIV virus and on virus-infected cells, especially CD4 cells. (Miranda. L. R.; Schaefer, B. C.; Kupfer. A.; Hu, Z. X.; Franzusoff, A. Proc. Natl. Acad. Sci. U.S.A, 2002, 99, 8031-8036). The gp120 component of Env mediates the first step in viral entry into human cells by binding the protein CD4.

According to the present invention, the CDM-H binds to gp120 Env-expressing cells, is introduced into the infected cell and causes destruction of these cells through the action of the cytotoxic moiety. Further, since CDM-Hs bind gp120 competitively with CD4, these compounds also inhibits the entry of live HIV into human T-cells. Thus, CDM-Hs have the potential to interfere with the survival of HIV through multiple complementary mechanisms, and may also function as a prophylactic, reducing the likelihood of an HIV infection or a relapse of an HIV infection. In certain embodiments according to the present invention, the CDM-Hs according to the present invention may be combined with at least one and preferably a mixture of HIV latency activator compounds to enhance therapy against HIV infection. This approach may be particularly useful for eradicating (i.e., curing) HIV infections in patients in need.

The CDM-Hs compounds of the invention represent a molecule-based rather than a peptide or protein based (although certain labile linkers may rely on peptides for protease degradation) anti-HIV strategy for targeting the virus life cycle through mutually reinforcing molecular mechanisms, inhibiting virus entry while targeting Env-expressing cells for immune recognition and clearance (cell death). In general, the CDM-Hs molecules have certain advantages over proteins from a therapeutic standpoint because of their low propensity for immunogenicity, high metabolic stability, specific HIV-infected cell targeting capability, ready large-scale production, and relatively low cost. Critically, no appreciable non-specific cytotoxicity occurs in response to the CDM-H compounds according to the present invention, thus, limiting the possibility of encountering serious side effects from the treatment therewith.

Elucidation of the molecular details governing the interactions among CDM-Hs, gp120, and cytotoxic molecules assists in optimization efforts as well as in the evaluation of this strategy in more complex biological models of HIV infection.

As stated above, the invention is directed to "bifunctional" molecules, the inventive molecules being "bifunctional" in that they possess a virus invasion cell binding (VICB) terminus and a cytotoxic moiety (CYT) connected by one or more linkers (one of which is a labile linker which degrades upon introduction into a cell to release the cytotoxicity moiety from the remaining portion of the molecule) and an optional connecting group (which is principally difunctional, but may be multifunctional) as otherwise described herein. The VICB group is designed to bind to the HIV glycoprotein gp120 (gp120 on the viral membrane as well as gp120 displayed on infected cells, generally T cells which express CD4 or CD4+ T cells). The CYT group is a cytoxic moiety capable of causing cell death upon introduction into a cell as described in detail herein.

The present invention is directed to pharmaceutical compositions comprising the above-described bifunctional molecules that can inhibit HIV entry into a target cell and/or bind to CD4+ cells while also delivering one or more cytotoxic agents to the HIV infected cells, thus inducing cell death, in a pharmaceutically acceptable carrier, additive or excipient. As additional embodiments of the invention, therefore, the inventors provide a pharmaceutical composition comprising a bifunctional molecule compound of the invention in association with a pharmaceutically acceptable carrier or excipient, adapted for use in human or veterinary medicine. Such compositions may be presented for use in conventional manner in admixture with one or more physiologically acceptable carriers or excipients. The compositions may optionally further contain one or more other therapeutic agents which may be, if desired, a different antiviral agent and preferably, an additional anti-HIV agent and/or an anticancer agent.

The bifunctional molecule compounds according to the invention may be formulated for oral, buccal, nasal, parenteral, topical or rectal administration, among others, as otherwise described herein.

In particular, the bifunctional compounds according to the invention may be formulated for injection or for infusion and may be presented in unit dose form in ampoules or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients such as other antiviral agents, including additional anti-HIV agents, latent HIV activators, anticancer agents, antimicrobial agents, or preservatives, among others.

The compositions may contain from 0.001-99% by weight of the active material, often from about 1% to about 75% by weight, about 5% to about 50% by weight, about 10% to about 50% by weight.

The invention further provides a process for preparing a pharmaceutical composition which comprises bringing a bifunctional molecule compound of the invention into association with a pharmaceutically acceptable excipient or carrier.

For administration by injection or infusion, dosages and desired drug concentrations of the disclosed pharmaceutical compositions may vary depending on the particular use, patient condition, age, drug tolerance, etc., as would be understood by one skilled in the field. Consequently, the determination of an appropriate dosage and/or route of administration is well within the skill of an ordinary practitioner, and the compounds can certainly be formulated without undue experimentation for administration in the treatment of humans, for example, using standard and well known dose-response protocols.

The amount of compound in a pharmaceutical composition of the instant invention that may be combined with the carrier materials to produce a single dosage form will vary depending upon the subject or patient the specific disease treated or use, as well as the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other CDM-Hs which may be used to treat HIV infection or a secondary effect or condition thereof or another agent such as an additional anti-HIV agent, a latent HIV activator or an anticancer agent as otherwise disclosed herein.

In one embodiment, preferred compounds according to the present invention are represented by the following chemical formula (attachment of the Cytotoxic moiety is through a labile linker which is optionally further extended with a non-labile linker as indicated:

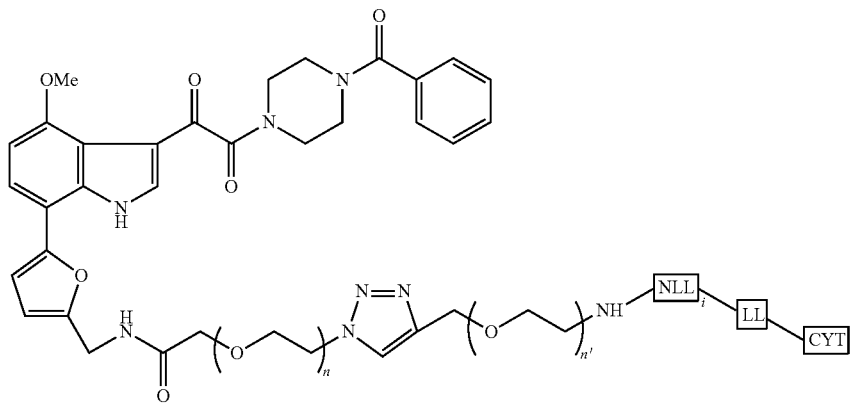

Where n and n' are each independently 2-8, often 2-6, 4-6 (2, 3, 4, 5 or 6);

i is 0 or 1;

[LL] is a labile linker according to the chemical structure:

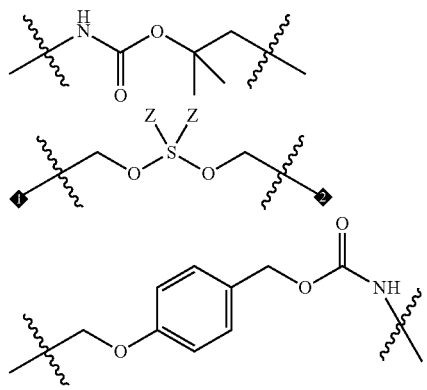

-continued

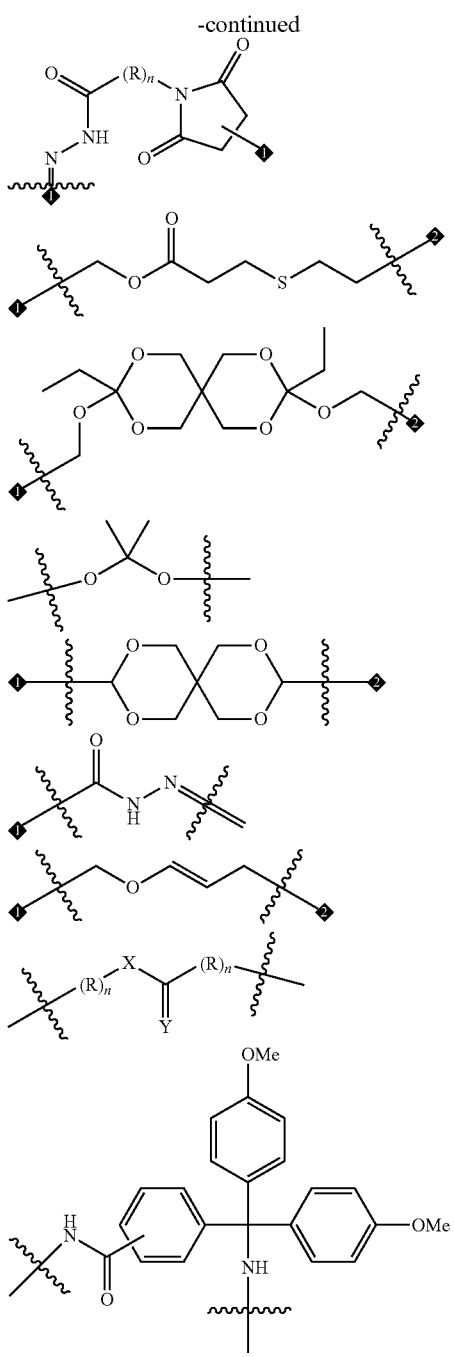

where R is an ethylene glycol group, or a methylene group and n in this labile linker is from 0 to 10, often from 1 to 6, or 1 to 3;
X is O, N—R$^{AL}$ or S;
R$^{AL}$ is H or a C$_1$-C$_3$ alkyl group (often H or Me, most often H);
Y is O or S and
Z=Me, Et, iPr, tBu, Ph, each of which may be optionally substituted with one or more halogen groups (especially from three up to five Fs, preferably no more than three Fs) and where said Ph group may be further optionally substituted with a C$_1$-C$_3$ alkyl group (which itself may be substituted with up to three halogens, preferably F) or OMe; or
[LL] is a group according to the chemical formula:

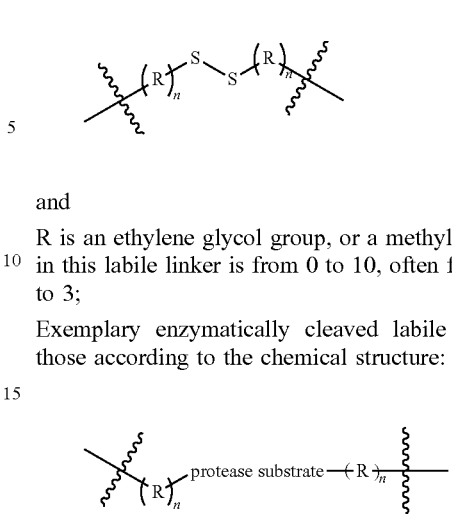

and

R is an ethylene glycol group, or a methylene group and n in this labile linker is from 0 to 10, often from 1 to 6, or 1 to 3;

Exemplary enzymatically cleaved labile linkers include those according to the chemical structure:

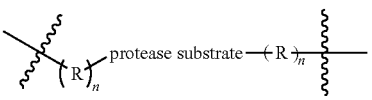

Where the protease (cathepsin) substrate is a peptide containing from 2 to 50 amino acid units, often 2 to 25 amino acid units, 2 to 15 amino acid units, 2 to 10 amino acid units, 2 to 6 amino acids, 2 to 4 amino acids, 2,3 or 4. Often, the protease substrate, above contains, comprises, consists essentially of or consists of the following peptides the point of attachment being at the distal ends of the peptide:

-Gly-Phe-Leu-Gly-; (SEQ ID NO:1)

-Ala-Leu-Ala-Leu; (SEQ ID NO: 2)

-Phe-Arg-;

-Phe-Lys-;

-Val-Cit- (valine-citrillune);

-Val-Lys-

-Val-Ala- and

Where R (above) is an ethylene glycol group, or a methylene group and n is from 0 to 10, often from 1 to 6, or 1 to 3; or

[LL] is a group according to the chemical structure:

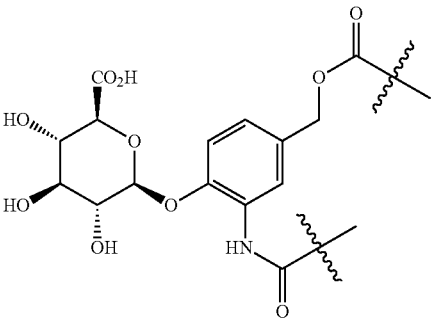 [SMILES: *C(=O)Nc1cc(COC(*)=O)ccc1O[C@@H]1O[C@H](C(=O)O)[C@@H](O)[C@H](O)[C@H]1O]

Where the points of attachment in each of the labile linkers as indicated are joined to other portions of the labile linker, a connector moiety (CON), a non-labile linker (NLL), a virus invasion cell binding moiety (VICB) or a cytotoxic moiety (CYT) as otherwise described herein;

[NLL] when present is a non-labile linker as otherwise described herein, preferably a (poly)ethylene glycol linker of from 2 to 8 ethylene glycol units, more preferably 2 to 6 ethylene glycol units or a group:

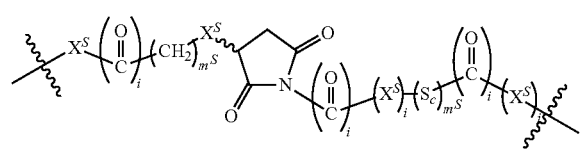
where each $X^S$ is independently S, O or N—$R^S$, preferably S;
$R^S$ is H or $C_{1-3}$alkyl, preferably H;
$S_c$ is $CH_2$; $CH_2O$; or $CH_2CH_2O$;
i is 0 or 1; and
$m^S$ is 0, 1, 2, 3, 4, 5, or 6; and
[CYT] is a group according to the chemical structure:
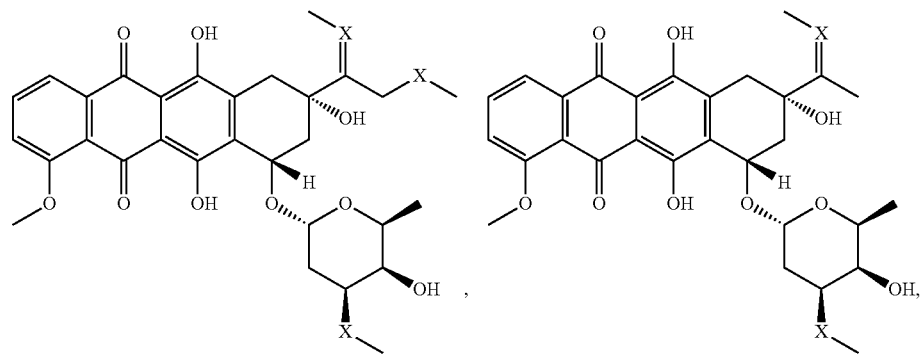
doxorubicin              daunorubicin
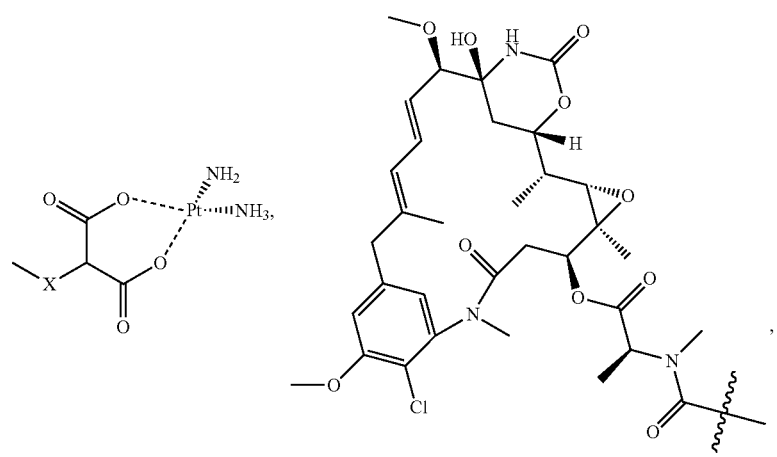
carbocisplatin              mertansine (DM1)

-continued

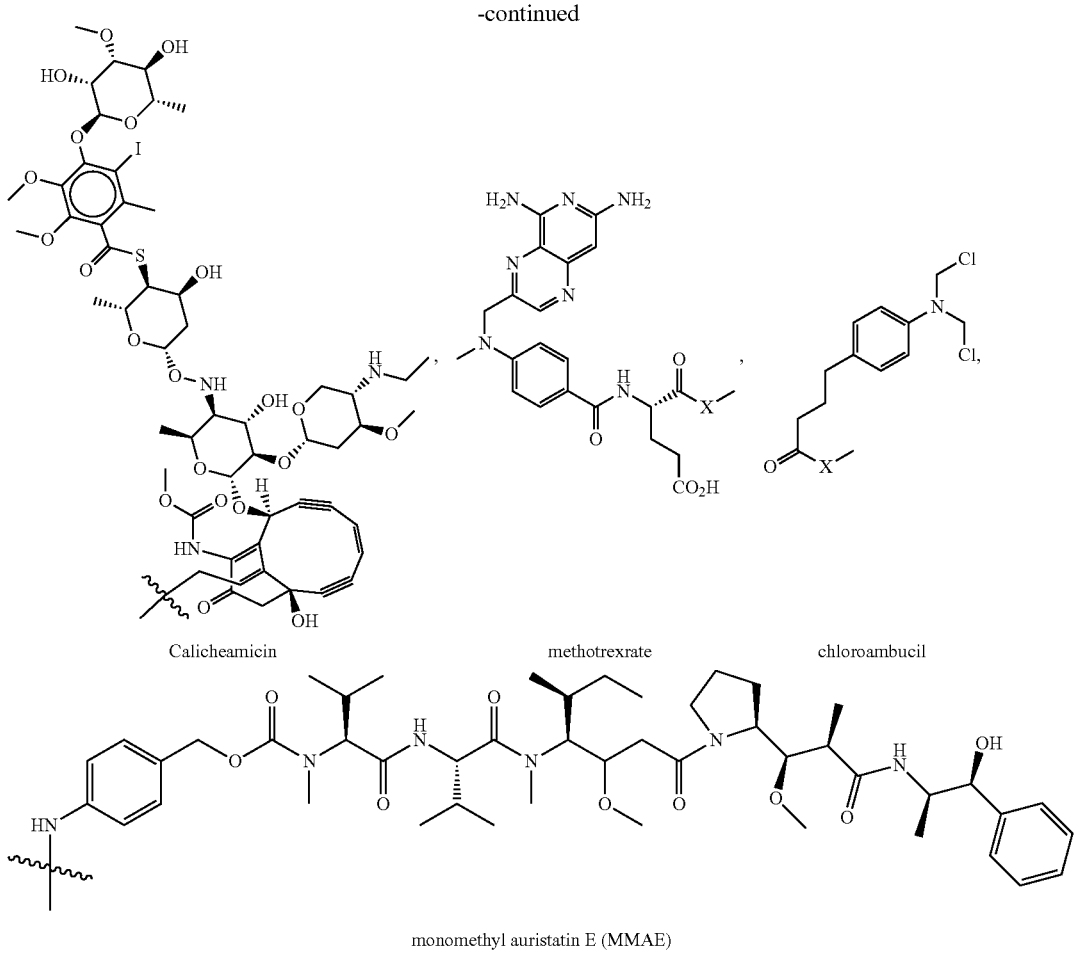

Calicheamicin methotrexrate chloroambucil monomethyl auristatin E (MMAE)

wherein X is a group which binds said CYT moiety to said labile linker,
preferably X is —NR$^{1N}$—, —NR$^{1N}$CO—, —O—, —CH$_2$—, —S—, —OCONH— or —NHCONH— where R$^{1N}$ is H or a C$_1$-C$_3$ alkyl group optionally substituted with one or two hydroxyl groups (most often H) and the symbol ⌇ signifies a chemical attachment point of the cytotoxic moiety to a labile linker (which optionally can be linked through X).
or a pharmaceutically acceptable salt, stereoisiomer, solvate or polymorph thereof.

BRIEF DESCRIPTION OF THE DRAWINGS

FIG. 2 illustrates two preferred compounds according to the present invention. These are represented as compounds 4.19 and 4.20 respectively. These compounds are presented as their pharmaceutical salts (4.19 as the formate salt and 4.20 as the ammonium acetate salt). They may also be presented readily as the free amine (as the non-salt form) or as an alternative pharmaceutically acceptable salt form.

FIG. 17 shows the raw xCelligence data of CDM-Hs 4.19 and 4.20, doxorubicin (4.18) and CD4-PE when incubated with CHO-env (gp120+) and CHO-pSv (gp120−) cells.

DETAILED DESCRIPTION OF THE INVENTION

Figure 1:
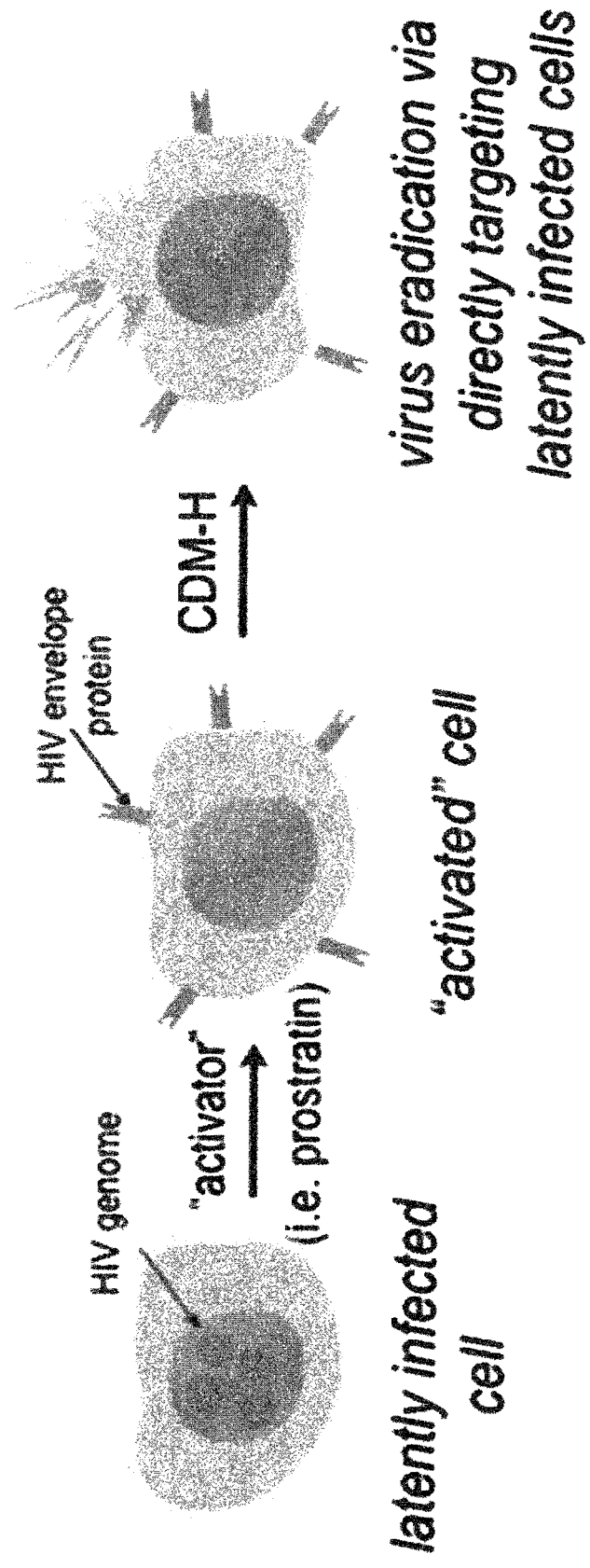
FIG. 1 illustrates a scheme of "activation-elimination" to eradicate HIV infection. Latent HIV infection is characterized by host cells possessing an integrated HIV genome, however not actively expressing HIV proteins. Various "activator" molecules, such a prostratin, bryostain 1 and analogues thereof, are known to activate the latent reservoirs, inducing host cells to express the HIV genome. Once activated, CDM-Hs can direct a cytotoxic response, leading to HIV-infected cell death.
Figure 3:
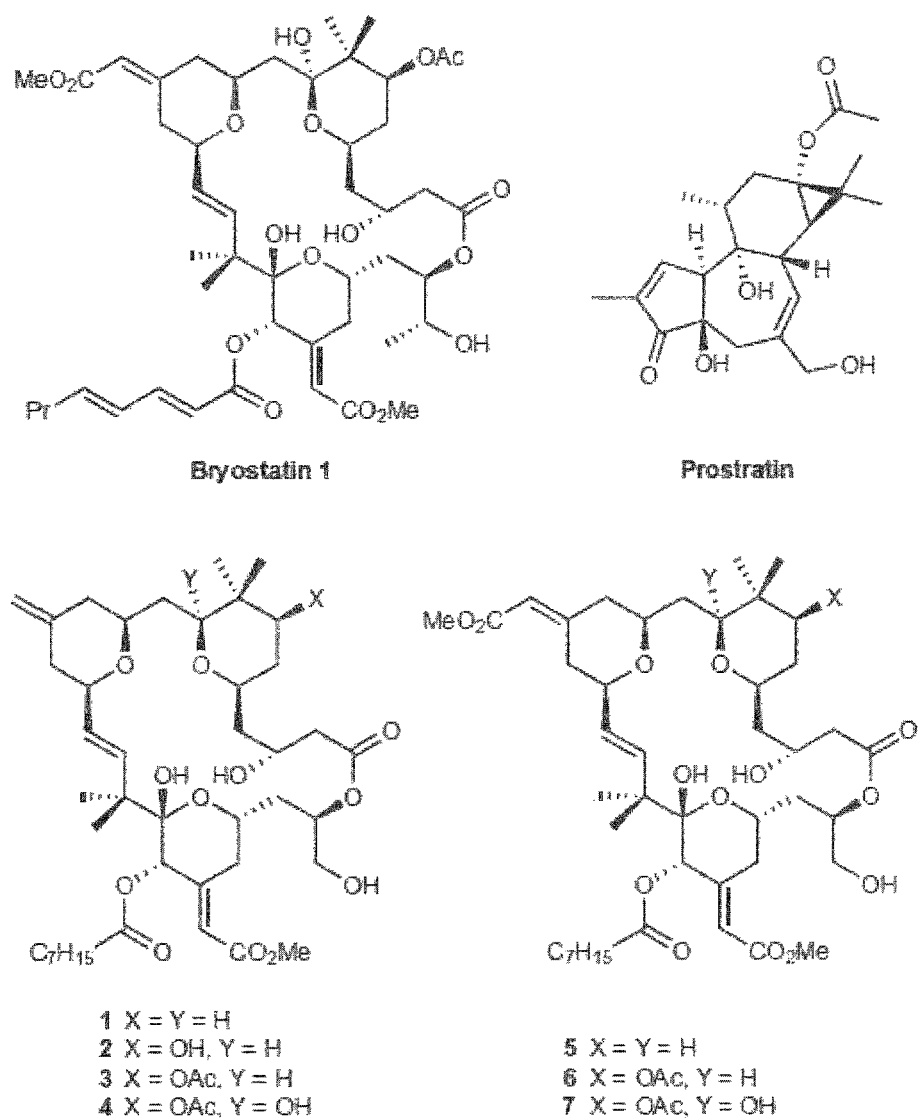
FIG. 3 shows a number of latent HIV activators including prostratin, bryostatin 1 and analogues of bryostatin 1 (compounds 1-7) as indicated.

The following terms are used to describe the present invention. In instances where a term is not specifically defined herein, that term is given an art-recognized meaning by those of ordinary skill applying that term in context to its use in describing the present invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers (including labile linkers) and connector molecules and variables associated with same, among others, are described and chosen to provide stable compounds which may be isolated and further processed into pharmaceutical composition.

"Alkyl" refers to a fully saturated monovalent radical containing carbon and hydrogen, and which may be cyclic, branched or a straight chain (and which may be optionally substituted). Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclo-propylmethyl, cyclobutyl, cyclopentyl, cyclopentylethyl, cyclohexylethyl and cyclohexyl, among others. Preferred alkyl groups are $C_1$-$C_6$ or $C_1$-$C_3$ alkyl groups.

"Aryl" or "aromatic", in context, refers to a substituted (as otherwise described herein) or unsubstituted monovalent aromatic radical having a single ring (e.g., benzene or phenyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others.

Alternative aryl and heteroaryl groups according to the present invention preferably include, for example, phenyl, naphthyl, pyridyl (2-, 3- or 4-pyridyl group), thiazolyl (2-, 4- or 5-thiazole), isothiazolyl, oxazolyl (2-, 4- or 5-oxazole), isoxazolyl, furanyl (2- or 3-furan) or thiophenyl (2- or 3-thiophene). Monocyclic and bicyclic aryl and heteroayl groups are as otherwise described herein.

In alternative embodiments, preferred heteroaryl groups (for Arene 2) are 5- or 6-membered aryl or heteroaryl groups are according to the chemical structure:

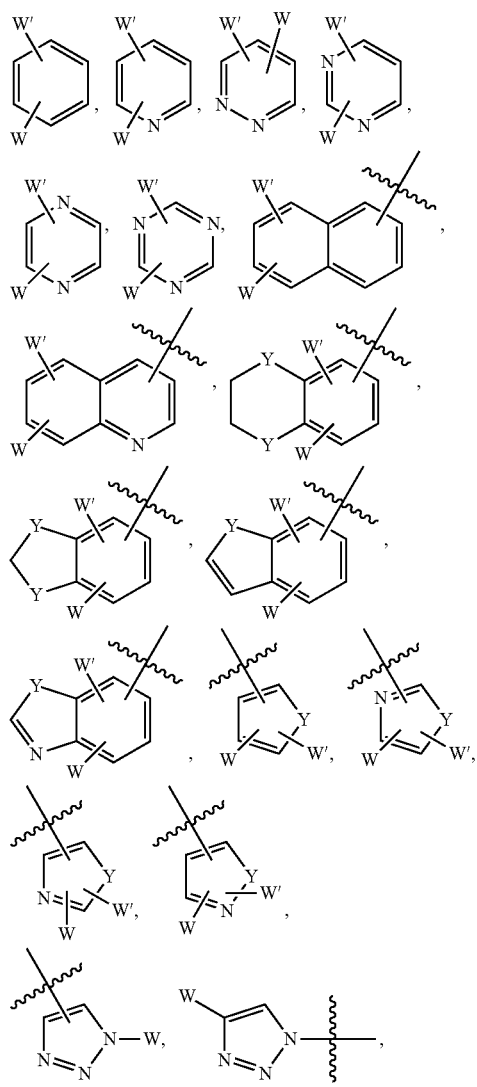

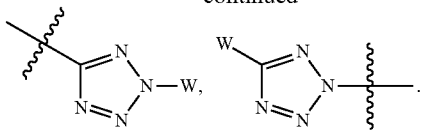

Where W and W' are each independently H, —(CH$_2$)$_n$OH, —(CH$_2$)$_n$COOH, —(CH$_2$)$_n$O—(C$_1$-C$_6$ alkyl), —(CH$_2$)$_n$C(O)—(C$_1$-C$_6$ alkyl), —(CH$_2$)$_n$—NR$_1$R$_2$, —(CH$_2$)$_n$NHC(O)—R$_1$, —(CH$_2$)$_n$C(O)—NR$_1$R$_2$, —(CH$_2$O)$_n$H, (OCH$_2$)$_n$NR$_1$R$_2$, (OCH$_2$)$_n$NR$_1$R$_2$, (OCH$_2$)$_n$CONR$_1$R$_2$, (OCH$_2$)$_n$CO$_2$R$_1$, —(CH$_2$O)$_n$COOH, C$_1$-C$_6$ alkyl, —(CH$_2$O)$_n$O—(C$_1$-C$_6$ alkyl), —(CH$_2$O)$_n$C(O)—(C$_1$-C$_6$ alkyl), —(OCH$_2$)$_n$OR$_1$, —(OCH$_2$)$_n$NHC(O)—R$_1$, —(CH$_2$O)$_n$C(O)—NR$_1$R$_2$, NO$_2$, CN, halogen (F, Cl, Br, I, preferably F or Cl) or an aryl or heteroaryl group, preferably a monocyclic aryl or heteroaryl group which itself is optionally substituted (including an optionally substituted benzoyl or benzyl group), or a

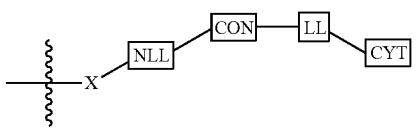

group in certain preferred embodiments, only one of W and W' is a

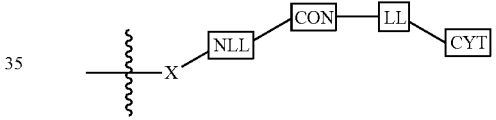

group);
Where X is —NR$^{1N}$—, —NR$^{1N}$CO—, —O—, —CH$_2$—, —S—, —OCONH— or —NHCONH—;
NLL is a non-labile linker;
LL is a labile linker which is cleavable upon entry of the compound into a cell;
CON is a connector moiety which connects said non-labile linker (NLL) with said labile-linker (LL);
CYT is a cytotoxic moiety which is capable of causing cell death upon entry of the compound into a cell;
R$^{1N}$ is H or a C$_1$-C$_3$ alkyl group optionally substituted with one or two hydroxyl groups (most often H);
R$_1$ and R$_2$ are each independently H or a C$_1$-C$_6$ alkyl group; Y is O, S or N—R, where R is H or a C$_1$-C$_3$ alkyl group; and Each n is independently 0, 1, 2, 3, 4, 5, or 6 (preferably 0 or 1).

In still other embodiments, preferred aryl or heteroaryl groups (Arene 1) include those which are substituted according to the chemical structures:

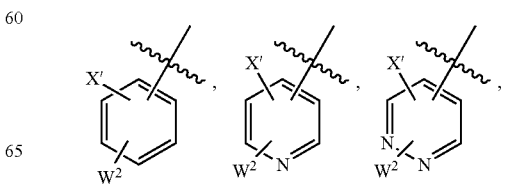

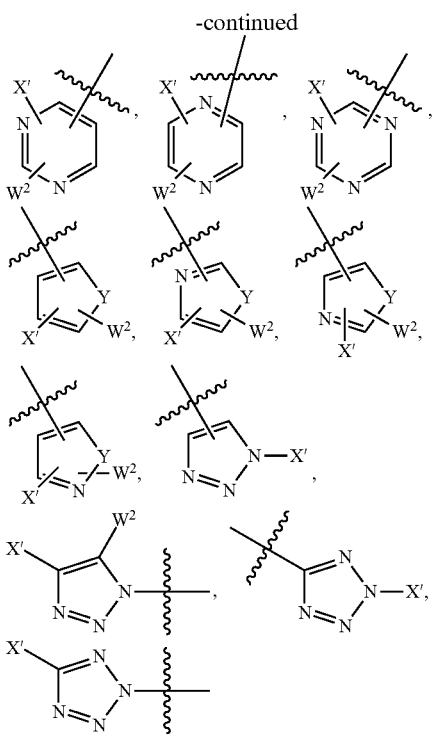

where $W^2$ is H, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—$R_1$, —$(CH_2)_nC(O)$—$NR_1R_2$, —$(CH_2O)_nH$, —$(CH_2O)_nCOOH$, $C_1$-$C_6$ alkyl, —$(CH_2O)_n$O—$(C_1$-$C_6$ alkyl), —$(CH_2O)_nC(O)$—$(C_1$-$C_6$ alkyl), —$(CH_2O)_nNHC(O)$—$R_1$, —$(CH_2O)_nC(O)$—$NR_1R_2$, $NO_2$, CN or halogen (preferably F or Cl);

$R_1$ and $R_2$ are each independently H or a $C_1$-$C_6$ alkyl group;
X' is H, O—$C_1$-$C_6$ alkyl (preferably OMe), halogen (F, Cl, Br) or a

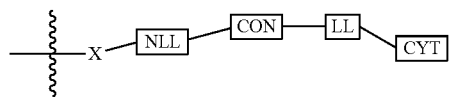

group;
Where X is —$NR^{1N}$—, —$NR^{1N}CO$—, —O—, —$CH_2$—, —S—, —OCONH— or —NHCONH—;
NLL is a non-labile linker;
LL is a labile linker which is cleavable upon entry of the compound into a cell;
CON is a connector moiety which connects said non-labile linker (NLL) with said labile-linker (LL);
CYT is a cytotoxic moiety which is capable of causing cell death upon entry of the compound into a cell;
$R^{1N}$ is H or a $C_1$-$C_3$ alkyl group optionally substituted with one or two hydroxyl groups (most often H); and
Each n is independently 0, 1, 2, 3, 4, 5, or 6 (preferably 0 or 1), The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), ester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). The term "substituted" shall also mean within its context of use alkyl, alkoxy, halogen, amido, carboxamido, keto, carboxy, ester, keto, nitro, cyano and amine (especially including mono- or di-$C_1$-$C_6$ alkyl substituted amines which may be optionally substituted with one or two hydroxyl groups). In certain embodiments preferred substituents will include for example, —NH—, —NHC(O)—, —O—, —$(CH_2)_m$— (m and n are at least 1 as otherwise described herein), —S—, —S(O)—, $SO_2$— or —NH—C(O)—NH—, —$(CH_2)_nOH$, —$(CH_2)_nCOOH$, $C_1$-$C_6$ alkyl, —$(CH_2)_nO$—$(C_1$-$C_6$ alkyl), —$(CH_2)_nC(O)$—$(C_1$-$C_6$ alkyl), —$(CH_2)_nNHC(O)$—$R_1$, —$(CH_2)_nC(O)$—$NR_1R_2$, —$(CH_2O)_nOH$, —$(CH_2O)_n$COOH, $C_1$-$C_6$ alkyl, —$(OCH_2)_nO$—$(C_1$-$C_6$ alkyl), —$(OCH_2)_nC(O)$—$(C_1$-$C_6$ alkyl), —$(OCH_2)_nNHC(O)$—$R_1$, —$(CH_2O)_nC(O)$—$NR_1R_2$, $NO_2$, CN or halogen (F, Cl, Br, I, preferably F or Cl), depending on the context of the use of the substituent.

Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for treating and/or reducing the likelihood of HIV infections or the secondary effects of HIV infections, especially including AIDS and/or ARC.

The term "effective" is used herein, unless otherwise indicated, to describe an amount of a compound or composition which, in context, is used to produce or effect an intended result, whether that result relates to the inhibition of the effects of a toxicant on a subject or the treatment of a subject for secondary conditions, disease states or manifestations of exposure to toxicants as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for HIV infection or having an HIV infection, including a latent HIV infection, including improvement in the condition through lessening or suppression of titers of HIV or at least one symptom of HIV, prevention or delay in progression of the disease, prevention or delay in the onset of disease states or conditions which occur secondary to HIV, including AIDS or ARC, among others, including the eradication of HIV. Treatment, as used herein, encompasses both prophylactic and therapeutic treatment. The term "prophylactic" when used, means to reduce the likelihood of an occurrence or the severity of an occurrence within the context of the treatment of HIV, as otherwise described hereinabove.

The term "human immunodeficiency virus" or "HIV" shall be used to describe human immunodeficiency viruses 1 and 2 (HIV-1 and HIV-2), the growth or replication of which may be inhibited or disease states of which may be treated using one or more methods according to the present invention. Viruses which may be treated according to the present invention include, for example, human immunodeficiency viruses 1 and 2 (HIV-1 and HIV-2), among others. The term HIV includes mutant strains of HIV including "drug resistant" or "multiple drug resistant" strains of the HIV virus which have mutated to be resistant to one or more clinically approved anti-HIV agents, including, in particular, HIV strains which are resistant to one or more NRTI compounds and/or NNRTI compounds. Exemplary HIV drug resistant strains which may be effectively treated using compounds according to the present invention include the following, among others: (defined by their reverse transcriptase or RT mutation)—XXBRU, K65R, Y115F, F116Y, Q151M, M184V, L74V, V75T, 4XZT, T215Y, K103N, T215Y/M184V, 5705-72, 488-101, C910-6, LA1M184V, G910-6 L100I, K101E, K103N, V106A, D110E, V179D, Y181C, D185E, D186E, Y188H, G190E, E138K, M41L, D67N, K70R, T215Y/F, K219Q/E, Y181C, K103N, L100I, Y188C/H, among others, including HIV-1 isolates JR-FL, ADA, HXBc2, SF162 and BaL, among others.

The term "HIV latency" is used to describe the ability of HIV to lie dormant within a patient's cells, in particular, CD4-positive T cells and form one or more viral reservoirs. In HIV, proviral latency in specific long-lived cell types is the basis for viral reservoirs, which are characterized by the persistence or longevity of the latent virus in the infected cells. In HIV latency, the presence of replication-competent HIV in resting CD4-positive T cells, allows the virus to persist for years without evolving despite prolonged exposure to antiretroviral drugs. This latent reservoir of HIV (latent HIV) may explain the inability of traditional antiretroviral treatment to eradicate or cure the HIV infection in a patient. The present invention serves to destroy cells (CD4-positive cells) which harbor viral reservoirs and reduce the likelihood that an active HIV flareup will occur, as well as provide an actual cure for HIV through eradication of HIV in certain instances. The present invention serves to reduce, inhibit and/or eliminate the HIV viral reservoirs and HIV proviruses in a patient's cells, especially CD4-positive cells and reduce the likelihood that an active HIV flareup or infection will occur in the future. While not being limited by way of theory, it is believed that the compounds and methods according to the present invention reduce, inhibit and/or eliminate/eradicate latent HIV (latent HIV reservoirs) and/or HIV proviruses through cell death of CD4 positive cells, thus reducing the likelihood that latent HIV will become an active HIV infection. The compounds act by releasing cytotoxic agents after introduction into a cell which results in cell death and inhibition of the ability of HIV to replicate. This inhibition results in the latent HIV or proviral HIV residing in cells being destroyed and/or acted upon by a co-administered anti-HIV agent which serves to inhibit HIV. The result of the present method is that the latent HIV is reduced, inhibited and/or eliminated and in certain instances an actual cure of HIV can be effected because latent HIV, as well as active HIV, is eliminated from the patient, resulting in no further infection.

HIV binds to the outer surface of CD4+ cells, enters the cells, and then remains hidden and protected from the other immune system cells. Safely inside the cell, the virus duplicates its RNA. The new viral DNA is integrated into the host cell's DNA where it governs the production of new HIV virions. The new virions leave the host cell to infect other cells, and the host CD4+ cell dies. The body produces about 10 billion new virions daily, and the immune system destroys and removes all but about 100 million of them, which are infectious. An equal number of CD4+ cells are produced and destroyed by the virions, creating a balance of power struggle between the virus and the CD4+ cells.

The HIV life cycle in its active form, requires specific enzymes, which serve as targets for traditional anti-HIV drug therapy:

Reverse transcriptase helps create DNA copies of HIV's RNA. Nucleoside and non-nucleoside antiretroviral drugs block reverse transcriptase, preventing HIV from copying its RNA into DNA.

Integrase helps integrate the viral DNA into the host cell's DNA. Integrase is a potential target for drug therapy, and scientists are hoping to find a way to block it to prevent viral DNA from being integrated into the host cell's DNA.

Protease helps assemble the new virions. Protease inhibitors prevent protease from performing this function.

In some cases, HIV does not start replicating immediately upon entering a new host cell. Once the DNA enters the host cell's genome, HIV can persist for years inside the body without causing the symptoms that define AIDS. But even at this stage (which is called latency), the virus can still be transmitted to others. Latency is perhaps one of the greatest challenges to finding a cure or vaccine for AIDS and is the principal reason why people with AIDS must take antiretroviral drugs for life. The present invention serves to reduce the HIV viral reservoirs and HIV proviruses in a patient's cells, especially CD4-positive cells and reduce the likelihood that an active HIV flareup or infection will occur. Compounds according to the present invention reduce, inhibit and/or eliminate latent HIV reservoirs and/or HIV proviruses alone or in combination with at least one additional anti-HIV agent and/or one or more latent HIV activators, thus reducing, inhibiting and/or eliminating latent HIV and thereby reducing the likelihood that latent HIV will become an active HIV infection.

The term "latent HIV activator" is used to describe one or more compounds which activates latent HIV into a more active state. HIV activators which may be used in combination with CDM-Hs according to the present invention include, prostratin, bradystatin 1, and related analogues as set forth in FIG. 4, hereof (see De Christopher, et al., *Nature Chemistry*, published online Jul. 15, 2012, pages 1-6), bryostatin 1, bryostatin 2, IL-7, histone deacetylase inhibitors, including zolinza (vorinostat), DNA methylation inhibitors including decogen (decitabine) and mixtures thereof. The HIV activators are used to upregulate HIV from a latency state to a more active state such that the active HIV express gp120 on the surface of an HIV infected CD4 cell (HIV positive CD4). HIV activators, when administered to a patient or subject are preferably administered as a mixture of HIV activators, as described above.

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharyngeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria:
T-cells have dropped below 200 or the patient has had at least one of the following defining illnesses—

Brain Toxoplasmosis
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent
Progressive multifocal leukoencephalopathy
*Salmonella* septicemia, recurrent
Wasting syndrome due to HIV The term "introduce" is used to describe the uptake by a HIV-infected CD4 cell of CDM-Hs which have become bound to the surface of HIV-infected CD4 cell at the gp120 envelope protein on the cell surface. CDM-Hs may become internalized in the cell, after which the cytotoxic moiety CYT may be released from the CDM-Hs, resulting in the death of the HIV infected CD4 cells. CDM-Hs become internalized into a HIV-infected CD4 cell after binding through one or more of a variety of mechanisms including, but not limited to, passive diffusion, endocytosis (including clathnin-mediated, caveolae-mediated and phagocytosis) and pinocytosis The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain aspects of the present invention, one or more of the bifunction CDM-H compounds described above, are coadministered in combination with at least one additional anti-HIV agent as otherwise described herein in a cocktail for the treatment of HIV infections and/or a latent HIV activator compound/composition as otherwise described herein. In particularly preferred aspects of the invention, the co-administration of compounds results in synergistic anti-HIV activity of the therapy, especially including inhibition and/or eradication of latent HIV.

The term "additional anti-HIV agent" shall mean a traditional anti-HIV agent (ie., a non-bifunctional CDM-H compound as otherwise described herein) which may be co-administered to a patient along with ARM-HI compounds according to the present invention in treating a patient for HIV. Such compounds include, for example, agents such as nucleoside reverse transcriptase inhibitors (NRTI), non-nucleoside reverse transcriptase inhibitors, protease inhibitors and fusion inhibitors. Exemplary compounds include, for example, Amprenivir, Abacavir, Acemannan, Acyclovir, AD-439, AD-519, Adefovir dipivoxil, Alpha Interferon, Ansamycin, 097, AR 177, Beta-fluoro-ddA, BMS-232623 (CGP-73547), BMS-234475 (CGP-61755), CI-1012, Cidofovir, Curdlan sulfate, Cytomegalovirus Immune globin, Ganciclovir, Dideoxyinosine, DMP-450, Efavirenz (DMP-266), EL10, Famciclovir, FTC, GS 840, HBY097, Hypericin, Recombinant Human Interferon Beta, Interferon alfa-n3, Indinavir, ISIS-2922, KNI-272, Lamivudine (3TC), Lobucavir, Nelfinavir, Nevirapine, Novapren, Peptide T Octapeptide Sequence, Trisodium Phosphonoformate, PNU-140690, Probucol, RBC-CD4, Ritonavir, Saquinavir, Valaciclovir, Virazole Ribavirin, VX-478, Zalcitabine, Zidovudine (AZT), Tenofovir diisoproxil fumarate salt, Combivir, Abacavir succinate, T-20), AS-101, Bropirimine, CL246, EL10, FP-21399, Gamma Interferon, Granulocyte Macrophage Colony Stimulating Factor (GM-CSF), HIV Core Particle Immunostimulant, Interleukin-2 (IL-2), Immune Globulin Intravenous, IMREG-1, IMREG-2, Imuthiol Diethyl Dithio Carbamate, Alpha-2 Interferon, Methionine-Enkephalin, MTP-PE (Muramyl-Tripeptide), Granulocyte Colony Stimulating Factor (GCSF), Remune, rCD4 (Recombinant Soluble Human CD4-IgG), rCD4-IgG Hybrids, Recombinant Soluble Human CD4, Interferon Alfa 2a, SK&F1-6528, Soluble T4, Thymopentin, Tumor Necrosis Factor (TNF), AK602, Alovudine, Amdoxovir, AMD070, Atazanavir (Reyataz), AVX754 (apricitabine), Bevirimat, BI-201, BMS-378806, BMS-488043, BMS-707035, C31G, Carbopol 974P, Calanolide A, Carrageenan, Cellulose sulfate, Cyanovirin-N, Darunavir, Delavirdine, Didanosine (Videx), Efavirenz, Elvucitabine, Emtricitabine, Fosamprenavir (Lexiva), Fozivudine tidoxil, GS 9137, GSK-873,140 (aplaviroc), GSK-364735, GW640385 (brecanavir), HG0004, HGTV43, INCB9471, KP-1461, Lopinavir, Mifepristone (VGX410), MK-0518, PPL-100, PRO 140, PRO 542, PRO 2000, Racivir, SCH-D (vicriviroc), SP01A, SPL7013, TAK-652, Tipranavir (Aptivus), TNX-355, TMC125 (etravirine), UC-781, UK-427,857 (Maraviroc), Valproic acid, VRX496, Zalcitabine, Valganciclovir, Clindamycin with Primaquine, Fluconazole Pastille, Nystatin Pastille, Eflornithine, Pentamidine, Isethionate, Trimethoprim, Trimethoprim/sulfa, Piritrexim, Pentamidine isethionate, Spiramycin, Intraconazole-R51211, Trimetrexate, Daunorubicin, Recombinant Human Erythropoietin, Recombinant Human Growth Hormone, Megestrol Acetate, Testosterone, Aldesleukin (Proleukin), Amphotericin B, Azithromycin (Zithromax), Calcium hydroxyapatite, Doxorubicin, Dronabinol, Entecavir, Epoetin alfa, Etoposide, Fluconazole, Isoniazid, Itraconazole (Sporanox), Megestrol, Paclitaxel (Taxol), Peginterferon alfa-2, Poly-L-lactic acid (Sculptra), Rifabutin (Mycobutin), Rifampin, Somatropin and Sulfamethoxazole/Trimethoprim. Preferred anti-HIV compounds for use in the present invention include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof The term "pharmaceutically acceptable salt" is used throughout the specification to describe a salt form of one or more of the compounds herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be particularly preferred as neutralization salts of carboxylic acid containing compositions according to the present invention. The term "salt" shall mean any salt consistent with the use of the compounds according to the present invention. In the case where the compounds are used in pharmaceutical indications, including the treatment of HIV infections, the term "salt" shall mean a pharmaceutically acceptable salt, consistent with the use of the compounds as pharmaceutical agents.

The term "cytotoxicity terminus" or "cytotoxic agent moiety" (CYT within the general formula of compounds according to the present invention) is used to describe that portion of a CDM-Hs compound according to the present invention which comprises at least one cytotoxic agent which exhibits cytotoxicity within the patient. The terms "cytotoxic moiety" or "HIV cytotoxic moiety" or HIV cell infected cytotoxicity" are used synonymously to describe a small molecule moiety which exhibits cytotoxic activity against a cell which has been infected with HIV such that when the viral infected cell binding moiety

VICB binds to gp120 protein and/or CD4 on the infected cell, the CDM-Hs compound and/or the cytotoxic agent itself will enter the infected cell and promote cellular death, resulting in the inhibition of the HIV infection. Exemplary cytoxic agents from which the CYT group in CDM-Hs according to the present invention are derived include doxorubicin, daunorubicin, carbocisplatin, mertansine, monomethylauristatin E (MME), calicheamicin, methotrexate and chlorambucil, which are effective to cause cell death, including cell death of CD4 cells which have been infected with HIV. These cytotoxicity agents are linked in the CDM-Hs compounds as represented below (at one or more of the X variables or points of attachment in each compound as indicated below).

doxorubicin

, daunorubicin

-continued

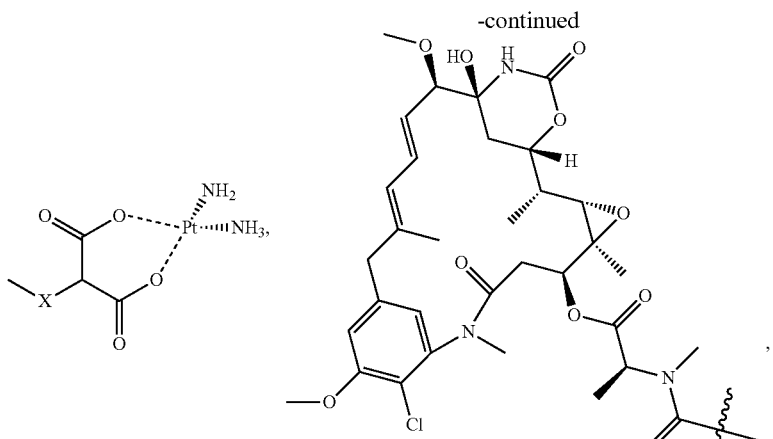

carbocisplatin    mertansine (DM1)

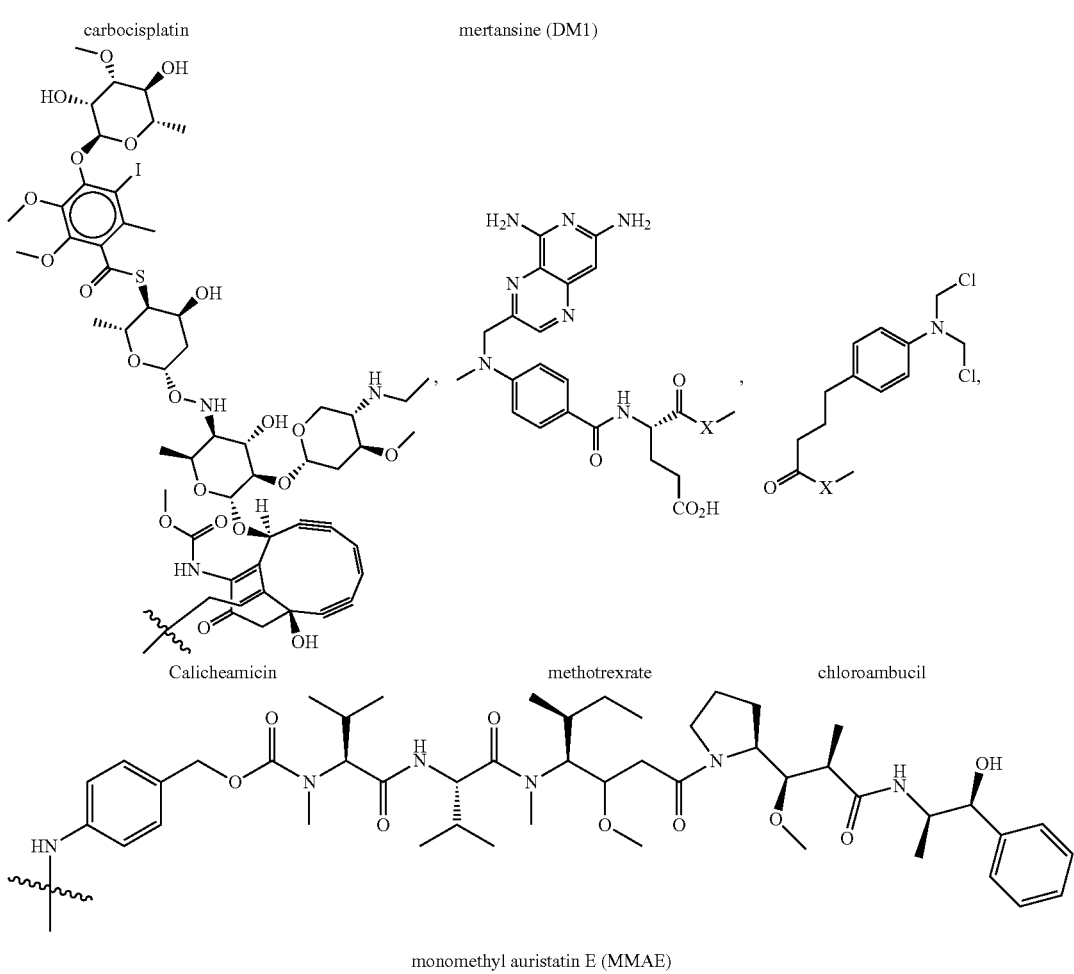

Calicheamicin    methotrexrate    chloroambucil monomethyl auristatin E (MMAE)

wherein X is a group which binds said CYT moiety to a labile linker, preferably X is $-NR^{1N}-$, $-NR^{1N}CO-$, $-O-$, $-CH_2-$, $-S-$, $-OCONH-$ or $-NHCONH-$ where $R^{1N}$ is H or a $C_1$-$C_3$ alkyl group optionally substituted with one or two hydroxyl groups (most often H) and the symbol ⌇ signifies a chemical attachment point of the cytotoxic moiety to a labile linker (which optionally can be linked through X).

Preferred cytotoxicity moieties which are including in CDM-Hs according to the present invention include doxorubicin and chlorambucil.

The term "viral invasion cell binding terminus" ("VICB") (also referred to as target binding terminus or TBT) is used to described that portion of a compound according to the present invention which comprises at least one small molecule or moiety which can bind specifically to or is capable of binding to gp120 envelope protein on HIV virus or a cell surface of CD4 cells which are infected with HIV (HIV+) in said patient.

VICB groups include those which are found in bifunctional compounds having the following chemical structure:

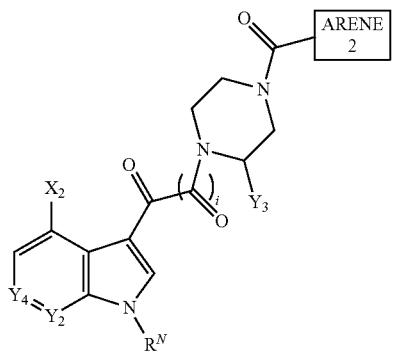

Where $Y_2$ is N or a C—$R^Y$ group;
$Y_3$ is H or a $C_1$-$C_3$ alkyl group (disposed out of or into the plane, preferably out of the plane on the chiral carbon), preferably H or $CH_3$;
$Y_4$ is C—H or N;
$R^Y$ is H, $C_1$-$C_6$ alkyl, O—($C_1$-$C_6$ alkyl), a halogen (preferably F, Br or Cl) or an aryl or heteroaryl group including a

ARENE 1 group as defined herein which is optionally substituted with a

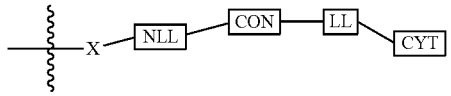

group;
Where X is —$NR^{1N}$—, —$NR^{1N}CO$—, —O—, —$CH_2$—, —S—, —OCONH— or —NHCONH—;
NLL is a non-labile linker as described herein;
LL is a labile linker which is cleavable upon entry of the compound into a cell and is optionally linked to [CON] through a second non-labile linker [NLL];
CON is a connector moiety which, when present, connects the labile-linker (LL) to the cytotoxicity moiety CYT and to the optional non-labile linker;
CYT is a cytotoxic moiety which is capable of causing cell death upon entry of the compound into a cell;
$R^{1N}$ is H or a $C_1$-$C_3$ alkyl group optionally substituted with one or two hydroxyl groups (most often H);
$X_2$ is H, O—$C_1$-$C_6$ alkyl (preferably OMe), halogen (F, Cl, Br) or a

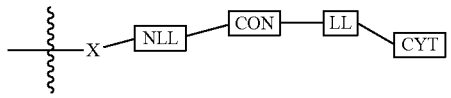

group as described above;

ARENE 2 is an optionally substituted aryl or heteroaryl group which is further optionally substituted with a

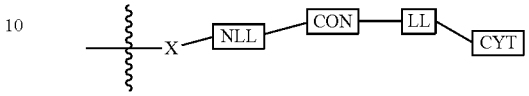

group as described above;
Where one or more of $R^Y$, $X_2$ or Arene 2 is substituted with said

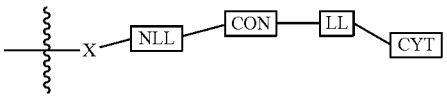

group; and
i is 0 or 1.
Preferred VICB groups include those which are otherwise disclosed herein wherein said VICB group is connected to at least one

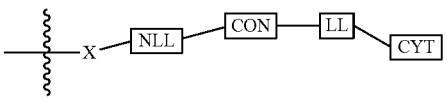

group as otherwise disclosed herein. Other embodiments of the VICB moiety used in compounds according to the present invention are as otherwise described herein.
The term "linker" refers to a chemical entity connecting a VICB moiety to a cytotoxicity moiety (CYT) terminus, optionally through a connector moiety (CON). The linker may be a labile linker (LL) which directly links the VICB moiety to the CYT moiety, or alternatively, often the labile linker links the CYT moiety through a non-labile linker (NLL) and/or a connector (CON) moiety. Noted here is the fact that the labile linker can itself contain components which are non-labile linkers, or the non-labile linker can contain one or more CON groups before being linked to a labile linker group. The linker (whether constructed as a labile linker LL alone or a LL linked to a connector CON moiety and/or a non-labile linker) ranges in length from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers (NLL or LL) which are based upon or include ethylene glycol units are between 2 and 100 glycol units in length, but those which are between 2 and 14 glycol units or 4 and 8 glycol units in length may be preferred. By having a linker with a length as otherwise disclosed herein, the VICB moiety and the CYT moiety may be chemically situated to advantageously take advantage of the biological activity of compounds according to the present invention which bind to HIV envelope protein gp120 (gp120), are introduced into HIV infected CD4 cells and release the CYT moiety within the cell to promote cell death. The selection of a linker component is based on its documented properties of biocompatibility, solubility in aqueous and organic media, and low immunogenicity/antigenicity.

Labile linkers pursuant to the present invention include any linker which may be readily cleaved upon introduction of the CDM-Hs into the cell through any one of a several cellular mechanisms. These labile linkers include hydrolytically labile (acid labile) linkers, reductively labile linkers (principally disulfide linkers which are reductively cleaved by intracellular glutathione or other disulfide reducing agent) and enzymatically labile linkers (protease substrates). These labile linkers are preferably represented by the chemical structures:

where R is an ethylene glycol group, or a methylene group and n in this labile linker is from 0 to 10, often from 1 to 6, or 1 to 3 and where points of attachment (as indicated) are to other portions of the labile linker, a connector moiety (CON), a non-labile linker (NLL), a virus invasion cell binding moiety (VICB) or a cytotoxic moiety (CYT) as otherwise described herein;

X is O, N—$R^{AL}$ or S;

$R^{AL}$ is H or a $C_1$-$C_3$ alkyl group (often H or Me, most often H);

Y is O or S and

Z=Me, Et, iPr, tBu, Ph, each of which may be optionally substituted with one or more halogen groups (especially from three up to five Fs, preferably no more than three Fs) and where said Ph group may be further optionally substituted with a $C_1$-$C_3$ alkyl group (which itself may be substituted with up to three halogens, preferably F) or OMe.

Exemplary reductively cleaved moieties (by glutathione, other reductive species within the cell) include moieties according to the chemical formula:

and

R is an ethylene glycol group, or a methylene group and n in this labile linker is from 0 to 10, often from 1 to 6, or 1 to 3 and where points of attachment (as indicated) are to other portions of the labile linker, a connector moiety (CON), a non-labile linker (NLL), a virus invasion cell binding moiety (VICB) or a cytotoxic moiety (CYT) as otherwise described herein.

Exemplary enzymatically cleaved labile linkers include those according to the chemical structure:

Where the protease (cathepsin) substrate is a peptide containing from 2 to 50 amino acid units, often 2 to 25 amino acid units, 2 to 15 amino acid units, 2 to 10 amino acid units, 2 to 6 amino acids, 2 to 4 amino acids, 2,3 or 4. Often, the protease substrate, above contains, comprises, consists essentially of or consists of the following peptides the point of attachment being at the distal ends of the peptide:
-Gly-Phe-Leu-Gly-; (SEQ ID NO:1)
-Ala-Leu-Ala-Leu; (SEQ ID NO: 2)
-Phe-Arg-;
-Phe-Lys-;
-Val-Cit- (valine-citrillune);
-Val-Lys-
-Val-Ala- and
Where R (above) is an ethylene glycol group, or a methylene group and n is from 0 to 10, often from 1 to 6, or 1 to 3 and where points of attachment (as indicated) are joined to other portions of the labile linker, a connector moiety (CON), a non-labile linker (NLL), a virus invasion cell binding moiety (VICB) or a cytotoxic moiety (CYT) as otherwise described herein.

Other enzyme labile linkers are the beta-glucosidase labile linkers according to the chemical structure:

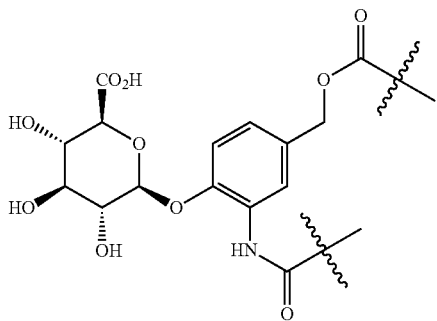 [SMILES: *C(=O)Nc1cc(COC(*)=O)ccc1O[C@@H]1O[C@H](C(=O)O)[C@@H](O)[C@H](O)[C@H]1O]

Where the points of attachment are joined to are joined to other portions of the labile linker, a connector moiety (CON), a non-labile linker (NLL), a virus invasion cell binding moiety (VICB) or a cytotoxic moiety (CYT) as otherwise described herein.

In each of the above labile linkers, at the point of attachment in each group, the labile linker may be further linked to a non-labile linker as otherwise described herein, or preferably a (poly)ethylene glycol group of from 1 to 10 glycol units (often 2 to 8 glycol units) or an alkylene chain from 1 to 20 methylene units, often 1 to 10 methylene units, often 1 to 8 methylene units, more often 1 to 6 methylene unit, often 2 to 4 methylene units.

Although numerous non-labile linkers may be used as otherwise described herein, a linker based upon polyethyleneglycol (PEG) linkages, polypropylene glycol linkages, or polyethyleneglycol-co-polypropylene oligomers (up to about 100 units, about 1 to 100, about 1 to 75, about 1 to 60, about 1 to 50, about 1 to 35, about 1 to 25, about 1 to 20, about 1 to 15, 2 to 10, about 4 to 12, about 1 to 8, 1 to 3, 1 to 4, 2 to 6, 1 to 5, etc.) may be favored as a linker because of the chemical and biological characteristics of these molecules. The use of polyethylene (PEG) linkages in either or both of the labile linker (LL), and the non-labile linker (NLL) may be preferred. Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

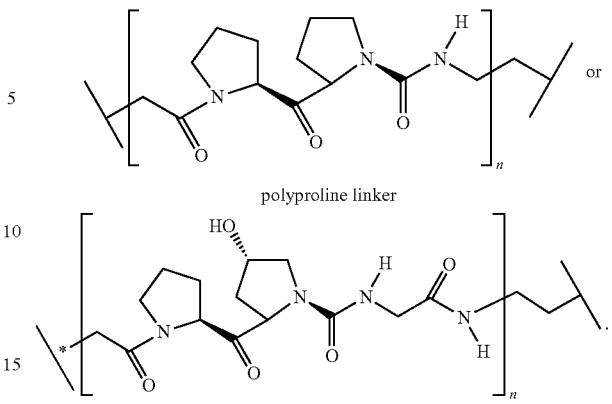

polyproline linker collagen linker

Additional non-labile linkers (NLL) include those according to the chemical structures:

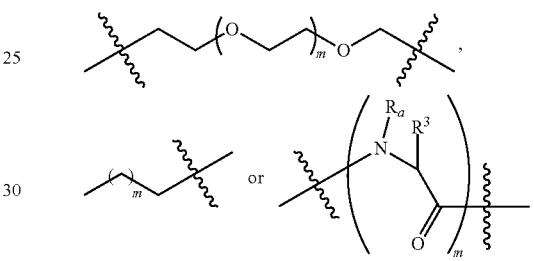

Or a polypropylene glycol or polypropylene-co-polyethylene glycol linker having between 1 and 100 glycol units;
Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);
m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and
n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).
Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units which may be further linked through amide groups, amino acids or other moieties compatible with polyethylene glycol groups. Still other linkers comprise polypeptides of amino acid residues (D or L) to which are bonded VICB groups or to labile groups as otherwise disclosed herein which are, in turn, bonded to CYT moieties as otherwise described herein. In another embodiment, as otherwise described herein, polypeptides may comprise non-naturally occurring amino acids (non-naturally occurring except for glycine) of the non-labile linker each of which has anywhere from 1-15 methylene groups separating the amino group from the acid group (and from 1 to 100 peptide groups) in providing a linker to the moiety. Note that each non-labile linker [NLL] otherwise described herein may be linked together, thus forming a longer extended non-labile linker comprising portions which are themselves considered non-labile linkers.

Another non-labile linker (which also may be used as an extension of a non-labile linker as described above and is often used as such) according to the present invention includes a linker based upon succinimide according to the chemical formula:

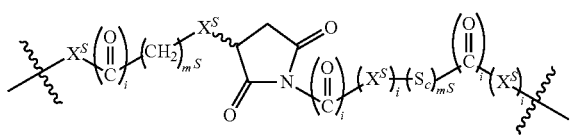

where each $X^S$ is independently S, O or N—$R^S$, preferably S;

$R^S$ is H or $C_{1-3}$ alkyl, preferably H;

$S_c$ is $CH_2$; $CH_2O$; or $CH_2CH_2O$;

i is 0 or 1; and $m^S$ is 0, 1, 2, 3, 4, 5, or 6.

Another non-labile linker is a moiety according to the chemical formula:

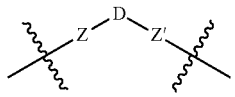

Where Z and Z' are each independently a bond, —$(CH_2)_i$—O, —$(CH_2)_i$—S, —$(CH_2)_i$—N—R,

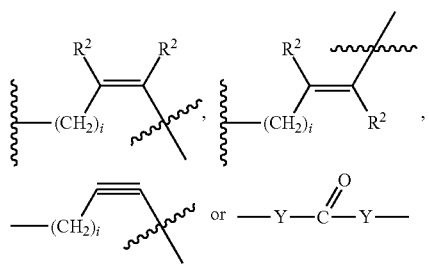

wherein said —$(CH_2)_i$ group, if present in Z or Z', is bonded to a connector, ABT or CBT;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

D is

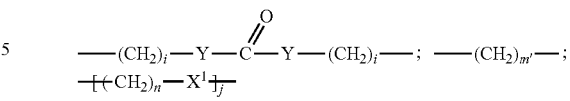

or a bond, with the proviso that Z, Z' and D are not each simultaneously bonds;

i is the same as above;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R; and

R is as described above, or a pharmaceutical salt thereof.

The term "connector", "connector molecule", "connector group" or "connector moiety" symbolized in the generic formulas by [CON] or CON, is used to describe a chemical group or moiety which is optionally included in bifunctional compounds according to the present invention. These moieties, when present, covalently connect one or more VICB moieties to a labile linker to which a CYT moiety is covalently attached, or alternatively, these moieties connect to the VICB moiety(ies) through a non-labile linker (NLL) and to a labile linker, which is covalently linked to a CYT moiety. The connector group may be the resulting moiety which forms from the facile condensation of two or more separate chemical fragments which contain reactive groups which can provide connector groups as otherwise described herein to produce bifunctional or multifunctional compounds according to the present invention. It is noted that a connector may be distinguishable from a linker in that the connector is the result of a specific chemistry which is used to provide connector molecules according to the present invention wherein the reaction product of these groups results in an identifiable connector group or part of a connector group which is distinguishable from the linker group, although in certain instances, incorporated into the linker group, as otherwise described herein. It is noted also that a connector group may be linked to a number of linkers to provide multifunctionality (i.e., more than one VICB moiety and/or more than one CYT moiety within the same molecule. It is noted that there may be some overlap between the description of the connector group and the linker group such that the connector group is actually incorporated or forms part of the linker, especially with respect to more common connector groups such as amide groups, oxygen (ether), sulfur (thioether) or amine linkages, urea or carbonate —OC(O)O— groups as otherwise described herein. It is further noted that a connector (or linker) may be connected to VICB, a linker (e.g. a non-labile linker NLL, a labile linker LL or both) or CYT moieties at positions which are represented as being linked to another group using the using the symbol ⋇. Where two or more such groups are present in a linker or connector, any of a VICB moiety, a linker (NLL and/or LL) or a may be bonded to such a group. Where that symbol is not used, the link may be at one or more positions of a moiety.

Common connector groups which are used in the present invention include the following chemical groups:

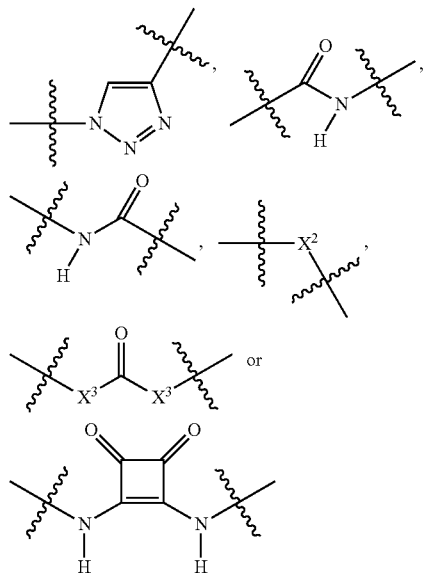

Where $X^2$ is O, S, $NR^4$, S(O), S(O)$_2$, —S(O)$_2$O, —OS(O)$_2$, or OS(O)$_2$O;

$X^3$ is O, S, $NR^4$; and $R^4$ is H, a $C_1$-$C_3$ alkyl or alkanol group, or a —C(O)($C_1$-$C_3$) group. The triazole group, indicated above, is a preferred connector group.

As discussed hereinabove, it is noted that each of the above groups may be further linked to a chemical moiety which bonds two or more of the above connector groups into a multifunctional connector, thus providing complex multifunctional compounds comprising more than one VICB and/or CYT groups within the multifunctional compound.

Thus, multifunctional moieties which contain three or more functional groups may be used to covalently bind to one or more VICB groups, linkers (NLL and/or LL linker groups), CYT groups and/or CON groups) to create compounds containing more than one VICB and/or CYT group. These multifunctional groups include any chemical moiety which contains at least three functional groups which can be used to covalently bind to the various groups as described above. Preferred multifunctional connector groups for use in the present invention include five or six-membered ring aryl or heteroaryl groups (especially six-membered ring groups) exemplified by multifunctional, especially trifunctional or tetrafunctional aryl or heteroaryl groups, including phenyl, pyridyl, pyrimidinyl, 1,3,5-triazinyl, 1,2,3-triazinyl, 1,2,4-triazinyl groups, each of which is substituted with at least 3 and up to 6 functional groups. These groups preferably include phenyl, pyridyl, pyrimidinyl and 1,3,5-triazinyl, 1,2,3-triazinyl, 1,2,4-triazinyl groups, especially groups according to the chemical structure:

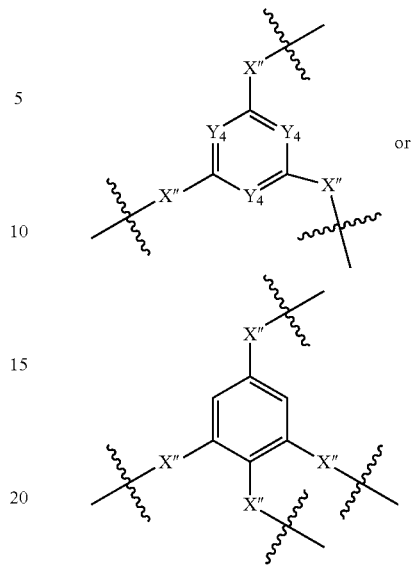

where $Y_4$ is C—H or N; and

X" is an electrophilic or nucleophilic group, preferably $(CH_2)_{n''}O$, $(CH_2)_{n''}N^{RCON}$, $(CH_2)_{n''}S$, $(CH_2)_{n''}$ or $(CH_2)_{n''}C=O$;

where $N^{RCON}$ is H or a $C_1$-$C_3$ alkyl, preferably H or $CH_3$ and n" is 0, 1, 2 or 3.

Pharmaceutical Compositions

Pharmaceutical compositions comprise combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the topical cream or lotion may be used prophylatically to prevent infection when applied topically in areas prone toward virus infection. In additional aspects, the compounds according to the present invention may be coated onto the inner surface of a condom and utilized to reduce the likelihood of infection during sexual activity.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other bifunctional compound according to the present invention or other anti-HIV agent which may be used to treat HIV infection or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from HIV infection can be treated by administering to the patient (subject) an effective amount of the CDM-H compound according to the present invention including pharmaceutically acceptable salts, solvates or polymorphs, thereof optionally in a pharmaceutically acceptable carrier or diluent, either alone, or in combination with other known antiviral or pharmaceutical agents, preferably agents which can assist in treating HIV infection, including AIDS or ameliorate the secondary effects and conditions associated with HIV infection. This treatment can also be administered in conjunction with other conventional HIV therapies. The coadministration of latent HIV activator compounds such as prostratin, bradystatin 1, and related analogues as set forth in FIG. 4, hereof (see De Christopher, et al., *Nature Chemistry*, published online Jul. 15, 2012, pages 1-6), bryostatin 1, bryostatin 2, IL-7, histone deacetylase inhibitors, including zolinza (vorinostat), DNA methylation inhibitors including decogen (decitabine) and mixtures thereof represents an alternative approach to the treatment of HIV which can result in effective therapy including the eradication of HIV (cure) from a patient.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anti-HIV agents, antibiotics, antifungals, anti-inflammatories, or anti-viral compounds. In certain preferred aspects of the invention, one or more CDM-H compounds according to the present invention are coadministered with another anti-HIV agent and/or another bioactive agent, especially including a latent HIV activator as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Development of CDM-Hs

While developing cytotoxic-drug delivery small-molecules targeting HIV (CDM-Hs), the first concern was how the conjugated cytotoxic agent would gain entry into the targeted cell in order to induce a cytotoxic response. Although there is a significant body of literature pertaining to the development of chimeric toxins targeting HIV-infected cells, there have been no studies reporting how these conjugates are able to gain entry into the infected cell to deliver the cytotoxic payload. The Env complex is known to possess a highly conserved cytoplasmic tail containing a tyrosine endocytic signal sequence, and Env has been shown to undergo endocytosis during the period of infection, possibly to evade immune recognition.[23-25] Cellular endocytosis has been extensively reviewed,[26] as has been the development of drug-delivery strategies that target the endocytic pathway.[27, 28] Given that most active endocytic pathways lead to lysosome fusion,[29] most drug delivery strategies that target endocytic pathways utilize linkers (which connect a targeting moiety to the payload) that can be hydrolyzed at low pH or linkers that contain peptidic substrates for lysosomal proteases (e.g., cathepsin B), thus releasing the active cytotoxic drug or other payload.[27] Alternatively, the payload can be attached to the delivery/targeting molecule in such a way that does not disrupt its function. Considering these factors, they initially focused on chemical linker strategies that would release the chosen cytotoxic payload in acidic aqueous environments; however, in future studies, alternate conjugation strategies (e.g., disulfide bond, protease substrates) should also be considered.

The next consideration for CDM-H design was the choice of cytotoxic molecule. Consistent with our overall goal of developing small-molecule-based alternatives to protein/peptide-based therapeutics, they chose not to utilize cytotoxic proteins, such as *Pseudomonas* exotoxin A, but rather low molecular weight, non-peptidic cytotoxic agents. The use of cytotoxic small molecules to kill HIV-infected cells is limited to only one study.[18] In this work, the cytotoxic anthracycline doxorubicin was conjugated to an anti-gp120 antibody via an acid-labile acyl hydrazone (see discussion above). In addition, since doxorubicin is a mainstay of cancer therapeutics, there are a significant number of investigations that conjugate this chemotherapeutic to various targeting moieties (e.g., monoclonal antibodies,[30] peptides,[31] and various small molecules[32]) as well as carrier peptides[33] and to half-life enhancing molecules.[34] Thus, much is known not only about its activity but also conjugation chemistry.[35-37] Given these factors, the inventors utilized doxorubicin as our cytotoxic payload, however, this strategy is not limited, and thus can (and is currently) be extended to the use of other cytotoxic agents, such as lomaiviticins, chlorambucil, carbocisplatin, calicheamicins, etc.

Figure 10:
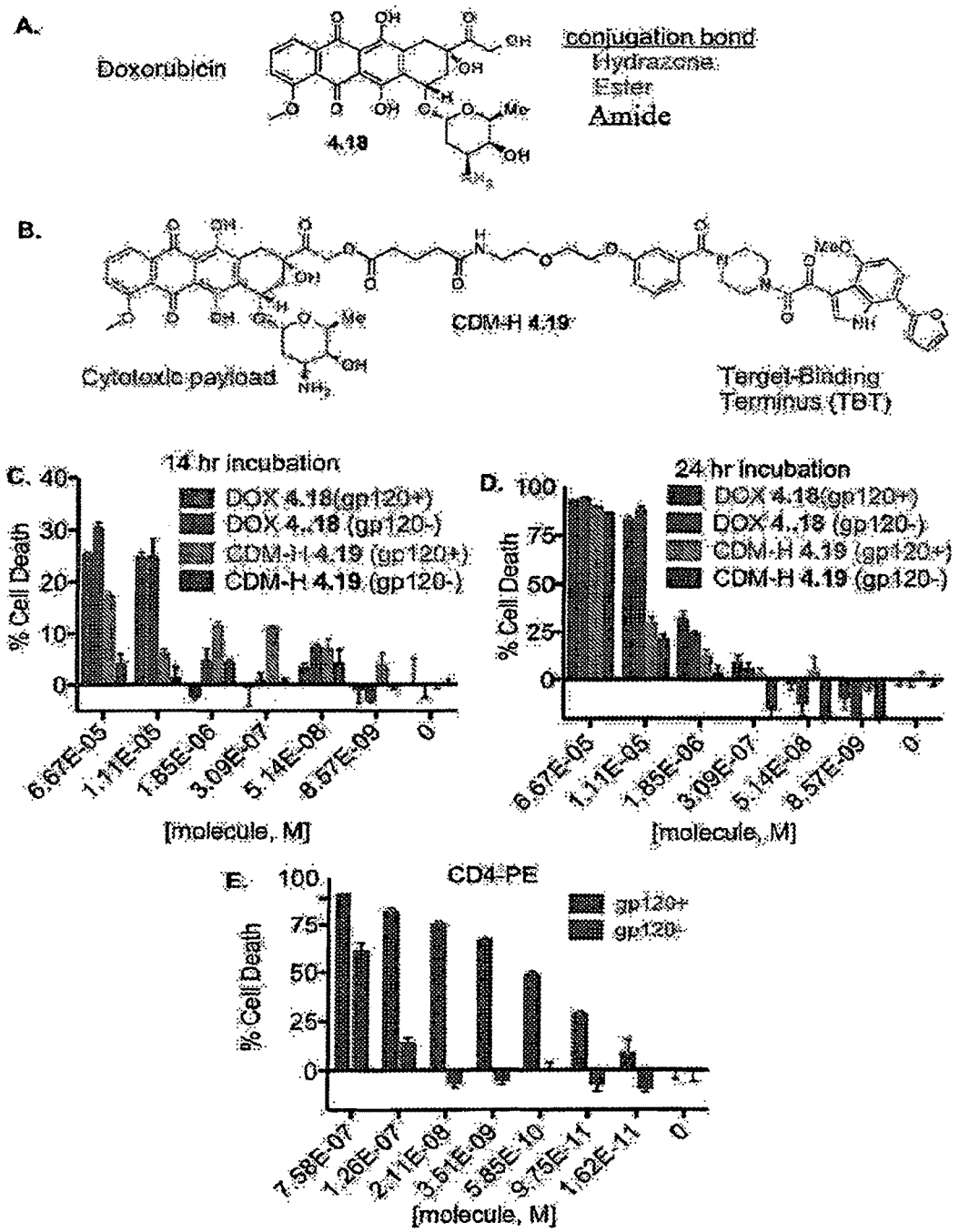
FIG. 10 shows cytotoxic-drug delivery molecule targeting HIV gp120 (CDM-H) is capable of delivering a cytotoxic response to gp120 expressing cells in the absence of any other immune components. (A) Chemical structure of DNA intercalating anthracycline doxorubicin (4.18), which is used as the toxic payload of CDM-Hs and can be conjugated to a targeting molecule through various conjugations—hydrazone, ester and amide. (B) Structure of CDM-H 4.19 in which toxic payload is conjugated to TBT via ester bond. (C) Cytotoxicity assay in which 4.18 and 4.19 are incubated with CHO-env (gp120+) or CHO-pSV (gp120−) cells for a period 14 h or 24 h (D). CDM-H 4.19 demonstrates gp120-selective cytotoxicity at 14 h incubation, however is non-specifically (gp120 independent) cytotoxic at 24 h incubation. (E) CD4-PE is used as a positive control. Data is plotted as mean with standard deviation error bars.

The initial CDM-H design was based on studies by Kiessling and coworkers, in which they conjugated doxorubicin to a non-peptidic $\alpha_v\beta_3$-integrin targeting molecule via ester linkage at the alpha hydroxy group.[38] CDM-H 4.19 (FIG. 2) was synthesized as shown in Schemes S4.3 (FIG. 4) and S4.4 (FIG. 5) and is based upon the ARM-H scaffold (as described in WO 2011/046946, Apr. 21, 2011 and WO 2012/068366 May 24, 2012) with the linker connected to the primary hydroxyl group of doxorubicin at the meta-position of the benzamide ring. The inventors first confirmed that the conjugation to doxorubicin did not impair the ability of 4.19 to bind to gp120 and inhibit the CD4 interaction. As shown in FIG. 10, 4.19 did indeed inhibit the CD4-gp120 interaction at a similar potency observed for the ARM-H 3.11 analog. Next, the inventors sought to determine if 4.19 could selectively kill HIV-1 gp120 expressing cells over control cells. For this, the inventors developed a cell viability assay in which they seeded CHO-env (gp120+) cells or the isogenic control cells CHO-pSV (gp120−) into 96-well plates, then added increasing concentrations of 4.19 and monitored the cell viability over a set time of 14 h. As can be seen from FIG. 10, 4.19 exhibited significant (~12%) gp120-specific cytotoxicity at concentrations as low as 309 nM. More importantly, no non-specific cytotoxicity was observed, even at concentrations as high as 67 μM, while free doxorubicin was non-specifically toxic. As a positive control, they performed a parallel assay with CD4-PE (FIG. 10). Interestingly, they observed gp120-specific toxicity of 4.19 at concentrations in which no toxicity was observed for free doxorubicin (at 310 nM and 1.85 M). These observations suggest that modification of doxorubicin (conjugation to TBT/VICB) reduces its overall toxicity at higher concentrations. However, it increases the gp120-specific toxicity at lower concentrations, suggesting that the addition of the gp120 targeting group (TBT/VICB) enhances the effective concentration of doxorubicin in gp120 expressing cells over non-gp120 expressing cells. However, when CDM-H compound 4.19 (see FIG. 2) was incubated with cells for longer times (24 h), they noticed a complete loss in selectivity between gp120+ and gp120− cells as well as an increase in overall toxicity (4.19 was more toxic at longer incubation times than shorter times).

Figure 11:
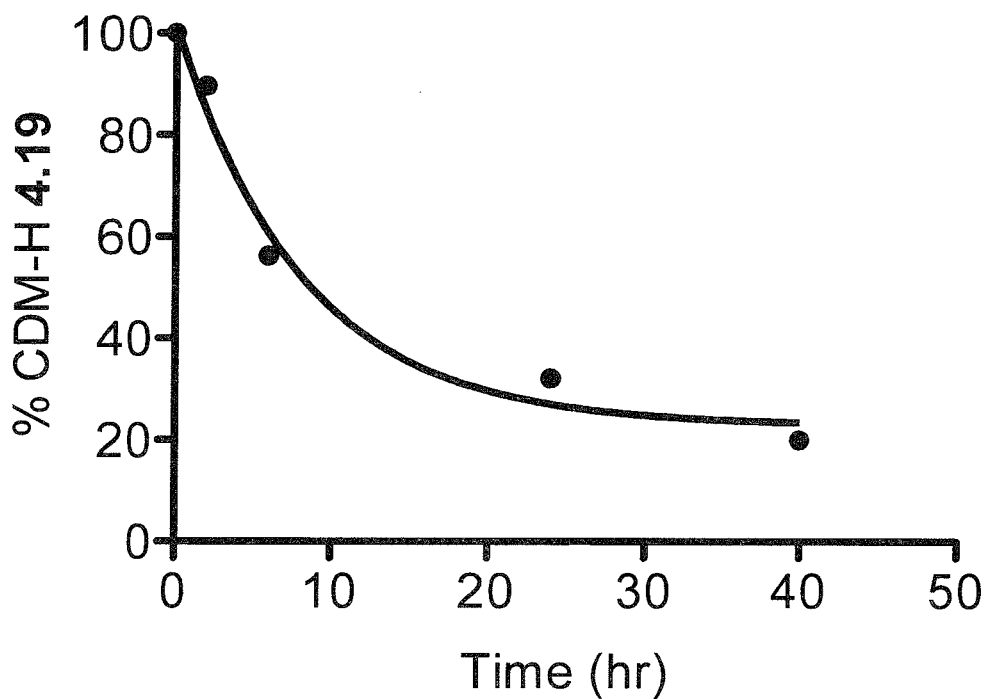
FIG. 11 shows the hydrolysis of CDM-H ester 4.19, as detected by UPLC/HR-MS, with an estimated hydrolytic half-life of 5.7 hours.

With this loss of selectivity and increase in toxicity, the inventors hypothesized that the ester linkage may have undergone hydrolysis, producing the free active form of doxorubicin. In order to investigate this possibility, we developed an LC/MS method to monitor the half-life of 4.19 when incubated under the assay conditions used in the cytotoxicity assay. Interestingly, we observed that the half-life of the ester bond in PBS buffer at 37° C. was approximately 5.6 h (FIG. 11), suggesting that the loss in selectivity over longer incubation times may indeed be the result of hydrolysis. In order to compensate for the lability of this ester linkage, we explored alternative conjugation strategies.

Figure 12:
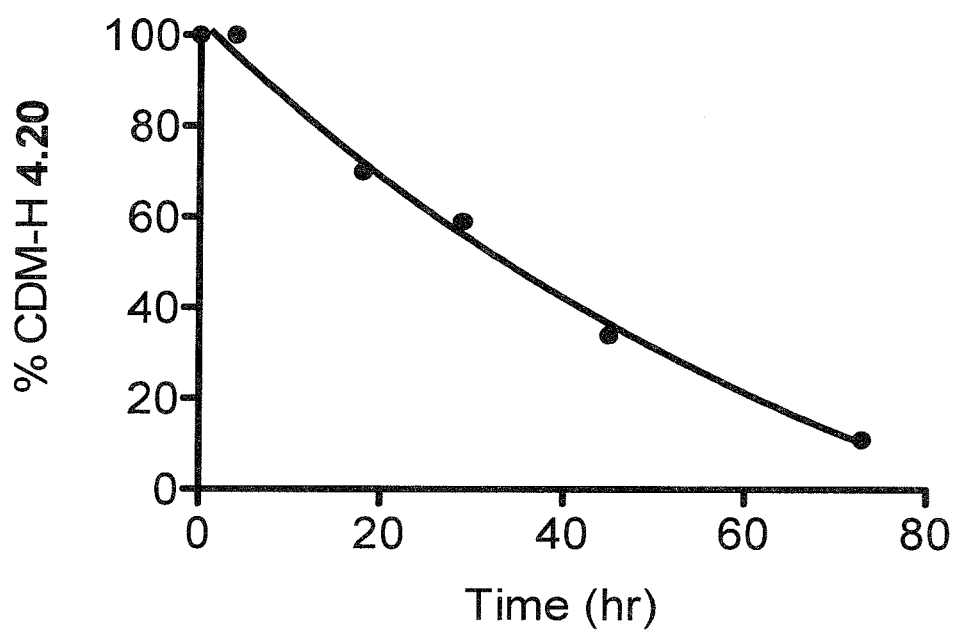
FIG. 12 shows the hydrolysis of CDM-H 4.20, as detected by UPLC/HR-MS, with an estimated hydrolytic half-life of 56 hours.
Figure 13:
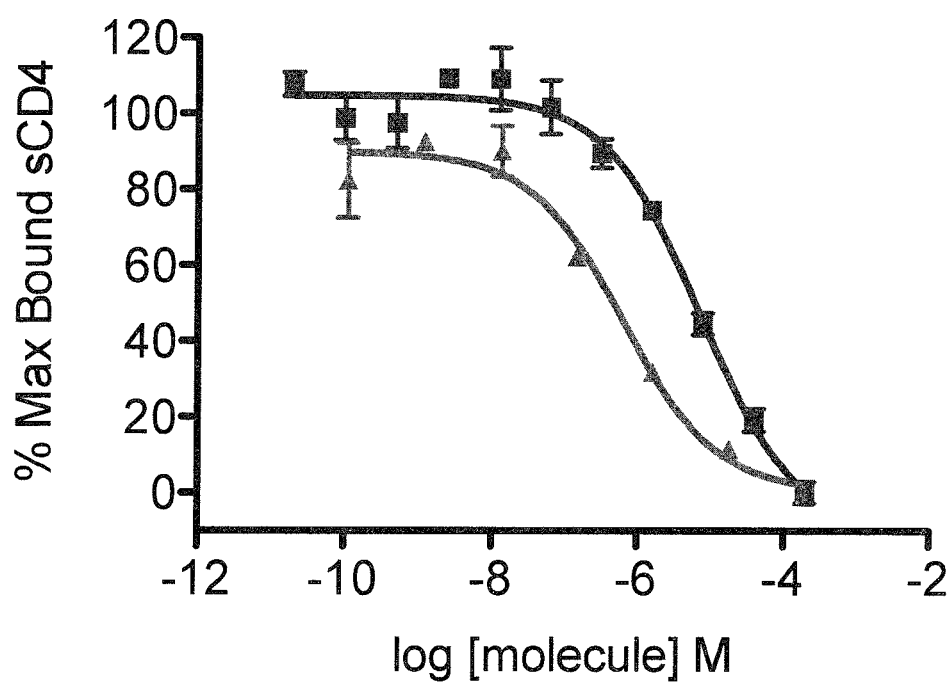
FIG. 13 shows the CD4 inhibition ELISA of CDM-H 4.19 and 4.20, demonstrating that both analogs inhibit the CD4-gp120 interaction.
Figure 14:
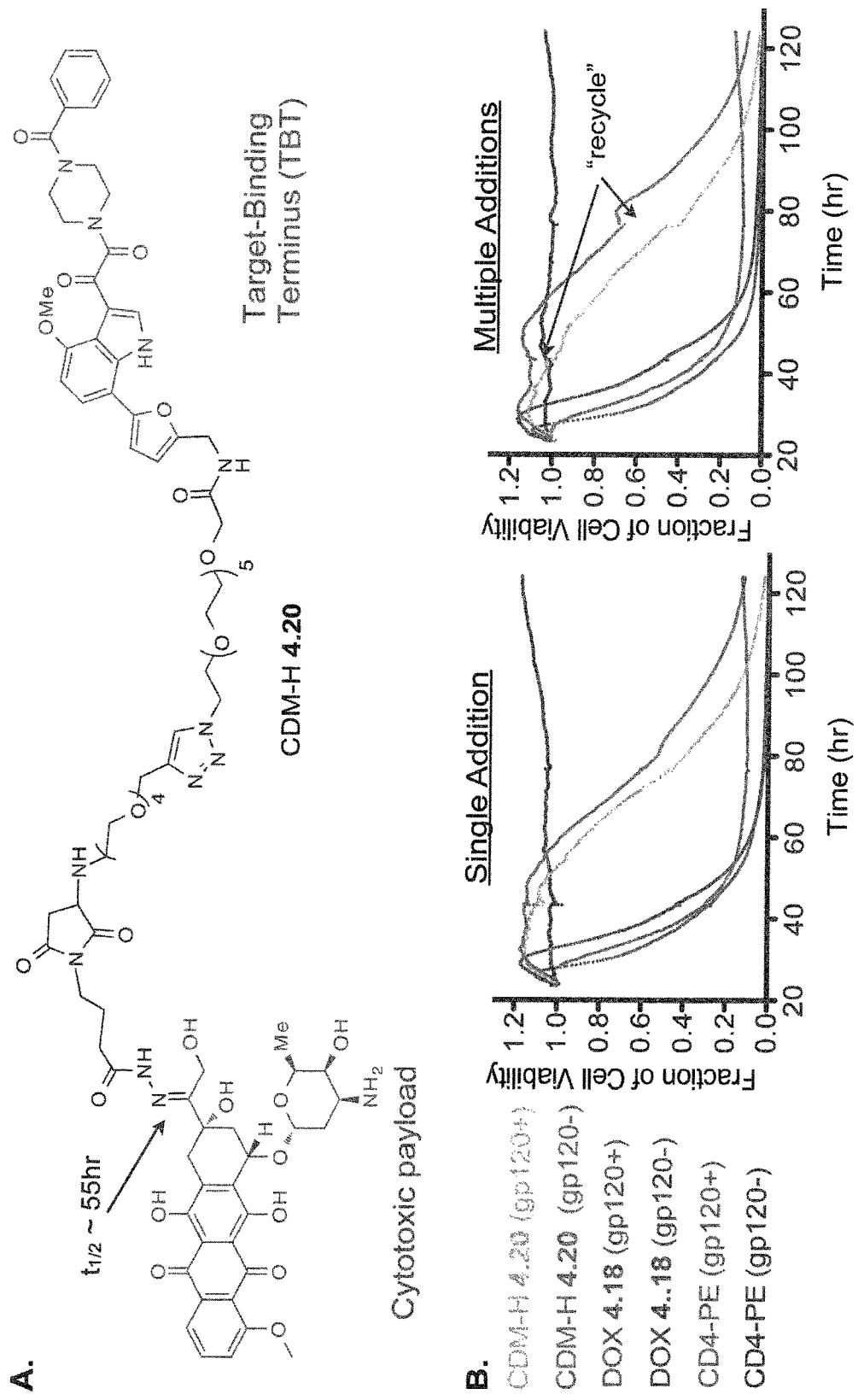
FIG. 14 shows CDM-H analog 4.20 toxicity against gp120-expressing cells. (A) Chemical structure of 4.20, which is conjugated to doxorubicin via acyl hydrazone, measured to have a hydrolysis half-life of approximately 55 hrs. (B) CHO-env (gp120+) and CHO-pSV (gp120−) viability in the presence of 4.18 (10 µM), 4.20 (10 µM), or CD4-PE (1 µg/mL) as measured with xCELLigence instrument. Cell viability examined over a span of ~120 h after a single addition of all compounds or after an initial addition, followed by compound "recycling" as described in the text and Supporting Information.

In studies by Vyas and co-workers, doxorubicin was conjugated to a linker via an acyl hydrazone linkage, which was found to be completely stable at pH 7.4, however, at pH 5.0 (approximate pH of lysosome is 4-5[39]), it possessed a hydrolysis half-life of approximately 5 h.[35] Considering these observations, we synthesized a new CDM-H analog (4.20, FIG. 2) which has doxorubicin conjugated to the TBT/VICB moiety via acyl hydrazone. In addition, in this CDM-H, the PEG linker was attached to the furan of the TBT/VICB, which results in higher gp120 affinity. The inventors first demonstrated that the hydrolysis half-life of 4.20 at pH 7.4 was extended to approximately 55 hours (FIG. 12) and that it maintained the ability to inhibit the CD4-gp120 interaction (FIG. 13). Next, using the xCELLigence cell viability monitoring system, we examined the toxicity of 4.20 (10 μM) against CHO-env (gp120+) cells and CHO-pSv (gp120−) cells over a period of 150 h both when 4.20 was added only once and when added multiple times (growth media removed and replenished with fresh media containing 4.20). As shown in FIG. 14, under conditions in which 4.20 was added only once, the inventors observed a consistent ~10% gp120-selective toxicity, however, when 4.20 was added multiple times, gp120-selective toxicity increases to ~35% (at ~80 h). The inventors hypothesize that the recycling of the media removes any non-specific doxorubicin (via hydrolyzed 4.20) and replenishes it with non-hydrolyze 4.20 which can still target gp120-expressing cells. Despite these results, under both conditions we observed a significant increase in toxicity of 4.20 against the CHO-pSV cells (gp120−).

Figure 15:
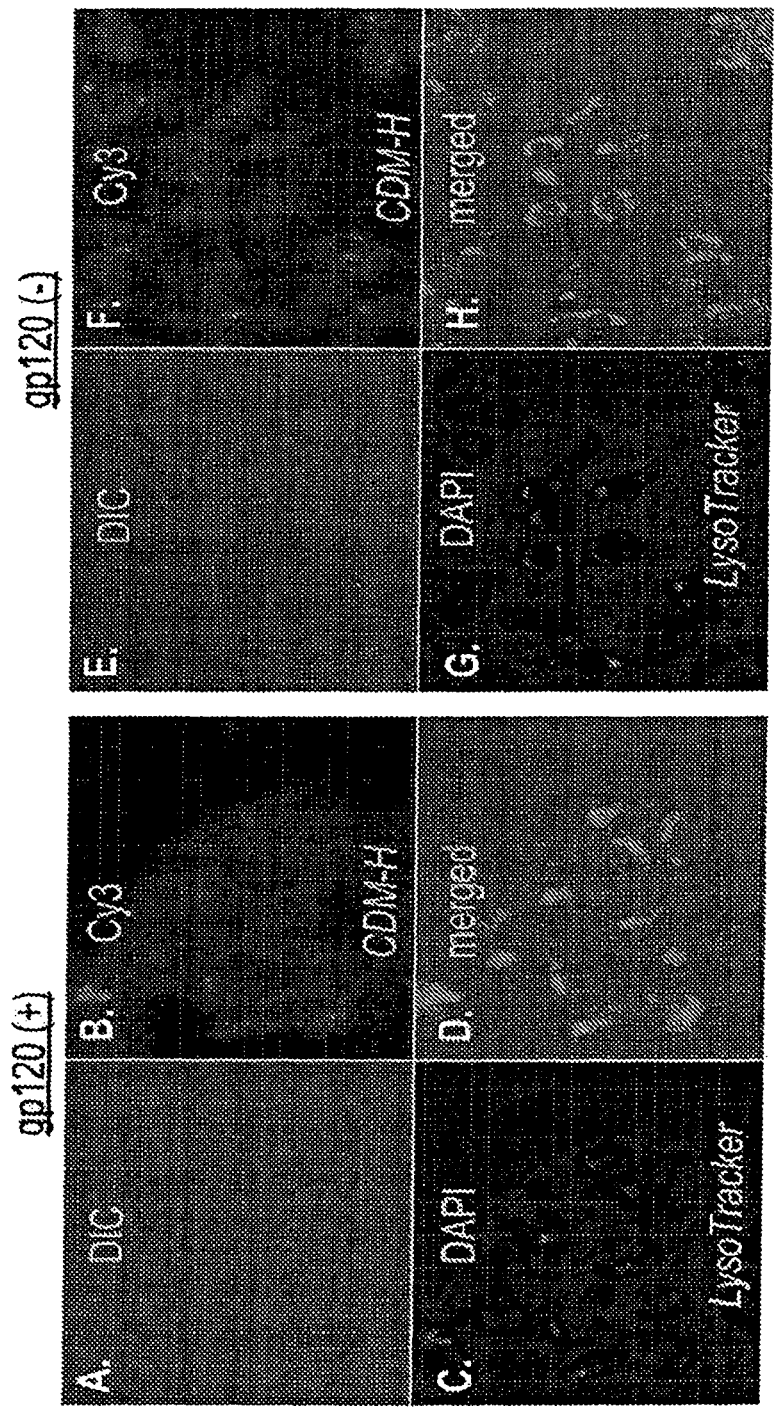
FIG. 15 shows immunofluorescence images of CHO-env (gp120+; panels A-D) and CHO-pSv (gp120−; panels E-H) when stained with LysoTracker lysosomal dye and incubated CDM-H 4.20 after 10 min incubation. Merged images (D for gp120+ and H for gp120−) show that CDM-H costains with LysTracker dye, suggesting that significant levels of 4.20 localize to the lysosome, independently of gp120 expression.
Figure 16:
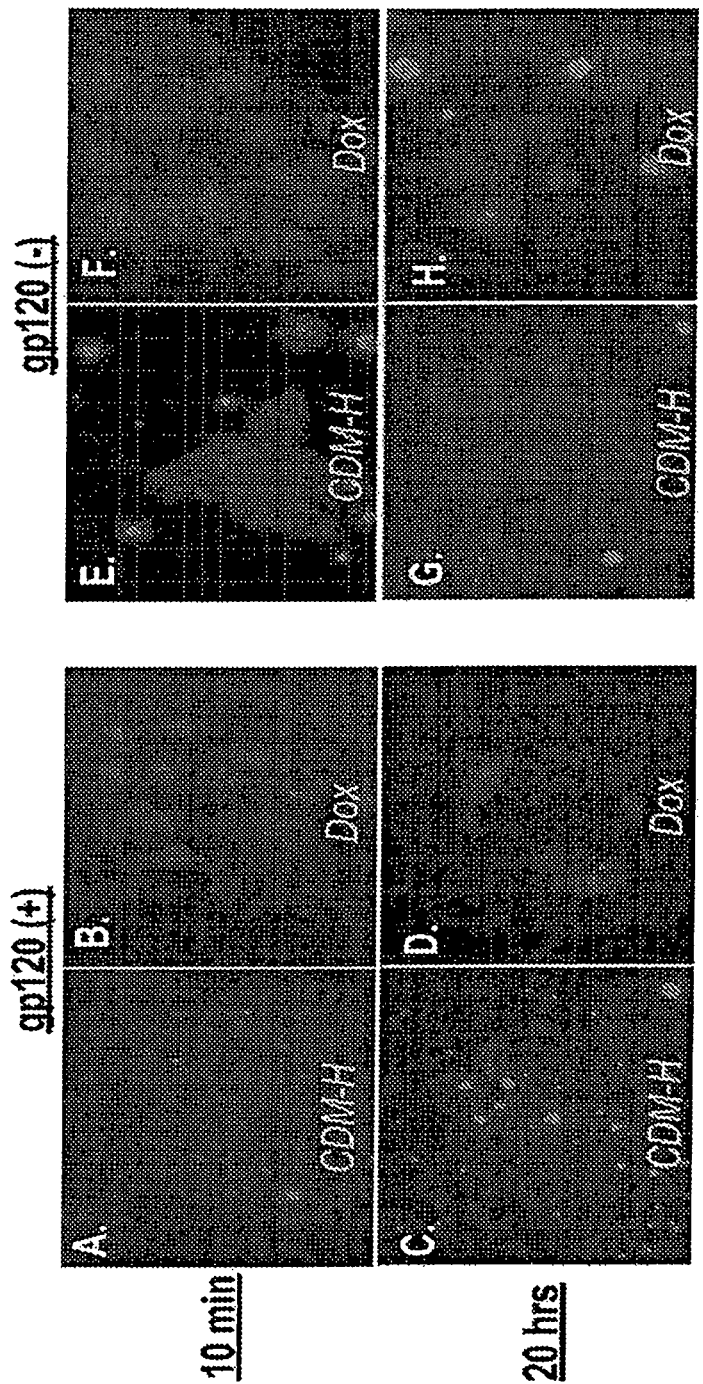
FIG. 16 shows fluorescence micrographs when CDM-H 4.20 or doxorubicin (4.18) is incubated with CHO-env cells after 10 min (A-B) or 20 hrs (C-D) and CHO-pSv cells (E-H). Formation of fluorescent particles, specifically after long incubation periods, suggests the formation of micelles.

The inventors hypothesized that this non-specific toxicity is the result of non-specific uptake of 4.20. Since doxorubicin itself is fluorescent,[40] the inventors performed immunofluorescence microscopy to track the subcellular location of 4.20 over time. In this experiment, the inventors co-stained CHO-env (gp120+) and CHO-pSv (gp120−) cells with LysoTracker dye, which stains acidic organelles of the cells (i.e., lysosomes) and incubated with 4.20. As can be seen in FIG. 15, there is significant co-localization of (4.20-doxorubicin) and (LysoTracker) fluorescence for both the CHO-env and CHO-pSv cells, suggesting that 4.20 is localized to the lysosomes of both cell types independently of gp120 expression. During the same incubation time, free doxorubicin rapidly enters the nucleus of the cell (FIG. 16). During this incubation, after approximately 20 h we noticed that 4.20 began forming aggregates, possibly micelles, which is not unreasonable considering the polarity of doxorubicin (i.e., one primary amine, 5 hydroxyl groups) compared to that of the TBT/VICB moiety, which is relatively hydrophobic. Concentration-dependent aggregate formation was also confirmed by dynamic light scattering analysis (FIG. 16). Non-specific endocytosis and pinocytosis of micelles, aggregates and nanoparticles is a well known feature of mammalian cells,[41-44] and thus may explain the relatively high levels of non-specific cytotoxicity of 4.20.

The inventors hypothesize that the long linker length of 4.20 may favor separate solvation of the doxorubicin as well as the VICB, thus promoting micelle formation. In alternative studies, the linker length is reduced (similar to that of 4.19). The synthesis of analogs with shorter linkers and their biological evaluation is currently ongoing in the lab. In addition, alternate conjugation strategies and cytotoxic payloads are investigated. In addition, the inventors are using CDM-Hs according to the present invention in an "activation-elimination" strategy[7] to target latent HIV infection (FIG. 1). In these studies, the inventors examine the ability of CDM-Hs to selectively kill latently infected cells that have been activated (induced to express HIV proteins)[45, 46] with molecules such as prostratin[47, 48] and other latent HIV activators in various cell and animal models.[49-51]

The following detailed description outlines the design and synthesis of a number of bifunctional small-molecules capable of delivering cytotoxic moities into cell (CD4 cells) which are infected with HIV.

The following chemical syntheses which are presented in Scheme 1 (FIG. 4) and Scheme 2 (FIG. 5) may be used to synthesize the compound labeled as 4.19 in FIG. 2 which shows exceptional activity as an anti-HIV agent. The Scheme 1 chemical synthesis provides intermediate S4.11 from basic starting materials which represents a basic VICP moiety to which a linker has been attached on the benzoyl group to provide intermediate amine S4.11. Intermediate amine S4.11 can be used to condense an appropriately substituted cytotoxic agent such as doxorubicin or other cytotoxic groups as described herein to produce final compound 4.19 pursuant to Scheme 2. Minor modifications of the scheme 1 chemistry may produce linkers at various positions of the VICB moiety which may be used to link cytotoxic moieties as otherwise described herein. Alternative synthesis which are set forth in chemical schemes 4.5 (FIG. 6), Scheme 4 (FIG. 7), Scheme 5 (FIG. 8) and Scheme 6 (FIG. 9) and as described in related international applications WO 2011/046946 and WO 2012/068366 provide standard chemical syntheses of all of the related VICB moieties to which cytotoxic moieties may be linked at various positions of the moiety (using non-labile linkers and/or labile linkers and/or connector moieties as generally described herein). Attaching one or more of the labile linkers which are described herein can be afforded readily using standard synthetic chemical techniques by condensing a nucleophilic group onto an electrophilic group to afford a cytotoxic moiety (CYT) which is linked to a VICB moiety through a labile linker and optionally a non-labile linker and/or a connector moiety. This standard chemistry is well known in the art.

For example, Scheme 1 (FIG. 1) provides a straight forward chemical synthesis to provide functional group chemistry which can be readily modified to introduce a labile linker and cytotoxic moiety on the amine moiety of the phenyl group as depicted for compound S4.11. In this scheme, the Arene 1 group (which in the scheme is a furan group, but can vary considerably pursuant to the present invention by introducing an arene 1 group as otherwise disclosed herein onto the carbon of the indole which is substituted with a bromine group) remains unsubstituted (but can be readily substituted using a substituted arene 1 precursor) as is the methoxy group on the head position of the indole group. Scheme 4.4 (FIG. 5) shows the condensation of an appropriately modified cytotoxic group (in this case doxorubicin) which is condensed onto the amine end of compound S4.11 to form compound 4.19 as the formate salt.

Figure 8:
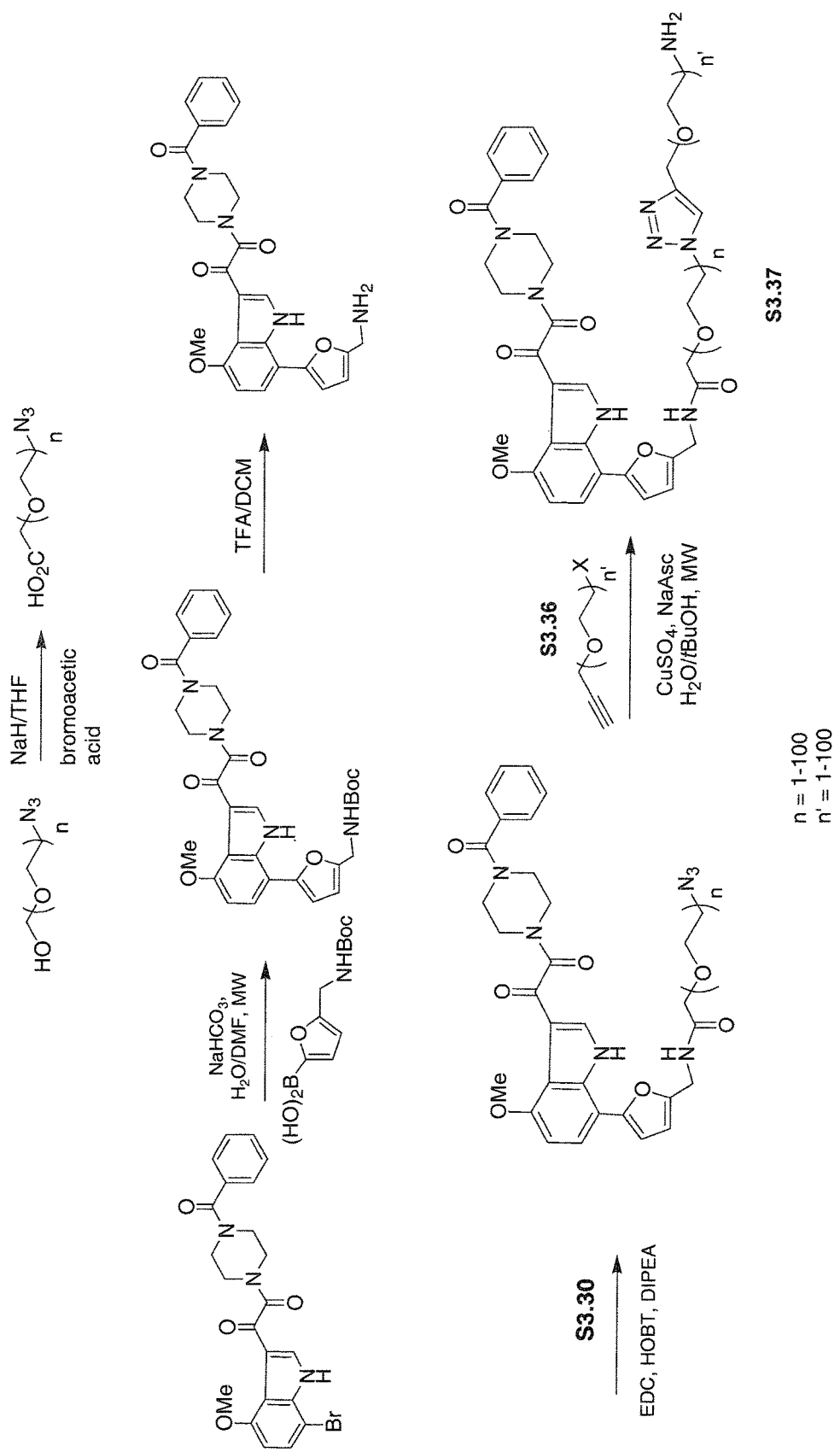
FIG. 8 shows chemical scheme 5 which exemplifies a generic chemical scheme for functionalizing Arene 1 to place a cytotoxic group at the end of the arm which extends from Arene 1.

Scheme 4.5 (FIG. 6) shows the formation of final compound 4.20 from amine compound S3.37 (containing a substituted Arene 1 group to which a linker-cytotoxic moiety construct is attached, the synthesis of which is depicted in Scheme 5, FIG. 8 hereof) by reacting amine S3.37 with 2-mercapto propanoic acid to form intermediate S4.14. Intermediate S4.14 is condensed onto the cytotoxic moiety S4.15 which contains an acid labile linker group and a maleimide group onto which the thiol group from S4.14 may be introduced to provide compound 4.20 as acetate salt.

Figure 7:
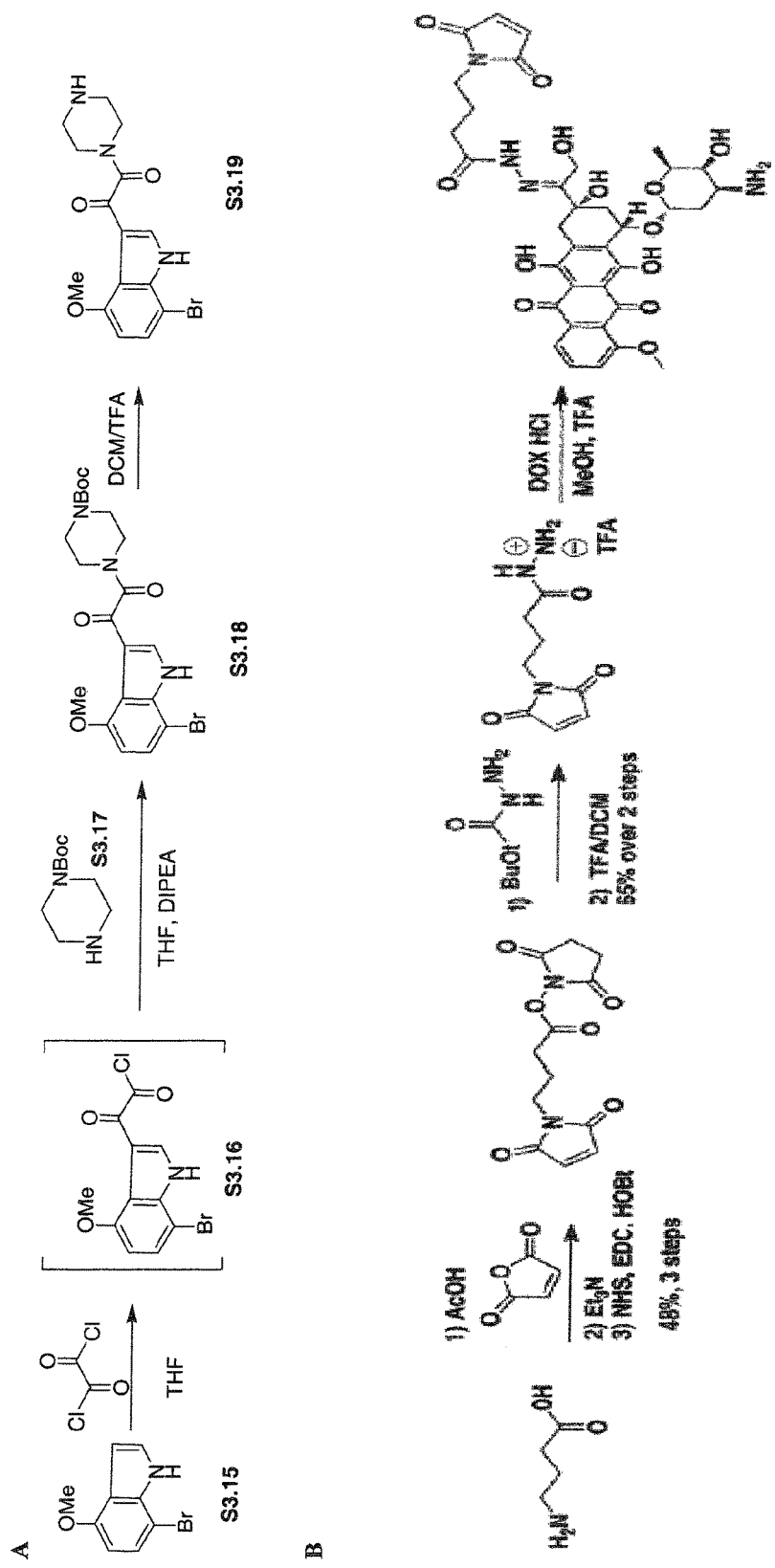
FIG. 7A shows chemical scheme 4 which is directed to functionalizing the indole ring 3.15 to build up the right hand portion of the molecule to provide a piperazine ring which can be readily functionalized to provide Arene 2 groups which may be optionally substituted with one or more of a non-labile linker, a labile linker, one or more connector groups and a cytotoxic group.
FIG. 7B shows the chemical synthesis of a cytotoxic moiety, in this case doxorubicin, containing a labile linker to be condensed onto the VICB moiety to provide a preferred CDM-H according to the present invention.

Scheme 4 (FIG. 7A) provides a facile synthesis of intermediate S3.19 which provides a piperazine group on a bromo- and methoxy substituted indole group which can be readily functionalized pursuant to the present invention with an optionally substituted arene 2 group which group may be substituted or unsubstituted and may be further covalently linked to a labile linker and cytotoxic moiety. In addition, intermediate S3.29 may be modified to introduce an optionally substituted Arene 1 group (which can be further functionalized to contain a cytotoxic group) at the bromo-substituted position and the indole group may further modified to contain a cytotoxic moiety at the methoxy position of the indole group. Thus, scheme 5, FIG. 7 shows the basic synthesis of a readily functionalized intermediate from available starting material S3.15 to provide, through several steps, intermediate S3.19 which contains a piperazine group which may be further functionalized pursuant to the present invention. In addition, the bromo group on the indole may be readily substituted with a functionalized Arene 1 group as set forth in Scheme 5, FIG. 8 hereof (e.g. amine protected/NHBoc arene group such as a furan or other aryl group) to displace the bromine group, followed by linking the unprotected amine group on the Arene I group with, for example, a non-labile linker, a connector (e.g. a 1,2,3-triazole group) molecule, a labile linker and a cytotoxic group. These reactions are generalized from the chemistry which is otherwise disclosed herein. This chemical approach to functionalizing the Arene I group chemistry as depicted in Scheme 5, FIG. 8, is also described generally in international patent publication WO2012/068366, which is incorporated by reference herein.

Figure 6:
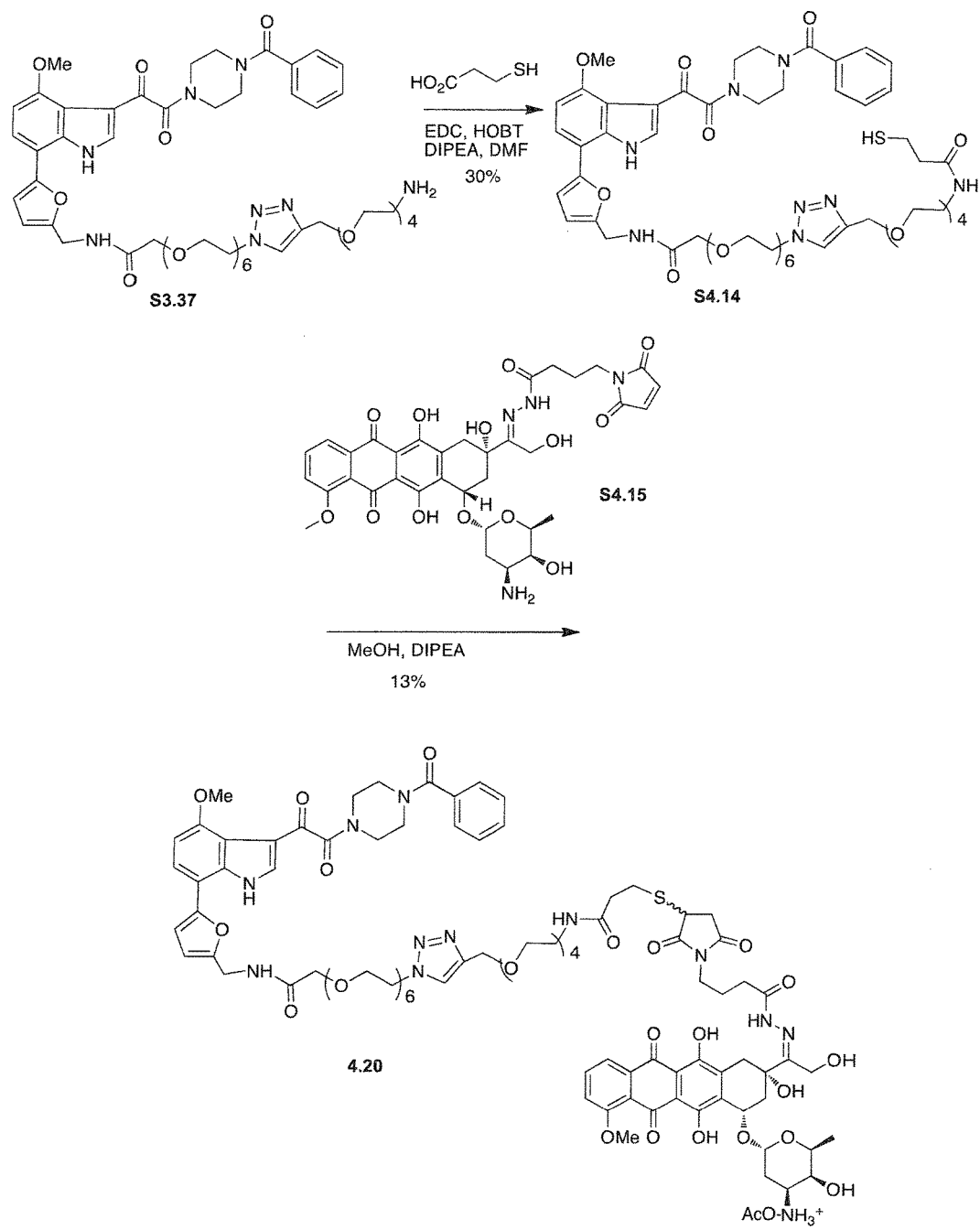
FIG. 6 shows chemical scheme 3 which is directed to the final steps to produce CDM-H 4.20 from thio S4.14 and known maleimide S4.15.

FIG. 7B shows the modification of the cytotoxic compound doxorubicin to provide a labile linker which is further linked to a group which can be condensed with the VICB moiety as per the chemical synthesis scheme 4.5 (FIG. 6). Likewise, each of the cytotoxic compounds which may be used pursuant to the present invention may be readily derivatived and functionalized by reacting a functional group (as indicated in the definition of cytotoxicity terminus or cytotoxic agent moiety) in the cytotoxic molecule to provide a labile linker, which is further linked to the VICB moiety, through a non-labile linker and an optional connector molecule, to provide compounds according to the present invention.

Figure 9:
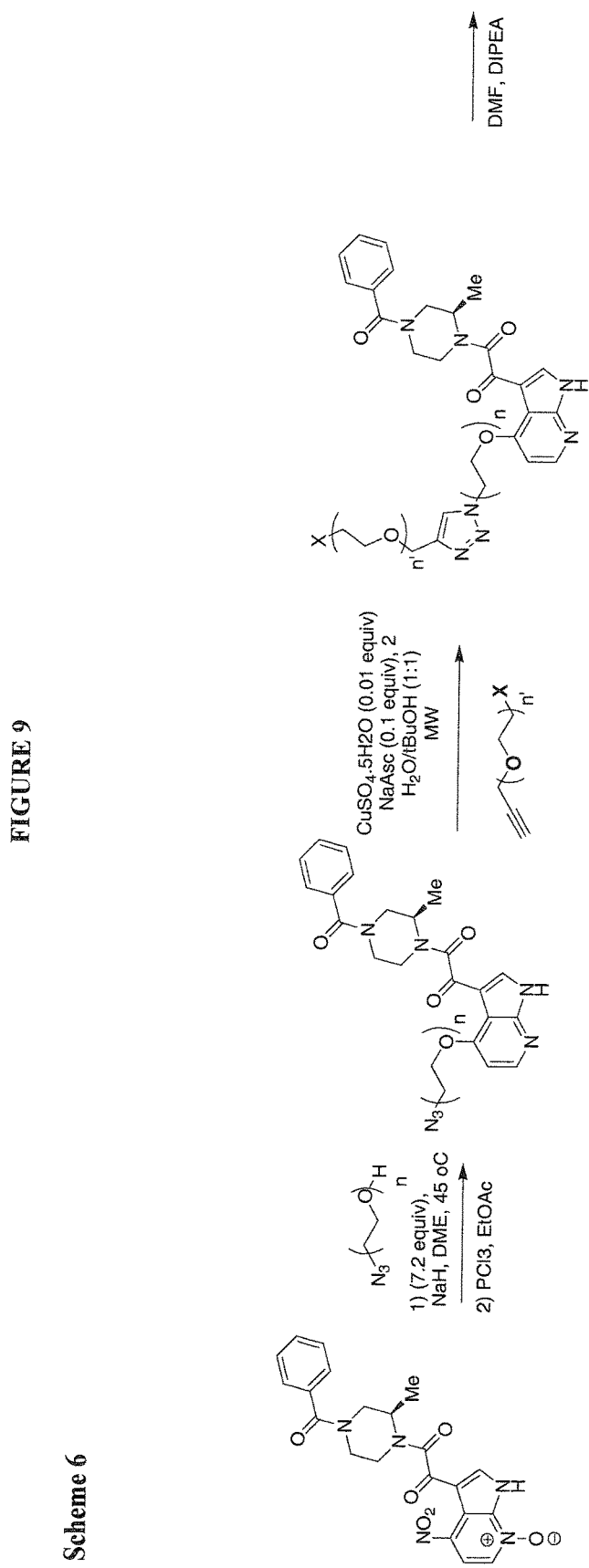
FIG. 9 shows chemical scheme 6 which exemplifies a generic chemical scheme for introducing a cytotoxic moiety on the top left portion of the indole ring.

Scheme 6, FIG. 9 shows the introduction of a cytotoxic moiety on the head position of the pyrrolopyridine heteroaryl moiety as depicted. Accordingly, the chemical synthesis of pyrrolopyridine moieties containing a cytotoxic moiety on the head position may be afforded. This approach may be adapted to other compounds which are described herein. In Scheme 6, FIG. 9, the introduction of an ethylene glycol linker at the head position which is substituted with an azide may be reacted with the functionalized acetylenic intermediate such that a triazine connector molecule is formed optionally containing a second ethylene glycol linker as depicted. Alternatives to this approach may be readily provided by facile modification of the chemistry depicted in Scheme 6 hereof.

Other chemical syntheses of all of the compounds described herein are readily adapted from the synthetic schemes described or alternatively, from chemical synthetic schemes which are presented in WO 2010/052344 and WO 2012/068366, which references are incorporated herein to provide a variety of modified VICB moieties. To these VICB moieties may be attached a linker moiety and an optional connector moiety which are further condensed through a labile linker as otherwise described herein onto a cytotoxic moiety to provide all of the CDM-H compounds according to the present invention.

The above-described chemical schemes provide exemplary syntheses of compounds according to the present invention with various iterations of same provided by analogy using well known methods as described herein and as understood by those of ordinary skill in the art. It is noted that the experimental section provides significant detail to allow the facile synthesis of a variety of bifunctional compounds as otherwise described herein. It is noted that the schemes which are provided are not to be considered limiting in setting forth teachings which provide compounds according to the present invention.

While specific analogs have been shown and described, the present invention is not limited to these specific analogs and other cytotoxic agents that can function to eliminate HIV infected CD4 cells connected by a (labile) linker to a binding terminus (VICB) that will bind to the HIV glycoprotein gp120 (gp120 on the viral membrane as well as gp120 displayed on infected cells), would fall within the scope of the present invention. All of these compounds can be formulated into pharmaceutical compositions as otherwise described herein and used in the methods which are presented.

DETAILED SYNTHETIC INFORMATION AND BIOLOGICAL EXPERIMENTAL SECTION

Abbreviations Used

AcOH=acetic acid
Boc=tert-butoxycarbonyl
BSA=bovine serum albumin
DCM=dichloromethane
DEPBT=3-(Diethoxyphosphorylloxy)-1,2,3-benzotriazin-4-(3H)-one
DIPEA=N,N-diisopropylethylamine
DMF=N,N-dimethylformamide
DMSO=dimethylsulfoxide
DNP=2,4-dinitrophenyl
DPBS=Dulbecco's phosphate-buffered saline
EDC=1-ethyl-3-(3-dimethylaminopropyl) carbodiimide
EtOAc=ethyl acetate
Fmoc=9-fluorenylmethyloxycarbonyl
HI-FBS=heat inactivated fetal bovine serum
HOBt=hydroxybenzotriazole
MeCN=acetonitrile
MeOH=methanol
MW=microwave reactor
NaAsc=sodium ascorbate
pyr=pyridine
tBuOH=t-butanol
TEA=triethylamine
TFA=trifluoroacetic acid
THF=tetrahydrofurane Materials and General Information Purchased starting materials were used as received unless otherwise noted. All moisture sensitive reactions were performed in an inert, dry atmosphere of nitrogen in flame dried glassware. Reagent grade solvents were used for extractions and flash chromatography. Reaction progress was checked by analytical thin-layer chromatography (TLC, Merck silica gel 60 F-254 plates). The plates were monitored either with UV illumination, or by charring with anisaldehyde (2.5% p-anisaldehyde, 1% AcOH, 3.5% $H_2SO_4$(conc.) in 95% EtOH) or ninhydrin (0.3% ninhydrin (w/v), 97:3 EtOH-AcOH) stains. Flash column chromatography was performed using silica gel (230-400 mesh). The solvent compositions reported for all chromatographic separations are on a volume/volume (v/v) basis. Molecular graphics and analyses were performed with the UCSF Chimera package. Chimera is developed by the Resource for Biocomputing, Visualization, and Informatics at the University of California, San Francisco, funded by grants from the National Institutes of Health National Center for Research Resources (2P41RR001081) and National Institute of General Medical Sciences (9P41GM103311).

Instrumentation $^1$H-NMR spectra were recorded at either 400 or 500 MHz and are reported in parts per million (ppm) on the δ scale relative to solvent as an internal standard (CDCl3=7.26 ppm, DMSO-d6=2.49 ppm, CD3OD=3.30). Data are reported as follows: chemical shift, multiplicity (s=singlet, d=doublet, t=triplet, q=quartet, br=broad, m=multiplet), coupling constants (Hz), and integration. $^{13}$C-NMR spectra were recorded at either 100 or 125 MHz and are reported in parts per million (ppm) on the δ scale relative to solvent as an internal standard (CDCl3=77.0 ppm, DMSO-d6=39.5 ppm, CD3OD=49.0 ppm). Analytical ultra high-performance liquid chromatography/mass spectrometry (UPLC/MS) was performed on a Waters UPLC/MS instrument equipped with a reversephase C18 column (1.7 μm particle size, 2.1 Å~50 mm), dual atmospheric pressure chemical ionization (API)/ electrospray (ESI) mass spectrometry detector, and photodiode array detector. Samples were eluted with a linear gradient of 20% acetonitrile-water containing 0.1% formic acid→100% acetonitrile containing 0.1% formic acid over 3 min, followed by 100% acetonitrile containing 0.1% formic acid for 1 min, at a flow rate of 800 μL/min. High-resolution liquid chromatography-mass spectrometry (HR-LC/MS) was performed on a Waters UPLC/HRMS instrument equipped with a dual API/ESI high-resolution mass spectrometer, and a photodiode array detector. High Pressure Liquid Chromatography (HPLC) using a Dynamax Rainin Solvent Delivery System equipped with a Varian Prostar Detector (Galaxie Chromatography Data System version 1.8.505.5), and absorbance measurements were made at 214 and 254 nm simultaneously. A Waters Xterra Prep MS C18 7.8×150 mm column was used for semi-preparative purifications using a water:acetonitrile (A:B) gradient containing 0.1% TFA at 5.0 mL/min, as specified below for individual compounds. Flash column chromatography (unless otherwise noted) was performed using silica gel (230-400 mesh) using Teledyne Isco CombiFlash Rf 200 equipped with a UV detector and fraction collector. Attenuated total reflectance Fourier transform infrared spectra (ATR-FTIR) were obtained using a Thermo Electron Corporation Nicolet 6700 FTIR spectrometer. Data are represented as follows: frequency of absorption (cm-1), intensity of absorption (s=strong, m=medium, w=weak, br=broad).

volumes) to yield S4.7 as a clear sticky solid (391 mg, 83%). $^1$H NMR (400 MHz, CDCl$_3$) δ 7.66-7.60 (m, 1H), 7.58 (d, J=2.5, 1H), 7.33 (t, J=8.0, 1H), 7.17-7.09 (m, 1H), 4.98 (br s, 1H), 4.19-4.14 (m, 2H), 3.85-3.78 (m, 2H), 3.60 (t, J=5.1, 2H), 3.34 (m, 2H), 1.43 (s, 9H).

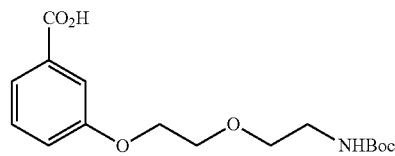 [SMILES: CC(C)(C)OC(=O)NCCOCCOc1cccc(C(=O)O)c1]

(S4.8) A solution of S4.7 (310 mg, 0.91 mmol) in THF (12 mL) and aq. NaOH (2M, 5.7 mL) was heated to reflux for 18 hrs when TLC indicated reaction completion (20:1 CH$_2$Cl$_2$/CH$_3$OH). The solution was acidified to a pH of 1 using 6M aq. HCl and then extracted with CH$_2$Cl$_2$ (3×30 mL). The combined organic layers were dried over anhyd. MgSO$_4$, filtered, and all solvents were evaporated, resulting in S4.8 as a clear viscous oil (293 mg, 99%), which was used without further purification. $^1$H NMR (400 MHz, CDCl$_3$) ä 12.34-10.19 (br s, 1H), 7.77-7.54 (m, 2H), 7.36 (m, 1H), 7.17 (m, 1H), 5.03 (s, 1H), 4.17 (m, 2H), 3.84 (br s, 2H), 3.62 (m, 2H), 3.35 (m, 2H), 1.43 (s, 9H).

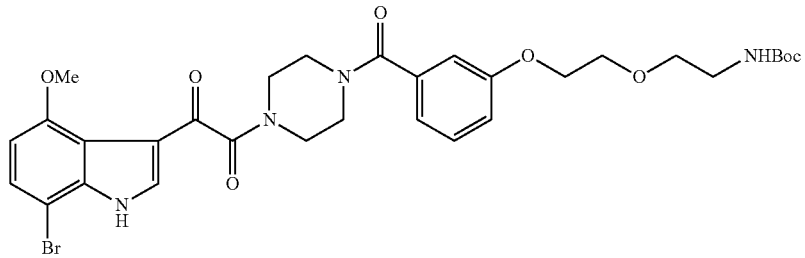 [SMILES: COc1ccc(Br)c2[nH]cc(C(=O)C(=O)N3CCN(C(=O)c4cccc(OCCOCCNC(=O)OC(C)(C)C)c4)CC3)c12]

Figure 4:
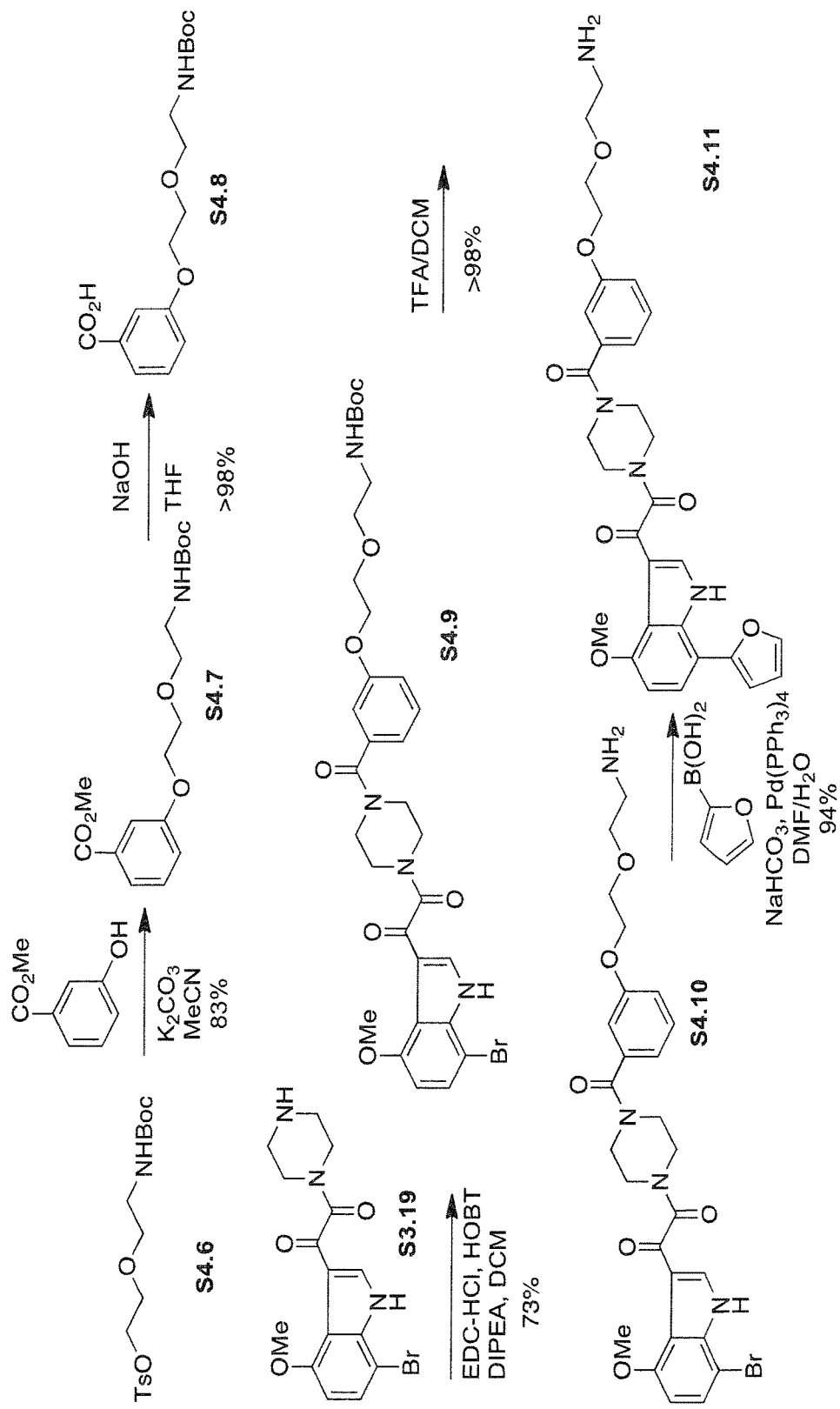
FIG. 4 shows chemical scheme 1 which is directed to the synthesis of amine (S4.11), a precursor to CDM-H 4.19.

Chemical Synthetic Procedures
Following Scheme 1, FIG. 4.

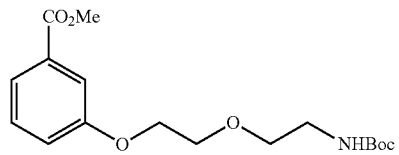

Synthesis of amine (S4.11) precursor to CDM-H 4.18
(S4.7) To a flask equipped with a reflux condenser containing S4.6[52] (500 mg, 1.39 mmol) in MeCN (25 mL), added methyl 3-hydroxybenzoate (243 mg, 1.6 mmol, 1.15 equiv) and K$_2$CO$_3$ (221 mg, 1.6 mmol, 1.15 equiv). Heated to 75° C. under until TLC (5:1 hexanes/EtOAc) indicated reaction completion (18 hrs). Reaction was allowed to cool to RT, then quenched with sat. NH4Cl (30 mL), extracted with DCM (3×40 mL) and then dried over anhyd. MgSO4 and filtered. Volatiles were removed via rotary evaporation and crude S4.7 was purified by flash chromatography (CombiFlash Automated Chromatographer, 24 g column, dryloaded with 4 g pre-packed dry loading column. Run using 100% hexanes to 50% EtOAc in hexanes gradient over 20 column (S4.9) To a flame-dried flask containing a solution of S4.8 (100 mg, 0.307 mmol, 1.1 equiv) in DCM (10 mL), added S3.5a (100 mg, 0.27 mmol), EDC-HCl (48 mg, 0.307 mmol, 1.1 equiv), HOBT (39 mg, 0.307 mmol, 1.1 equiv) and DIPEA (120 uL, 0.81 mmol, 3 equiv). Resulting mixture was stirred at RT for 14 hr when TLC (9:1 DCM/CH$_3$OH) indicated reaction completion. Mixture was diluted with CH$_2$Cl$_2$ (10 mL) and washed with sat. NaHCO$_3$ (15 mL), sat. NH$_4$Cl (15 mL) and brine (15 mL). The combined organic layers were dried over anhyd. MgSO$_4$, filtered, and all solvents were evaporated, resulting in crude S4.9 as a sticky solid. Crude S4.9 was purified by flash chromatography (CombiFlash Automated Chromatographer, 12 g column, dryloaded with 24 g pre-packed dry loading column. Run using 100% DCM to 10% MeOH in DCM gradient over 30 column volumes) to yield S4.9 as a fluffy colorless powder solid (132 mg, 73%). $^1$H NMR (400 MHz, CDCl$_3$) δ 9.77 (s, 1H), 7.93 (s, 1H), 7.36-7.20 (m, 2H), 6.98 (br s, 3H), 6.56 (d, J=8.5, 1H), 5.10-4.90 (br s, 1H), 4.12 (s, 2H), 3.90 (s, 3H), 3.85-3.20 (m, 14H), 1.43 (s, 9H).

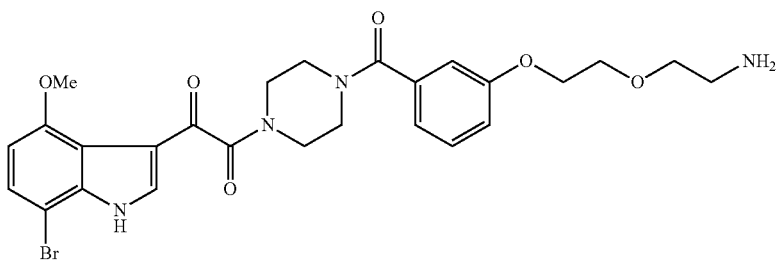 [SMILES: COc1ccc(Br)c2[nH]cc(C(=O)C(=O)N3CCN(C(=O)c4cccc(OCCOCCN)c4)CC3)c12]

(S4.10) To S4.9 (50 mg, 0.074 mmol) in DCM (500 μL) added TFA (333 μL), resulting in a color change from clear to clear-yellow. After 1 hr, TLC indicated reaction completion (9:1 DCM/MeOH). Carefully removed volatiles via rotary evaporation, washing several times with DCM, resulting in crude S4.10 (42 mg, 0.073 mmol, 99%) as a sticky solid, which was used without further purification. $^1$H NMR (400 MHz, MeOD-d$_4$) δ 8.14 (s, 1H), 7.40 (br s, 1H), 7.38 (d, J=8.4, 1H), 6.72 (d, J=8.5, 1H), 4.22 (br s, 2H), 3.99-3.41 (m, 15H), 3.16 (br s, 2H).

and purified crude S4.11 was purified by flash chromatography (CombiFlash Automated Chromatographer, 12 g column, dryloaded with 4 g pre-packed dry loading column. Run using 100% DCM to 10% MeOH in DCM gradient over 15 column volumes, then 10-30% MeOH in DCM over 5 column volumes) to yield S4.11 as a yellow powder (58 mg, 94%). $^1$H NMR (400 MHz, CDCl$_3$) δ 8.03 (s, 1H), 7.51 (s, 1H), 7.41 (d, J=8.1, 1H), 6.94 (br s, 3H), 6.68 (d, J=8.0, 1H), 6.63-6.57 (m, 1H), 6.54-6.38 (m, 1H), 4.11 (br s, 2H), 3.89

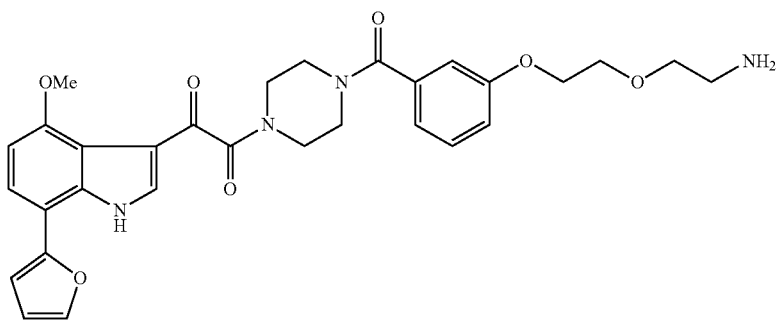 [SMILES: COc1ccc(-c2ccco2)c2[nH]cc(C(=O)C(=O)N3CCN(C(=O)c4cccc(OCCOCCN)c4)CC3)c12]

(S4.11) To a solution of S4.10 (74 mg, 0.11 mmol) in DMF (3.0 mL)/H$_2$O (1.8 mL) in a microwave vial, added NaHCO$_3$ (12.8 mg, 0.153 mmol, 1.4 equiv) and 2-furanylbornic acid (17.1 mg, 0.153 mmol, 1.4 equiv). Removed O$_2$ from solution by bubbling with N$_2$ for at least 10 min. Carefully added Pd(PPh$_3$)$_4$ (6.3 mg, 5.46 μmol, 5 mol %), capped vial and heated in a microwave reactor for 15 min at 150° C. when UPLC/MS indicated consumption of starting material and formation of product. Evaporated all solvents (s, 3H), 3.85-3.20 (m, 12H), 3.06 (s, 2H). UPLC/HRMS (ESI+) calc'd for [M+H]$^+$ C$_{30}$H$_{33}$N$_4$O$_7^+$ 561.2344, found 561.2398.

Figure 5:
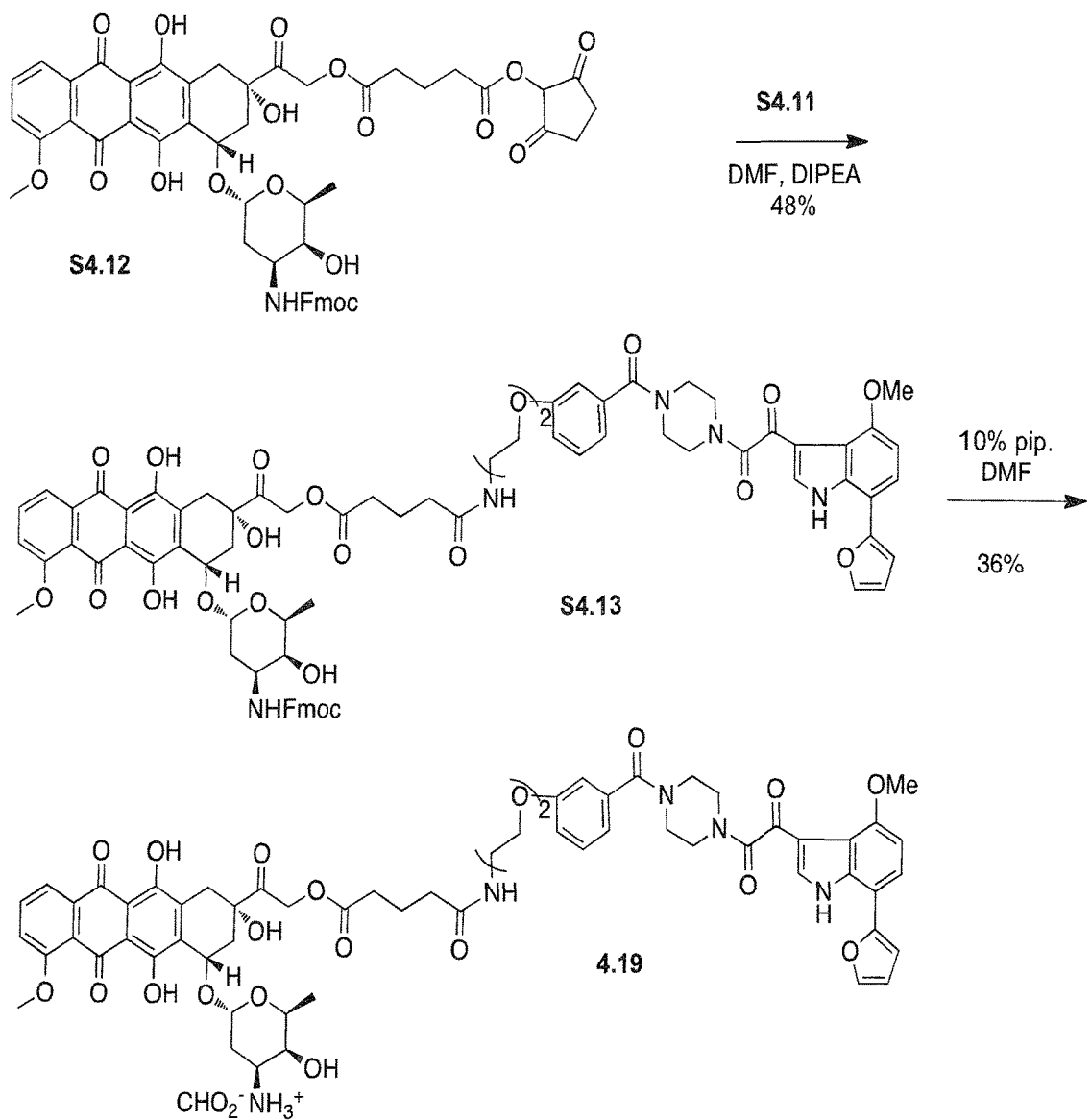
FIG. 5 shows chemical scheme 2 which is directed to the final steps to produce CDM-H 4.19 from aming S4.11 and known NHS-ester S4.12 as indicated.

Scheme 2, FIG. 5—

Final Assembly of CDM-H 4.19 from amine S4.11 and known NHS-ester S4.12.

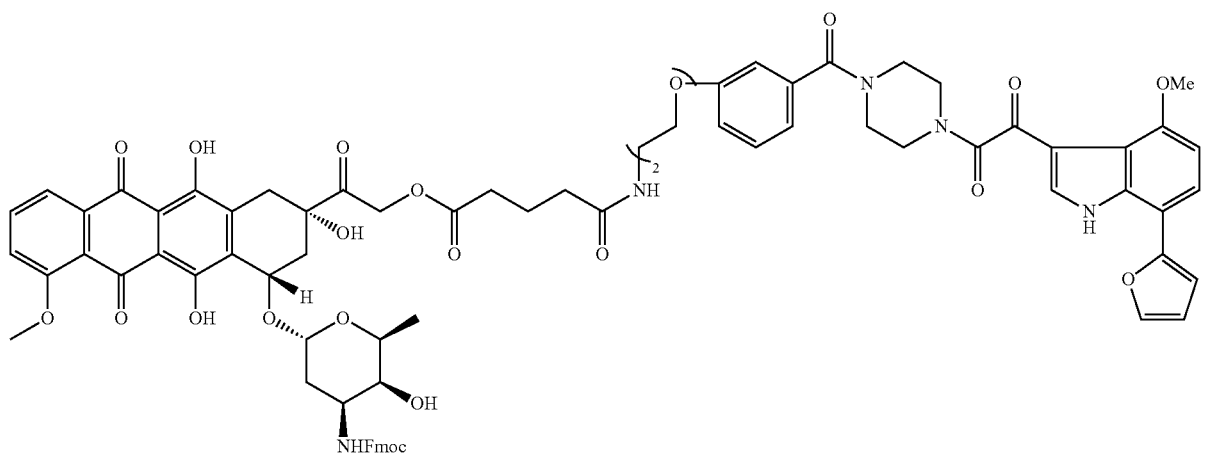

(S4.13) To a flame-dried flask containing S4.12[38] (27 mg, 0.028 mmol) dissolved in anhydrous DMF (2.2 mL), added S4.11 (38 mg, 0.068 mmol, 2.4 equiv), resulting in a light-red homogenous solution that was stirred at RT under an atmosphere of nitrogen. After approximately 4 hrs, added DIPEA (8 µL), resulting in a color change to dark red. Within 1 hr, UPLC/MS indicated consumption of starting material and formation of product mass. Volatiles were carefully removed via rotary evaporation and crude S4.13 was purified by flash chromatography (CombiFlash Automated Chromatographer, 12 g column, dryloaded with 4 g pre-packed dry loading column. Run using 100% DCM to 7% MeOH in DCM gradient over 40 column volumes, then 20% MeOH flush) to yield S4.13 as a red residue (19 mg, 48%). $^1$H NMR (500 MHz, CDCl$_3$) δ 14.15-13.64 (m, 1H), 13.31-13.00 (m, 1H), 10.34-9.61 (m, 2H), 8.14-7.95 (m, 2H), 7.91-7.28 (m, 11H), 7.18-6.81 (m, 4H), 6.77-6.29 (m, 4H), 5.51-5.33 (m, 2H), 5.25-4.98 (m, 3H), 4.84-4.53 (m, 2H), 4.41-4.26 (br s, 2H), 4.26-4.00 (m, 6H), 3.94-3.18 (m, 18H), 3.05-2.80 (m, 1H), 2.71-1.71 (m, 10H), 1.43-1.10 (m, 5H). UPLC/HRMS (ESI+) calc'd for [M+H]$^+$ C$_{77}$H$_{76}$N$_5$O$_{22}$$^+$ 1422.4976, found 1422.4956, t$_R$ 1.86 min.

2.10-1.89 (m, 3H), 1.36-1.11 (m, 5H). Note: sample contaminated with formate salt. UPLC/HRMS (ESI+) calc'd for [M+H]$^+$ C$_{62}$H$_{66}$N$_5$O$_{20}$+1200.4296, found 1200.4299, t$_R$ 1.41 min.

Following Scheme 3, FIG. 6.

Final assembly of CDM-H 4.20 from thiol S4.14 and known maleimide S4.15.

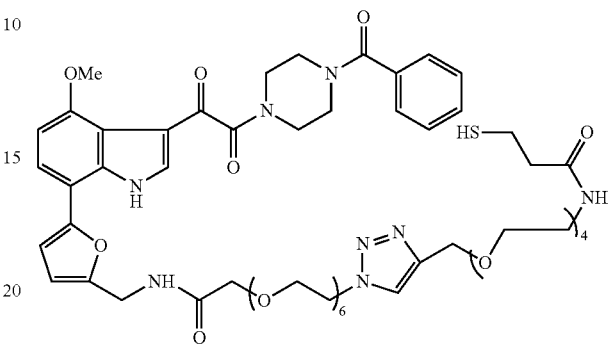

(S4.14) To a flame-dried flask containing a solution of S3.37 (55 mg, 0.053 mmol; in DCM (1 mL), added 3-mercaptanioc acid (11.5 mg, 7.9 µL 0.11 mmol, 2 equiv),

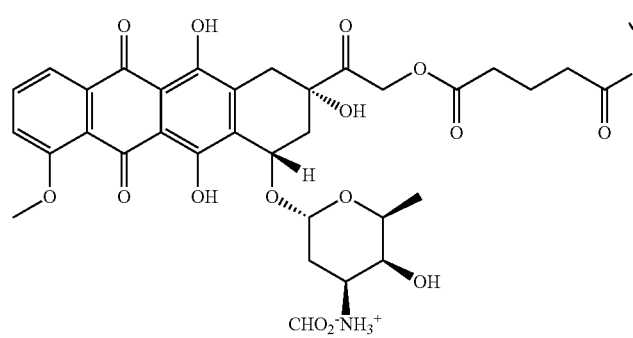

(4.19) To a flame-dried flask containing a solution of S4.13 (19 mg, 0.013 mmol) in anhyd. DMF (1 mL), added piperadine (100 µL), resulting in a color change from red to purple/blue. After 2.5 hrs, UPLC/MS indicated the formation of Fmoc-deprotected product and consumption of starting material. The reaction was quenched with 1% formic acid in DMF drop-wise until reaction solution changed color from blue to red (~500 µL) and volatiles were removed via rotary evaporation. Resulting crude 4.19 was purified by reverse-phase HPLC (0-80% B over 60 min.; Note: 0.1% formic acid substituted for 0.1% TFA for both solvents A and B) and pure fractions were combined and dried via lyophilizer, resulting in pure 4.19 (5.6 mg, 36%) as a red powder. $^1$H NMR (500 MHz, CDCl$_3$) δ 14.06-13.69 (m, 1H), 13.25-12.99 (m, 1H) 10.64-10.47 (m, 1H), 8.02 (br s, 2H), 7.94-7.86 (m, 1H), 7.74-7.65 (m, 1H), 7.55-7.46 (m, 1H), 7.27 (br s, 2H), 7.12-6.89 (m, 2H), 6.60 (br s, 2H), 6.50-6.43 (m, 1H), 5.50-5.42 (m, 1H), 5.35-5.03 (m, 3H), 4.15 (s, 3H), 3.99 (s, 3H), 3.91 (s, 3H), 3.86-3.32 (m, 18H), 3.25-3.14 (m, 2H), 2.92-2.89 (m, 2H), 2.55-2.19 (m, 6H), EDC-HCl (18.5 mg, 0.1 mmol, 1.8 equiv), HOBT (16 mg, 0.1 mmol, 1.8 equiv) and DIPEA (44 uL, 3 equiv). Resulting mixture was stirred at RT for 11 hr when UPLC/MS indicated reaction completion. All solvents were evaporated, resulting in crude S4.14 as a sticky solid, which was purified by flash chromatography (CombiFlash Automated Chromatographer, 4 g column, dryloaded with 4 g pre-packed dry loading column. Run using 100% DCM to 20% MeOH in DCM gradient over 80 column volumes) to yield S4.13 as a sticky solid (19 mg, 30%). $^1$H NMR (500 MHz, CDCl$_3$) δ 11.34 (s, 1H), 8.14 (d, J=3.3, 1H), 8.08 (br s, 1H), 7.69 (s, 1H), 7.49-7.36 (m, 6H), 6.69 (d, J=8.4, 1H), 6.53 (d, J=3.3, 1H), 6.31 (d, J=3.3, 1H), 4.65 (br s, 2H), 4.55 (apparent d, J=6.2, 2H), 4.47-4.43 (m, 2H), 4.04 (br s, 2H), 3.95 (s, 3H), 3.79-3.76 (m, 2H), 3.72-3.34 (m, 44H), 2.78 (dd, J=6.8, 15.1, 2H), 2.48 (t, J=6.8, 2H), 1.62 (t, J=8.3, 1H). UPLC/HRMS (ESI+) calc'd for [M+H]$^+$ C$_{55}$H$_{77}$N$_8$O$_{17}$S$^+$ 1153.5122, found 1153.5189.

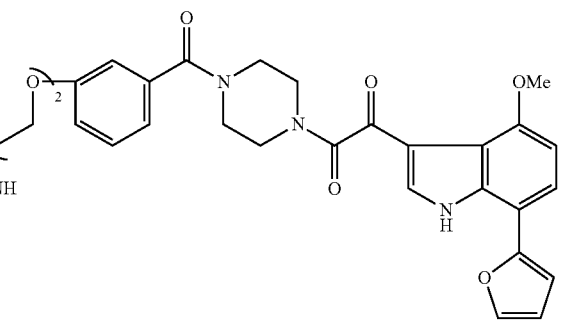

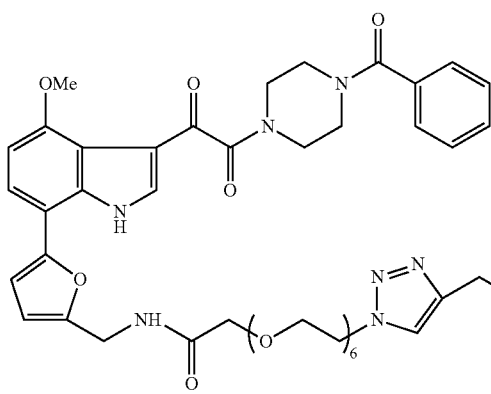
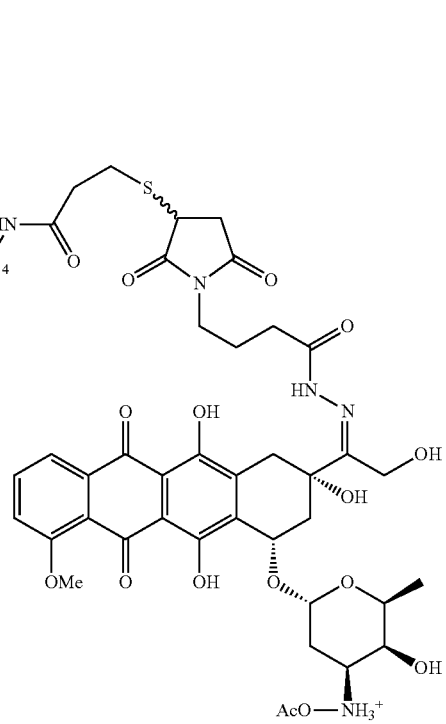

(4.20) To a flame-dried flask containing S4.14 (19 mg, 0.016 mmol) in anhyd. MeOH (600 μL), added S4.15[53, 54] (15.2 mg, 0.018 mmol, 1.12 equiv) followed by DIPEA (0.5 μL), resulting in the formation of a precipitate. Reaction was carefully monitored by UPLC/MS, and after 22 hrs, starting material was consumed and desired mass was detected. Volatiles were removed and crude 4.20 was purified by reverse-phase HPLC where solvent A=30 mM Et$_3$N/AcOH in deionized water, adjusted to pH 6.8; B=MeCN (15-50% B over 46 min, 5 mL/min). Note if non-buffered eluent used (e.g. TFA or formic acid), acyl hydrazone bond hydrolyzes. Pure fractions were immediately combined and lyophilized, resulting in pure (~90%) 4.20 (4 mg, 12%) as a red sticky solid. $^1$H NMR (500 MHz, CDCl$_3$) δ 11.50-11.27 (m, 1H), 10.48-10.16 (m, 1H), 8.25-8.17 (m, 1H), 8.17-8.09 (m, 1H), 8.06-7.94 (m, 1H), 7.80-7.55 (m, 3H), 7.51-7.31 (m, 5H), 6.73-6.61 (m, 1H), 6.56-6.42 (m, 1H), 6.34-6.23 (m, 1H), 5.57-5.42 (m, 1H), 5.31-5.15 (m, 1H), 4.77-4.37 (m, 7H), 4.20-3.07 (m, 41H), 2.64-2.33 (m, 6H), 1.78-1.53 (m, 3H), 1.36-1.25 (m, 2H). Note: sample contaminated with triethylammonium acetate salt. UPLC/HRMS (ESI+) calc'd for [M+H]$^+$ C$_{90}$H$_{115}$N$_{12}$O$_{30}$S$^+$ 1875.7563 and 1876.7596, found 1875.8802 and 1876.8636.

UPLC/HRMS Hydrolytic Half-Life Analysis

In order to examine the hydrolytic stability of various cytotoxic conjugations, UPLC/MS was used to calculate half-life of CDM-H's in DPBS buffer. A solution of test molecule (10 μM) was made in DPBS (Gibco) and incubated at 37° C., 5% CO$_2$ in LC/MS vials for a specified time. The relative ratio of free doxorubicin:CDM-H was determined by integrating the absorbance signal at a wavelength of 490 nm (absorbance maximum of doxorubicin) for doxorubicin and CDM-H, which elute at separate times, using Waters software. UPLC/MS method described in General Information section. Data fitted using one-phase decay model with GraphPad Prism.

% CDM-H=[(Abs of CDM-H)/(Abs of Dox+Abs of CDM-H)]*100

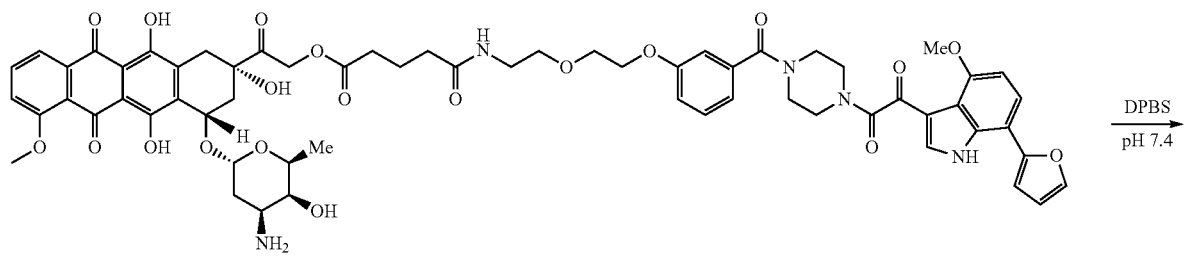

4.19

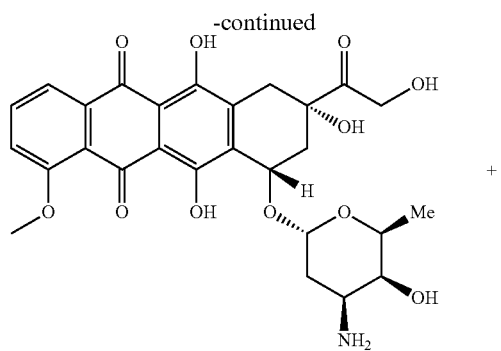
4.18
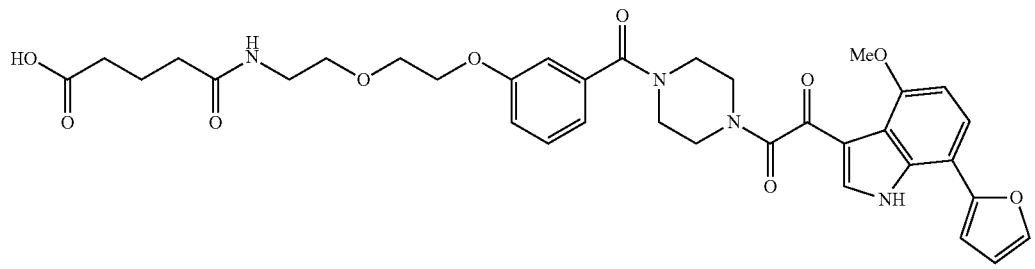
S4.16
Hydrolysis of CDM-H ester 4.19, as detected by UPLC/HR-MS.
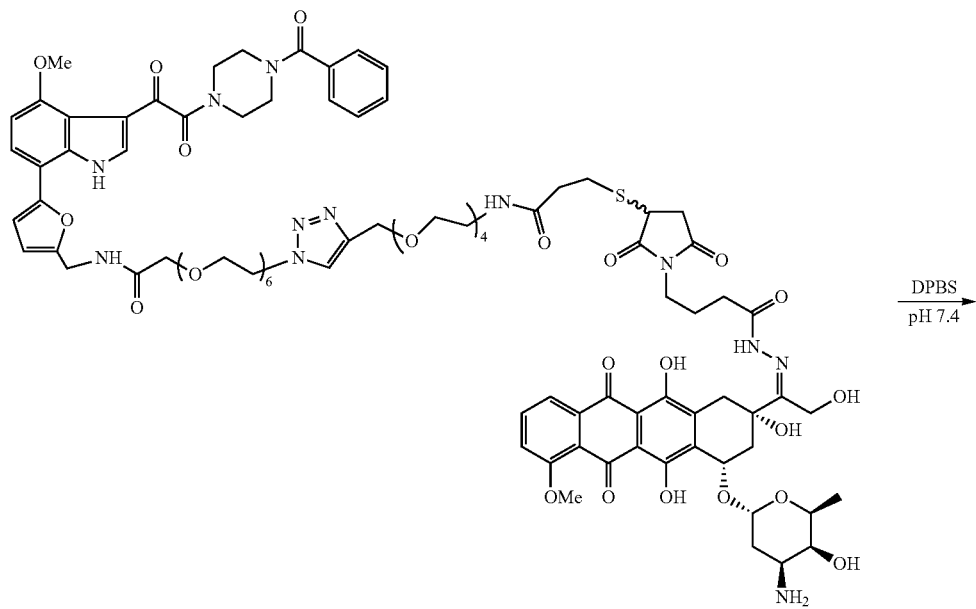
4.20

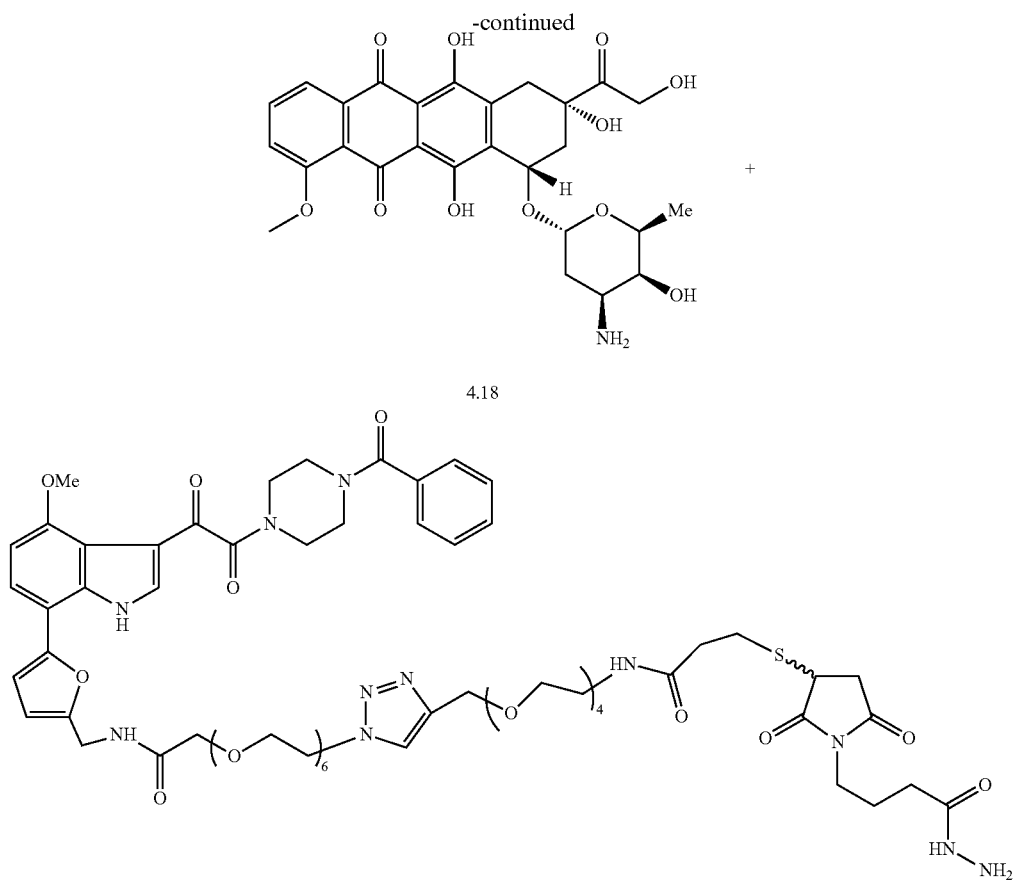

Hydrolysis of CDM-H acyl hydrazone 4.20, as detected by UPLC/HR-MS.

Biology

General Information

All reagents and proteins used are commercially available and used as received unless otherwise noted. Unless otherwise noted, all micro-plate based assays were quantitated using a BioTek Synergy 3 Microplate reader and data was fitted and graphed using GraphPad Prism version 5.00 for Windows (GraphPad Software, San Diego Calif. USA, graphpad.com).

CD4 Inhibition ELISA

CD4 inhibition ELISAs were performed as described below. The ELISA results for CDM-H 4.19 and 4.20 appear in attached FIG. 13 hereof.

This procedure was adapted from our previously reported protocol.[1] 96 well plates (Nunc; Immuno) were coated overnight (12 hr) at 4° C. with soluble recombinant HIV-1 gp120$_{JRFL}$ (Immune Technology; Yonkers, N.Y.) at 1 µg/ml in Buffer C. Plates were washed with DPBS (Gibco, 1×100 µL) and then blocked with Buffer A for 1 hr at room temperature. After washing with Buffer B (3×100 µL), varying concentrations of the inhibitor (including a "no molecule" control) were added simultaneously with recombinant human T-cell CD4 (ImmunoDiagnostics, Inc; Woburn, Mass.) in Buffer A in triplicate so that the final concentration/well of CD4 is 0.1 µg/mL and plates were incubated for 1 hr at room temperature. Plates were washed with Buffer B (3×100 µL) and then incubated with mouse OKT4 anti-CD4 IgG antibody (Biolegend; San Diego, Calif.) at 0.36 µg/ml in Buffer A at RT for 1 hr. Following washes with Buffer B, plates were incubated with horse radish peroxidase (HRP)-conjugated goat anti-mouse antibody (1:2500; Biolegend; San Diego, Calif.). Following washes with Buffer B (3×100 µL), bound antibody was detected with 3,3,5,5-tetramethylbenzidine (TMB, Pierce Protein Research Products), the chromogenic substrate for HPR, and absorbance was read at 450 nm after stopping reaction with 2N $H_2SO_4$ (100 µL). The mean (±SD) of these triplicate samples was then plotted versus inhibitor concentration and a non-linear fit curve was generated using GraphPad Prism. The 50% inhibitory concentration ($IC_{50}$) was defined as the concentration of inhibitor to reduce the amount of bound CD4 to sgp120 by 50% of the maximum bound. Inhibitory assay was performed in triplicate at least two times for each molecule.

(1) Parker, C. G.; Domaoal, R. A.; Anderson, K. S.; Spiegel, D. A., An antibody-recruiting small molecule that targets HIV gp120. *J Am Chem Soc* 2009, 131, 16392-4.

Cell Culture

Wild-type HIV-1 env expressing CHO-env cells and CHO-pSv (env negative isogenic control) were a gift from Dr. Edward Berger (NIH), however, they were developed by Nicholas and coworkers.[55] CHO-pSv cells were grown in DMEM base media described below while CHO-env cells were grown in selection medium, which consists of base medium containing 0.25 µM methotrexate (MTX, Aldrich).
*Note: Decrease in envelope expression in CHO-env cells was observed upon several passages and it is recommended to maintain low passage stocks of cells in liquid nitrogen.
Base Media for CHO Cell Culture
- DMEM—high glucose, glutamate, pyruvate (Gibco, cat #11995)
- 10% MEM-NEAA (Gibco)
- HEPES buffer—10 mM final concentration
- 10% Heat inactivated FBS All cells were cultured in a moist environment at 37° C., 5% $CO_2$. Cells were grown in T-75 tissue culture flasks, and detached with 2.5 mM EDTA/0.5 mM EGTA in DPBS (Gibco) for passage. Cells counted by diluting 10 µL of cell mixture into 90 µL of trypan blue dye, then counting using hemocytometer. All centrifugation was performed at 1000 rpm.

Cell Cytotoxicity Assay (CellTiter Glo)
***Note: all incubations and dilutions in CHO-culture media (+MTX for CHO-env)
***All incubations performed in 96-well plates (clear bottom, black sides; Costar#3603) in triplicate at 37° C., 5% $CO_2$ in moist environment.
*** CD4-PE generous gift from Edward Berger (NIH).

Seeding Plates
Confluent (~80%) T-75 flasks of CHO-env and/or CHO-pSv were washed once with DPBS (3 mL), detached, counted and then centrifuged. Cell pellets were aspirated and then resuspended in full growth media at a cell density of 1.5E5 cells/mL, then aliquoted to 96-well plate (50 µL, 7.5E3 cells/well), covered and incubated for 14 hr.

Addition of Test Compounds
Serial dilutions (1/6) of molecules made in empty 96-well plates using multichannel pipette, and then transferred to plates containing seeded cells (50 µL). Negative control (no molecule) as well as maximum killing control (2.5% Triton X) also prepared. Plates covered and incubated for either 14 hr or 24 hr. Following incubation, 100 uL prepared CellTiter Glo reagent (Promega product#G7571) added as described by provided assay protocol. Luminescence monitored on Biotek Synergy 2 microplate reader.

% cytotoxicity above background calculated by the following formulas:

% CDC=[100−((sample−max kill)/(no molecule−max kill))*100]

Sample means plotted using GraphPad Prism Software±standard deviation (SD).

Cell Cytotoxicity Assay (xCELLigence)[56]
***Note: all incubations and dilutions in CHO-culture media (+MTX for CHO-env)
***All incubations performed in E-plate 16 (Roche) in duplicate at 37° C., 5% $CO_2$ in moist environment.
*** CD4-PE generous gift from Edward Berger (NIH).

The xCELLigence System (model RTCA-DP Roche; RTCA software v1.2) is a tool designed to measure cell density, viability, and morphology in real time via impedance measurements. Tissue culture wells are coated with gold electrodes, which forms a circuit when the well is filled with medium. When a cell rests on the electrodes, impedance is increased and is related to a "cell index," and cell indices increase as cells adhere to a greater fraction of the well (E-plate). Accordingly, a higher cell index value indicates a higher viability, cell number, or a more spread out morphology. When these cells die, they become detached, and as a result, the cell indices decrease. Changes in cell indices can then be converted to changes in cell viability:

% specific killing=100−[(cell index)/(normal growth index)]×100

Cell Preparation
Confluent (~80%) T-75 flasks of CHO-env and/or CHO-pSv were washed once with DPBS (3 mL), detached, counted and then centrifuged. Cell pellets were aspirated and then resuspended in full growth media at a cell density of 1.25E5 cells/mL.

xCelligence Setup
In order to establish a background impedance of growth media, 200 µL of respective growth medium was added to all wells of E-plate and background reading was saved. Cells then aliquoted to E-plate (100 µL, 12.5E3 cells/well), covered and incubated 22 hrs to established an exponential growth curve, scanning once every 15 minutes. In order to examine the cytotoxicity of test compounds, 100 µL of media carefully removed from E-plates containing attached cells and replaced with either 100 µL of fresh media containing vehicle (i.e. DMSO) or 100 µL media containing 20 µM of test compound (or 2 µg/mL CD4-PE). The cellular indices were then monitored over 120 hrs, scanning once every 15 minute interval. To wells receiving undergoing "recycling" or receiving multiple additions, 100 µL of solution was removed and replenished with fresh media containing compound or vehicle. The raw raw xCelligence data of CDM-Hs 4.19 and 4.20, doxorubicin (4.18) and CD4-PE when incubated with CHO-env (gp120+) and CHO-pSv (gp120−) cells appears in FIG. 17 hereof.

Immunofluorescence Microscopy
***Note: all incubations and dilutions in CHO-culture media (+MTX for CHO-env)
***All incubations performed in duplicate at 37° C., 5% $CO_2$ in moist environment.

Confluent (~80%) T-75 flasks of CHO-env and/or CHO-pSv were washed once with DPBS (3 mL), detached, counted and then centrifuged. Cell pellets were aspirated and then resuspended in full growth media at a cell density of 1.5E5 cells/mL. Cell suspension then aliquoted (300 µL, 3E5 cells/well) to wells of 8-well slide chamber (LabTek, #12565470, 15411). Cells then allowed to adhere and grow to confluency (~80%), which takes approximately 40 hrs. Media carefully aspirated and cells were gently washed with DPBS (300 µL) to remove dead cells. Media containing test molecule (CDM-H or doxorubicin, 10 µM) was added to cells and incubated for 1 hr. Media carefully aspirated and cells were gently washed with DPBS (300 µL). Media containing LysoTracker Blue fluorescent dye (Invitrogen, cat#L7525), or nothing, was added to cells and incubated in accordance with protocol provided. Media carefully aspirated and cells were gently washed with DPBS (300 µL), then resuspended in media and fluorescence micrographs were taken with a Zeiss Axiovert 200M fluorescence microscope equipped with Cy3 and DAPI filter sets. Note: for time-course experiments, media containing test molecules not removed, and images were taken over time period. FIG. 16 shows the fluorescence micrographs when CDM-H 4.20 or doxorubicin (4.18) is incubated with CHO-env cells after 10 min (A-B) or 20 hrs (C-D) and CHO-pSv cells (E-H). Formation of fluorescent particles, specifically after long incubation periods, suggests the formation of micelles.

Dynamic Light Scattering (DLS)
Dynamic light scattering is an analytical tool that can be used to determine the size distribution profile of small particles in solution. When light hits particles in solution, it scatters in all directions, resulting in a time-dependent fluctuation in the scattering intensity. This fluctuation is due to the fact that the small molecules in solution are undergoing Brownian motion, and so the distance between scatterings in the solution is constantly changing with time. It is from this fluctuation in intensity from which information about the dynamic time scale of movement and size can be obtained. How rapidly the intensity fluctuates over time is represented by an autocorrelation function. At short time intervals, the correlation is high because the particles do not move significantly from the initial state that they were in. The two signals are thus essentially unchanged when compared after only a very short time interval. As the time intervals of measurement become longer, the correlation decays exponentially, meaning that, after a long time period has elapsed, there is no correlation between the scattered intensity of the initial and final states. This exponential decay is related to the motion of the particles, specifically to the diffusion coefficient. Thus, particles that are larger will have slower movements, thus at longer times, there will be more correlation between the scattered intensity of the initial and final states, as compared to smaller particles.[57]

Figure 18:
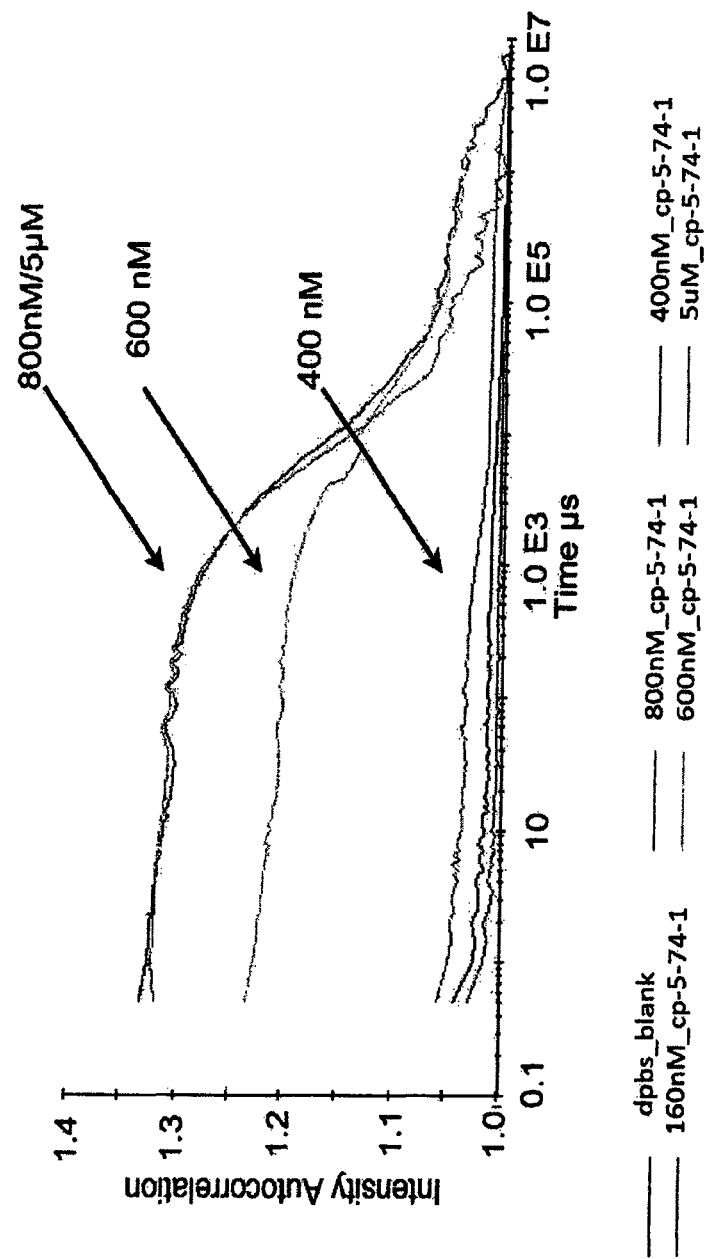
FIG. 18 shows the preliminary dynamic light scattering (DLS) experiment to detect aggregate formation.

The Yale School of Medicine Keck facility possesses a DLS instrument in their Biophysical Resource Laboratory. As a preliminary confirmation that CDM-H 4.20 is forming aggregates in a concentration dependent manner and at the concentrations used in the described cytotoxicity assays, we examined its scattering profile in collaboration with Ewa Folta-Stogniew at the Keck center. Thus, following protocols provided by the resource center, we performed DLS experiments of 4.20 in DPBS at various concentrations. As shown in Figure S4.7, there is a significant increase in autocorrelation as a function of concentration. In addition, at longer time intervals, there is significantly higher autocorrelations at higher concentrations of 4.20 than at lower concentrations, suggesting that at higher concentrations, aggregation is taking place. These observations are consistent with the hypothesis that 4.20 is indeed forming aggregates and, thus, further investigation and/or optimization of 4.20 (in order to circumnavigate aggregation) is warranted. FIG. 18 shows the preliminary dynamic light scattering (DLS) experiment to detect aggregate formation.

SUMMARY

The present invention meets the strategic need for a new treatment for HIV infection by providing bifunctional small molecules generally referred to as ARM-HI's which function through orthogonal pathways—both by inhibition the gp120-CD4 interaction, and by recruiting anti-DNP antibodies to gp120-expressing cells—in preventing the cell infection and spread of HIV. It is shown that: ARM-HI's according to the present invention exhibit substantially greater activity than ARM-H compounds previously published.

The present antiviral approach has distinct advantages over other small-molecule, protein, and vaccine-based anti-HIV strategies.

Although the human immune response has been demonstrated to generate neutralizing anti-gp120 antibodies around which the virus does not effectively mutate, vaccine-based approaches toward inducing such antibodies in human hosts have not yet proven successful. In theory, although the HIV virus mutates extremely rapidly in human hosts, since it must retain CD4-binding activity in order to remain infectious, antibody-recruiting small molecules that mimic the CD4 recognition motif such as the ARM-HI's of the invention have the hope of serving the same functional role as neutralizing anti-gp120 antibodies. Furthermore, as small molecules, these materials likely possess substantial advantages over protein-based therapeutics including low propensity for immunogenicity, high metabolic stability, ready large-scale production, and relatively low cost.

The evidence suggests that a cellular immune response is necessary for viral inactivation in vivo, and the bifunctional small molecules of the invention have been shown to directly target gp120-expressing particles to macrophages and neutophils.

This approach to antiviral therapy is also ideal as a prophylactic, as the bifunctional compound are not be expected to have any significant adverse side effects, being only active when virus is present.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

REFERENCES

1. Volberding, P. A.; Deeks, S. G., Antiretroviral therapy and management of HIV infection. *Lancet* 2010, 376, 49-62.
2. Le Douce, V.; Janossy, A.; Hallay, H.; Ali, S.; Riclet, R.; Rohr, O.; Schwartz, C., Achieving a cure for HIV infection: do we have reasons to be optimistic? *J Antimicrob Chemother* 2012, 67, 1063-74.
3. Finzi, D.; Hermankova, M.; Pierson, T.; Carruth, L. M.; Buck, C.; Chaisson, R. E.; Quinn, T. C.; Chadwick, K.; Margolick, J.; Brookmeyer, R.; Gallant, J.; Markowitz, M.; Ho, D. D.; Richman, D. D.; Siliciano, R. F., Identification of a reservoir for HIV-1 in patients on highly active antiretroviral therapy. *Science* 1997, 278, 1295-300.
4. Wong, J. K.; Hezareh, M.; Gunthard, H. F.; Havlir, D. V.; Ignacio, C. C.; Spina, C. A.; Richman, D. D., Recovery of replication-competent HIV despite prolonged suppression of plasma viremia. *Science* 1997, 278, 1291-5.
5. Carter, C. C.; Onafuwa-Nuga, A.; McNamara, L. A.; Riddell, J. t.; Bixby, D.; Savona, M. R.; Collins, K. L., HIV-1 infects multipotent progenitor cells causing cell death and establishing latent cellular reservoirs. *Nat Med* 2010, 16, 446-51.
6. Walker, B. D.; Burton, D. R., Toward an AIDS vaccine. *Science* 2008, 320, 760-4.
7. Berger, E. A.; Pastan, I., Immunotoxin complementation of HAART to deplete persisting HIV-infected cell reservoirs. *PLoS Pathog* 2010, 6, e1000803.
8. Chaudhary, V. K.; Mizukami, T.; Fuerst, T. R.; FitzGerald, D. J.; Moss, B.; Pastan, I.; Berger, E. A., Selective killing of HIV-infected cells by recombinant human CD4-Pseudomonas exotoxin hybrid protein. *Nature* 1988, 335, 369-72.

9. Berger, E. A.; Chaudhary, V. K.; Clouse, K. A.; Jaraquemada, D.; Nicholas, J. A.; Rubino, K. L.; Fitzgerald, D. J.; Pastan, I.; Moss, B., Recombinant CD4-*Pseudomonas* exotoxin hybrid protein displays HIV-specific cytotoxicity without affecting MHC class II-dependent functions. *AIDS Res Hum Retroviruses* 1990, 6, 795-804.

10. Ashorn, P.; Moss, B.; Berger, E. A., Activity of CD4-*Pseudomonas* exotoxin against cells expressing diverse forms of the HIV and SIV envelope glycoproteins. *J Acquir Immune Defic Syndr* 1992, 5, 70-7.

11. Bera, T. K.; Kennedy, P. E.; Berger, E. A.; Barbas, C. F., 3rd; Pastan, I., Specific killing of HIV-infected lymphocytes by a recombinant immunotoxin directed against the HIV-1 envelope glycoprotein. *Mol Med* 1998, 4, 384-91.

12. Kennedy, P. E.; Moss, B.; Berger, E. A., Primary HIV-1 isolates refractory to neutralization by soluble CD4 are potently inhibited by CD4-*Pseudomonas* exotoxin. *Virology* 1993, 192, 375-9.

13. Berger, E. A.; Moss, B.; Pastan, I., Reconsidering targeted toxins to eliminate HIV infection: you gotta have HAART. *Proceedings of the National Academy of Sciences of the United States of America* 1998, 95, 11511-3.

14. Berger, E. A.; Pastan, I., Immunotoxin complementation of HAART to deplete persisting HIV-infected cell reservoirs. *PLoS Pathog* 2010, 6, e1000803.

15. Davey, R. T.; Boenning, C. M.; Herpin, B. R.; Batts, D. H.; Metcalf, J. A.; Wathen, L.; Cox, S. R.; Polis, M. A.; Kovacs, J. A.; Falloon, J., Use of recombinant soluble CD4 *Pseudomonas* exotoxin, a novel immunotoxin, for treatment of persons infected with human immunodeficiency virus. *Journal of Infectious Diseases* 1994, 170, 1180-8.

16. Lueders, K. K.; De Rosa, S. C.; Valentin, A.; Pavlakis, G. N.; Roederer, M.; Hamer, D. H., A potent anti-HIV immunotoxin blocks spreading infection by primary HIV type 1 isolates in multiple cell types. *AIDS Res Hum Retroviruses* 2004, 20, 145-50.

17. Goldstein, H.; Pettoello-Mantovani, M.; Bera, T. K.; Pastan, I. H.; Berger, E. A., Chimeric toxins targeted to the human immunodeficiency virus type 1 envelope glycoprotein augment the in vivo activity of combination antiretroviral therapy in thy/liv-SCID-Hu mice. *J Infect Dis* 2000, 181, 921-6.

18. Johansson, S.; Goldenberg, D. M.; Griffiths, G. L.; Wahren, B.; Hinkula, J., Elimination of HIV-1 infection by treatment with a doxorubicin-conjugated anti-envelope antibody. *Aids* 2006, 20, 1911-5.

19. Davey, R. T., Jr.; Boenning, C. M.; Herpin, B. R.; Batts, D. H.; Metcalf, J. A.; Wathen, L.; Cox, S. R.; Polis, M. A.; Kovacs, J. A.; Falloon, J.; et al., Use of recombinant soluble CD4 *Pseudomonas* exotoxin, a novel immunotoxin, for treatment of persons infected with human immunodeficiency virus. *J Infect Dis* 1994, 170, 1180-8.

20. Allen, T. M., Ligand-targeted therapeutics in anticancer therapy. *Nature Reviews Cancer* 2002, 2, 750-763.

21. Weber, C. A.; Mehta, P. J.; Ardito, M.; Moise, L.; Martin, B.; De Groot, A. S., T cell epitope: friend or foe? Immunogenicity of biologics in context. In *Advanced Drug Delivery Reviews,* 2009; Vol. 61, pp 965-76.

22. Hansel, T. T.; Kropshofer, H.; Singer, T.; Mitchell, J. A.; George, A. J. T., The safety and side effects of monoclonal antibodies. *Nature Reviews Drug Discovery* 2010, 9, 325-38.

23. Egan, M. A.; Carruth, L. M.; Rowell, J. F.; Yu, X.; Siliciano, R. F., Human immunodeficiency virus type 1 envelope protein endocytosis mediated by a highly conserved intrinsic internalization signal in the cytoplasmic domain of gp41 is suppressed in the presence of the Pr55gag precursor protein. *J Virol* 1996, 70, 6547-56.

24. Cervantes-Acosta, G.; Lodge, R.; Lemay, G.; Cohen, E. A., Influence of human immunodeficiency virus type 1 envelope glycoprotein YXXL endocytosis/polarization signal on viral accessory protein functions. *J Hum Virol* 2001, 4, 249-59.

25. Fultz, P. N.; Vance, P. J.; Endres, M. J.; Tao, B.; Dvorin, J. D.; Davis, I. C.; Lifson, J. D.; Montefiori, D. C.; Marsh, M.; Malim, M. H.; Hoxie, J. A., In vivo attenuation of simian immunodeficiency virus by disruption of a tyrosine-dependent sorting signal in the envelope glycoprotein cytoplasmic tail. *J Virol* 2001, 75, 278-91.

26. Doherty, G. J.; McMahon, H. T., Mechanisms of endocytosis. *Annu Rev Biochem* 2009, 78, 857-902.

27. Rajendran, L.; Knolker, H. J.; Simons, K., Subcellular targeting strategies for drug design and delivery. *Nat Rev Drug Discov* 2010, 9, 29-42.

28. Kovtun, Y. V.; Goldmacher, V. S., Cell killing by antibody-drug conjugates. *Cancer Lett* 2007, 255, 232-40.

29. Luzio, J. P.; Pryor, P. R.; Bright, N. A., Lysosomes: fusion and function. *Nat Rev Mol Cell Biol* 2007, 8, 622-32.

30. King, H. D.; Yurgaitis, D.; Willner, D.; Firestone, R. A.; Yang, M. B.; Lasch, S. J.; Hellstrom, K. E.; Trail, P. A., Monoclonal antibody conjugates of doxorubicin prepared with branched linkers: A novel method for increasing the potency of doxorubicin immunoconjugates. *Bioconjug Chem* 1999, 10, 279-88.

31. Che, C.; Yang, G.; Thiot, C.; Lacoste, M. C.; Currie, J. C.; Demeule, M.; Regina, A.; Beliveau, R.; Castaigne, J. P., New Angiopep-modified doxorubicin (ANG1007) and etoposide (ANG1009) chemotherapeutics with increased brain penetration. *J Med Chem* 2010, 53, 2814-24.

32. Kasiotis, K. M.; Magiatis, P.; Pratsinis, H.; Skaltsounis, A.; Abadji, V.; Charalambous, A.; Moutsatsou, P.; Haroutounian, S. A., Synthesis and biological evaluation of novel daunorubicin-estrogen conjugates. *Steroids* 2001, 66, 785-91.

33. Meyer-Losic, F.; Quinonero, J.; Dubois, V.; Alluis, B.; Dechambre, M.; Michel, M.; Cailler, F.; Fernandez, A. M.; Trouet, A.; Kearsey, J., Improved therapeutic efficacy of doxorubicin through conjugation with a novel peptide drug delivery technology (Vectocell). *J Med Chem* 2006, 49, 6908-16.

34. Kratz, F.; Warnecke, A.; Scheuermann, K.; Stockmar, C.; Schwab, J.; Lazar, P.; Druckes, P.; Esser, N.; Drevs, J.; Rognan, D.; Bissantz, C.; Hinderling, C.; Folkers, G.; Fichtner, I.; Unger, C., Probing the cysteine-34 position of endogenous serum albumin with thiol-binding doxorubicin derivatives. Improved efficacy of an acid-sensitive doxorubicin derivative with specific albumin-binding properties compared to that of the parent compound. *J Med Chem* 2002, 45, 5523-33.

35. Kaneko, T.; Willner, D.; Monkovic, I.; Knipe, J. O.; Braslawsky, G. R.; Greenfield, R. S.; Vyas, D. M., New hydrazone derivatives of adriamycin and their immunoconjugates—a correlation between acid stability and cytotoxicity. *Bioconjug Chem* 1991, 2, 133-41.

36. Lee, C. C.; Cramer, A. T.; Szoka, F. C.; Frechet, J. M. J., An intramolecular cyclization reaction is responsible for the in vivo inefficacy and apparent pH insensitive hydrolysis kinetics of hydrazone carboxylate derivatives of doxorubicin. *Bioconjug Chem* 2006, 17, 1364-1368.

37. Sun, C. Z.; Aspland, S. E.; Ballatore, C.; Castillo, R.; Smith, A. B.; Castellino, A. J., The design, synthesis, and evaluation of two universal doxorubicin-linkers: Prepa- 37. ration of conjugates that retain topoisomerase II activity. *Bioorg Med Chem Lett* 2006, 16, 104-107.
38. Carlson, C. B.; Mowery, P.; Owen, R. M.; Dykhuizen, E. C.; Kiessling, L. L., Selective tumor cell targeting using low-affinity, multivalent interactions. *ACS Chem Biol* 2007, 2, 119-127.
39. Pillay, C. S.; Elliott, E.; Dennison, C., Endolysosomal proteolysis and its regulation. *Biochem J* 2002, 363, 417-29.
40. Ickenstein, L. M.; Edwards, K.; Sjoberg, S.; Carlsson, J.; Gedda, L., A novel I-125-labeled daunorubicin derivative for radionuclide-based cancer therapy. *Nucl Med Biol* 2006, 33, 773-783.
41. Decuzzi, P.; Ferrari, M., The role of specific and non-specific interactions in receptor-mediated endocytosis of nanoparticles. *Biomaterials* 2007, 28, 2915-22.
42. Sahay, G.; Batrakova, E. V.; Kabanov, A. V., Different Internalization Pathways of Polymeric Micelles and Unimers and Their Effects on Vesicular Transport. *Bioconjug Chem* 2008, 19, 2023-2029.
43. Wang, J.; Wang, Y.; Liang, W., Delivery of drugs to cell membranes by encapsulation in PEG-PE micelles. *J Control Release* 2012, 160, 637-51.
44. Alberts, B. J., A.; Lewis, J.; Raff, M.; Roberts, K.; Walter, P., *Molecular Biology of the Cell, 4th ed*. Garland Science: New York, 2002.
45. Arlen, P. A.; Brooks, D. G.; Gao, L. Y.; Vatakis, D.; Brown, H. J.; Zack, J. A., Rapid expression of human immunodeficiency virus following activation of latently infected cells. *J Virol* 2006, 80, 1599-1603.
46. Korin, Y. D.; Brooks, D. G.; Brown, S.; Korotzer, A.; Zack, J. A., Effects of prostratin on T-cell activation and human immunodeficiency virus latency. *J Virol* 2002, 76, 8118-8123.
47. Kulkosky, J.; Culnan, D. M.; Roman, J.; Dornadula, G.; Schnell, M.; Boyd, M. R.; Pomerantz, R. J., Prostratin: activation of latent HIV-1 expression suggests a potential inductive adjuvant therapy for HAART. *Blood* 2001, 98, 3006-15.
48. Wender, P. A.; Kee, J. M.; Warrington, J. M., Practical synthesis of prostratin, DPP, and their analogs, adjuvant leads against latent HIV. *Science* 2008, 320, 649-652.
49. Burke, B.; Brown, H. J.; Marsden, M. D.; Bristol, G.; Vatakis, D. N.; Zack, J. A., Primary cell model for activation-inducible human immunodeficiency virus. *J Virol* 2007, 81, 7424-7434.
50. Marsden, M. D.; Kovochich, M.; Suree, N.; Shimizu, S.; Mehta, R.; Cortado, R.; Bristol, G.; An, D. S.; Zack, J. A., HIV Latency in the Humanized BLT Mouse. *J Virol* 2012, 86, 339-347.
51. Yang, H. C.; Xing, S. F.; Shan, L.; O'Connell, K.; Dinoso, J.; Shen, A. D.; Zhou, Y.; Shrum, C. K.; Han, Y. F.; Liu, J. O.; Zhang, H.; Margolick, J. B.; Siliciano, R. F., Small-molecule screening using a human primary cell model of HIV latency identifies compounds that reverse latency without cellular activation. *J Clin Invest* 2009, 119, 3473-3486.
52. Cruz-Morales, J. A.; Guadarrama, P., Synthesis, characterization and computational modeling of cyclen substituted with dendrimeric branches. Dendrimeric and macrocyclic moieties working together in a collective fashion. *J Mol Struct* 2005, 779, 1-10.
53. Kruger, M.; Beyer, U.; Schumacher, P.; Unger, C.; Zahn, H.; Kratz, F., Synthesis and stability of four maleimide derivatives of the anticancer drug doxorubicin for the preparation of chemoimmunoconjugates. *Chem Pharm Bull* 1997, 45, 399-401.
54. Kratz, F.; Warnecke, A.; Scheuermann, K.; Stockmar, C.; Schwab, J.; Lazar, P.; Druckes, P.; Esser, N.; Drevs, J.; Rognan, D.; Bissantz, C.; Hinderling, C.; Folkers, G.; Fichtner, I.; Unger, C., Probing the cysteine-34 position of endogenous serum albumin with thiol-binding doxorubicin derivatives. Improved efficacy of an acid-sensitive doxorubicin derivative with specific albumin-binding properties compared to that of the parent compound. *J Med Chem* 2002, 45, 5523-5533.
55. Pitts, T. W.; Bohanon, M. J.; Leach, M. F.; Mcquade, T. J.; Marschke, C. K.; Merritt, J. A.; Wierenga, W.; Nicholas, J. A., Soluble Cd-4-Pe40 Is Cytotoxic for a Transfected Mammalian-Cell Line Stably Expressing the Envelope Protein of Human-Immunodeficiency-Virus (Hiv-1), and Cytotoxicity Is Variably Inhibited by the Sera of Hiv-1-Infected Patients. *AIDS Res Hum Retroviruses* 1991, 7, 741-750.
56. Reddy, M. M.; Wilson, R.; Wilson, J.; Connell, S.; Gocke, A.; Hynan, L.; German, D.; Kodadek, T., Identification of Candidate IgG Biomarkers for Alzheimer's Disease via Combinatorial Library Screening. *Cell* (Cambridge, Mass., United States) 2011, 144, 132-142.
57. Berne, B. J. P., R., *Dynamic Light Scattering With Applications to Chemistry, Biology, and Physics*. Dover Publications, Inc: New York, 2000.

The invention claimed is:

1. A compound according to the chemical structure:

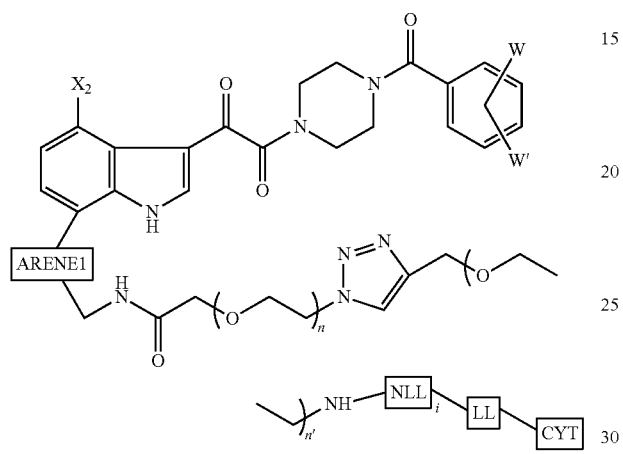

Where $X_2$ is H, $C_1$-$C_6$ alkyl, O—$C_1$-$C_6$ alkyl or halogen;

[ARENE1] is

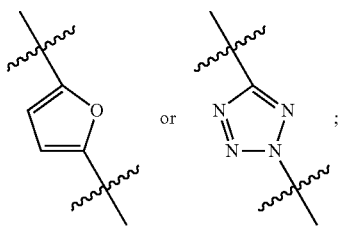 [SMILES: *c1ccc(*)o1 ; *c1nnn(*)n1]

W or W' is each independently H, —$(CH_2)_{n''}$OH, —$(CH_2)_{n''}$COOH, —$(CH_2)_{n''}$O—($C_1$-$C_6$ alkyl), $NO_2$, CN or halogen;

n and n' are each independently 2-8;

Each n" is independently 0, 1, 2, 3, 4, 5, or 6;

i is 0 or 1;

[LL] is a labile linker according to the chemical structure:

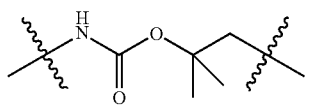

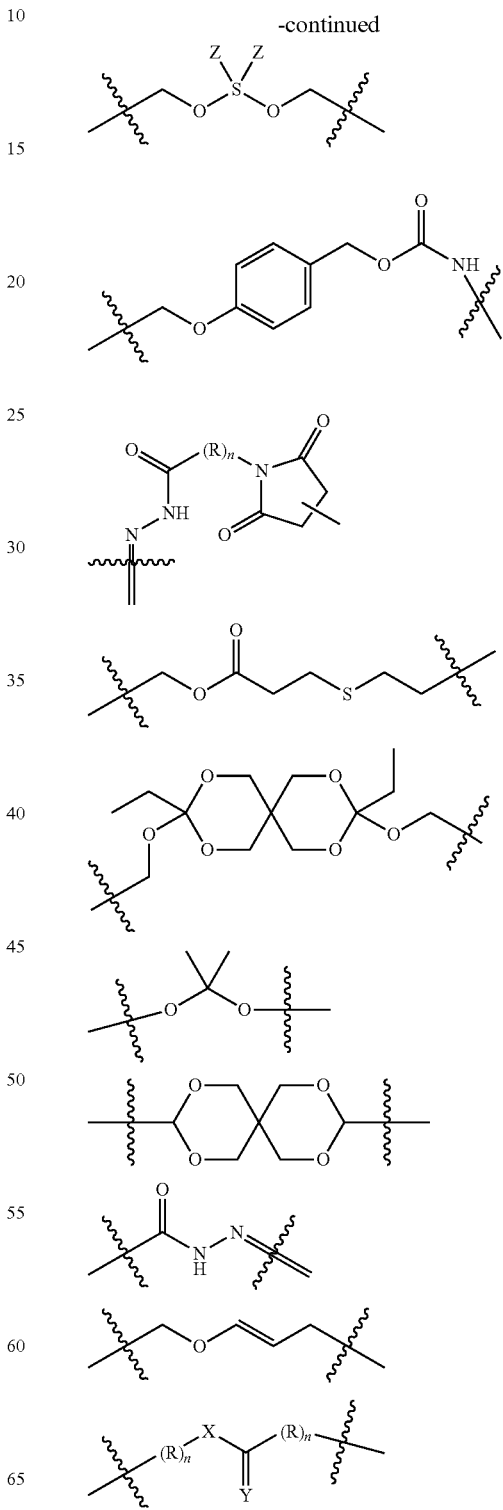

-continued

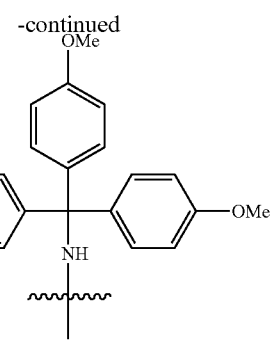

where R is an ethylene glycol group, or a methylene group and n in this labile linker is from 0 to 10;
X is O, N—$R^{AL}$ or S;
$R^{AL}$ is H or a $C_1$-$C_3$ alkyl group;
Y is O or S and
Z=Me, Et, iPr, tBu, Ph, each of which may be optionally substituted with one or more halogen groups and where said Ph group may be further optionally substituted with OMe or a $C_1$-$C_3$ alkyl group which itself may be substituted with up to three halogens; or
[LL] is a group according to the chemical formula:

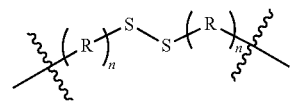

and
R is an ethylene glycol group, or a methylene group and n in this labile linker is from 0 to 10; or [LL] is an enzymatically cleaved labile linker according to the chemical structure:

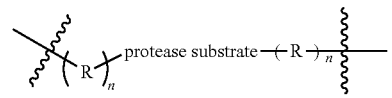

Where the protease substrate is a peptide containing from 2 to 50 amino acid units, and
R is an ethylene glycol group, or a methylene group; and n in this labile linker is from 0 to 10; or
[LL] is a group according to the chemical structure:

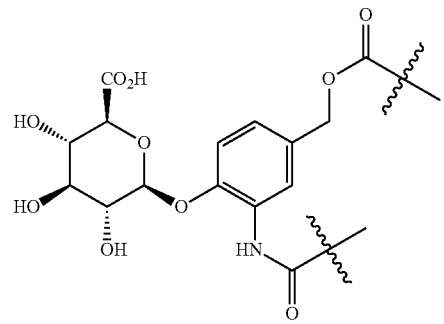 [SMILES: *C(=O)Nc1cc(COC(*)=O)ccc1O[C@@H]1O[C@H](C(=O)O)[C@@H](O)[C@H](O)[C@H]1O]

Where the points of attachment in each of the labile linkers as indicated are joined to other portions of the molecule as indicated;

[NLL] when present is a (poly)ethylene glycol linker of from 2 to 8 ethylene glycol units, or [NLL] is a group:

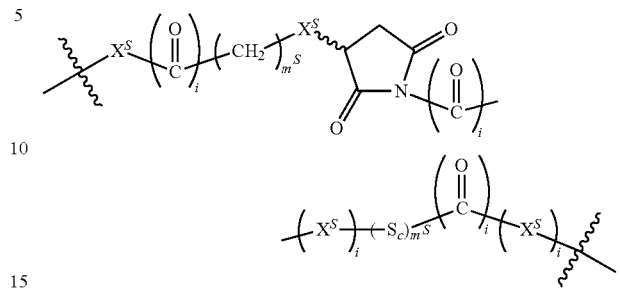

where each $X^S$ is independently S, O or N—$R^S$;
$R^S$ is H or $C_{1-3}$ alkyl;
$S_c$ is $CH_2$; $CH_2O$; or $CH_2CH_2O$;
i is 0 or 1; and
$m^S$ is 0, 1, 2, 3, 4, 5, or 6; and
[CYT] is a group according to the chemical structure:

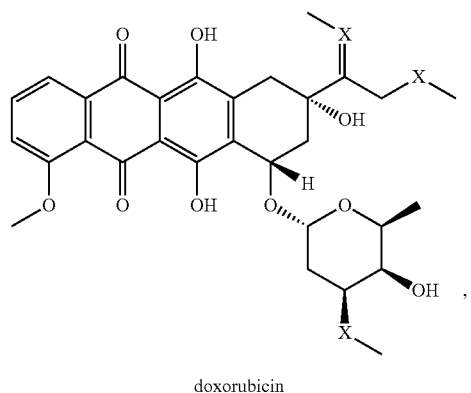

doxorubicin

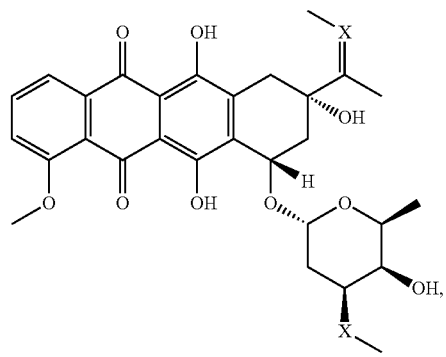

daunorubicin

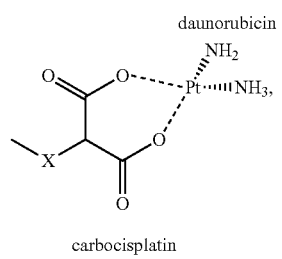

carbocisplatin

93

-continued

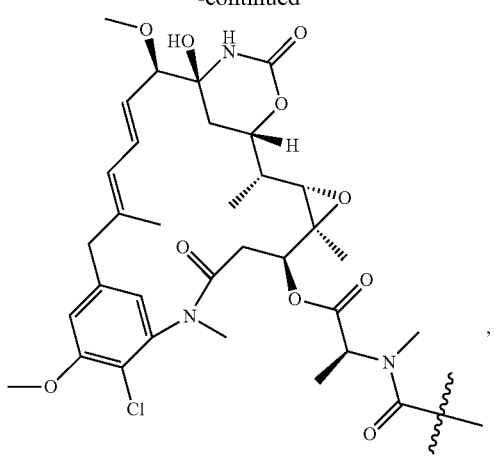

mertansine (DM1)

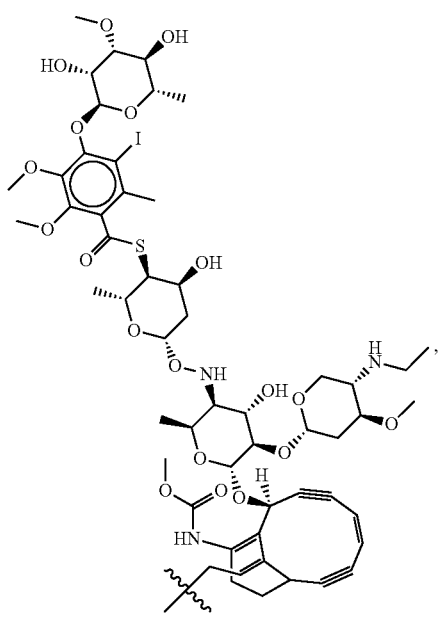

Calicheamicin

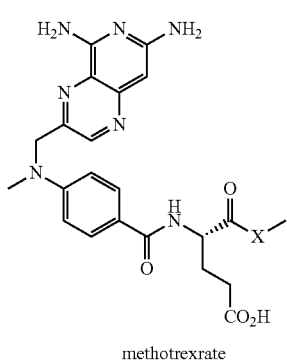

methotrexrate

94

-continued

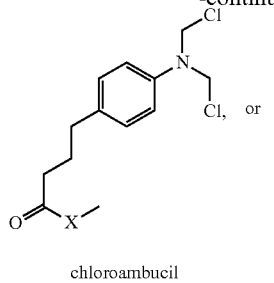

chloroambucil

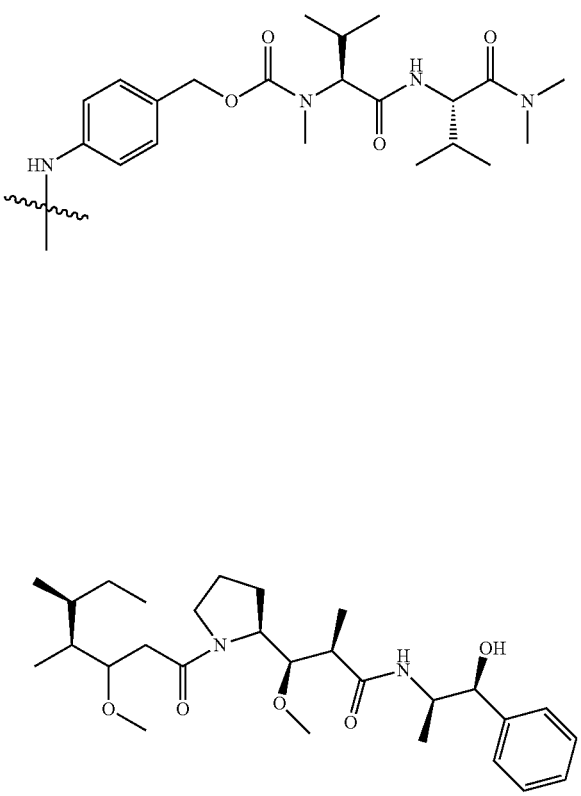

monomethyl auristatin E (MMAE)

wherein X is a group —NR$^{1N}$—, —NR$^{1N}$CO—, —O—, —CH$_2$—, —S—, —OCONH— or —NHCONH— where R$^{1N}$ is H or a C$_1$-C$_3$ alkyl group optionally substituted with one or two hydroxyl groups, and the symbol ⌇ signifies a chemical attachment point of the cytotoxic moiety to a labile linker which is linked through X, or a pharmaceutically acceptable salt or stereoisiomer thereof.

2. A compound according to claim 1 which is
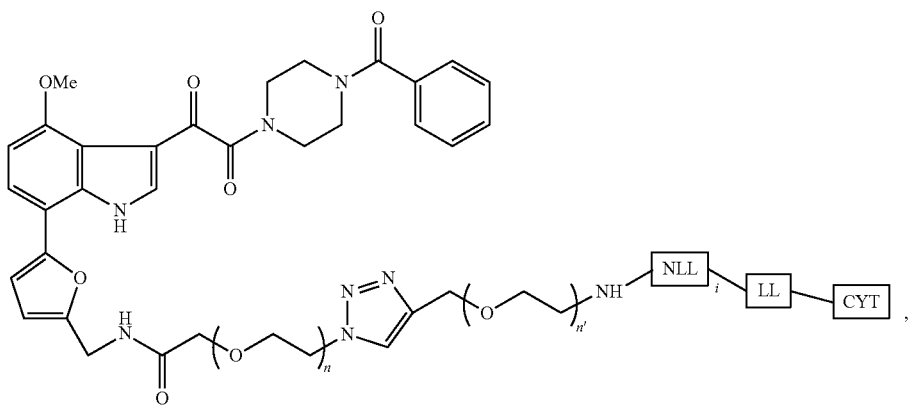
or
a pharmaceutically acceptable salt or stereoisomer thereof.
3. The compound according to claim 2 wherein CYT is doxorubicin or daunorubicin.
4. The compound according to claim 3 wherein CYT is doxorubicin.
5. The compound according to claim 3 wherein CYT is daunorubicin.
6. A compound according to the chemical structure:
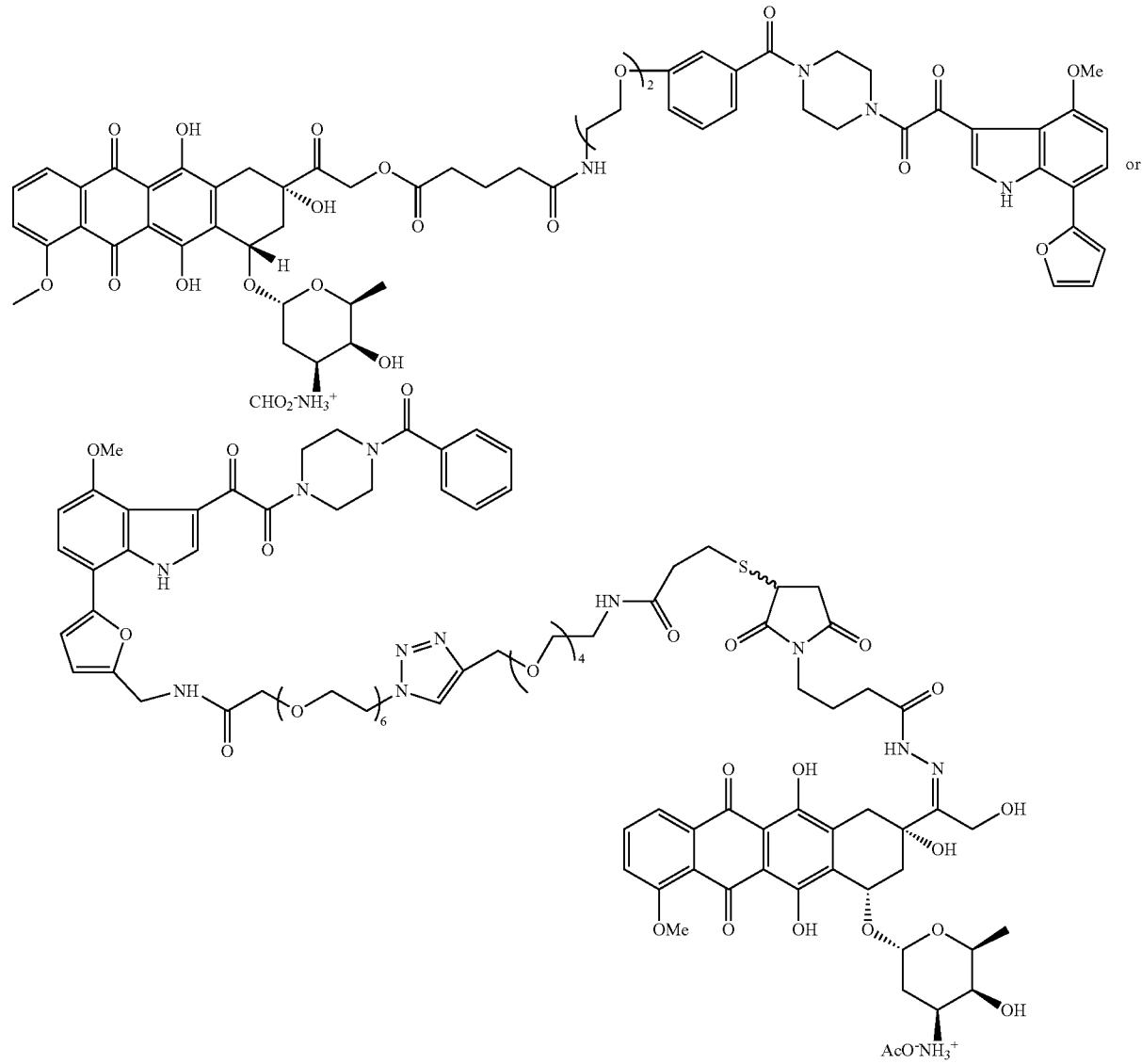

or the free amine or alternative pharmaceutical salt thereof.

7. A compound according to claim 6 having the chemical structure:

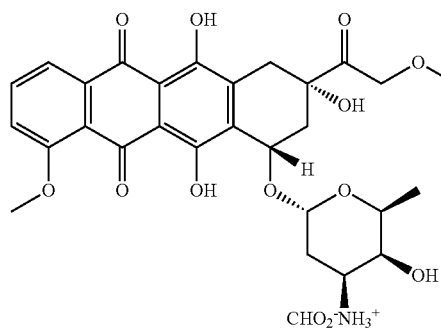

or the free amine or alternative pharmaceutical salt thereof.

8. A compound of claim 6 having the chemical structure:

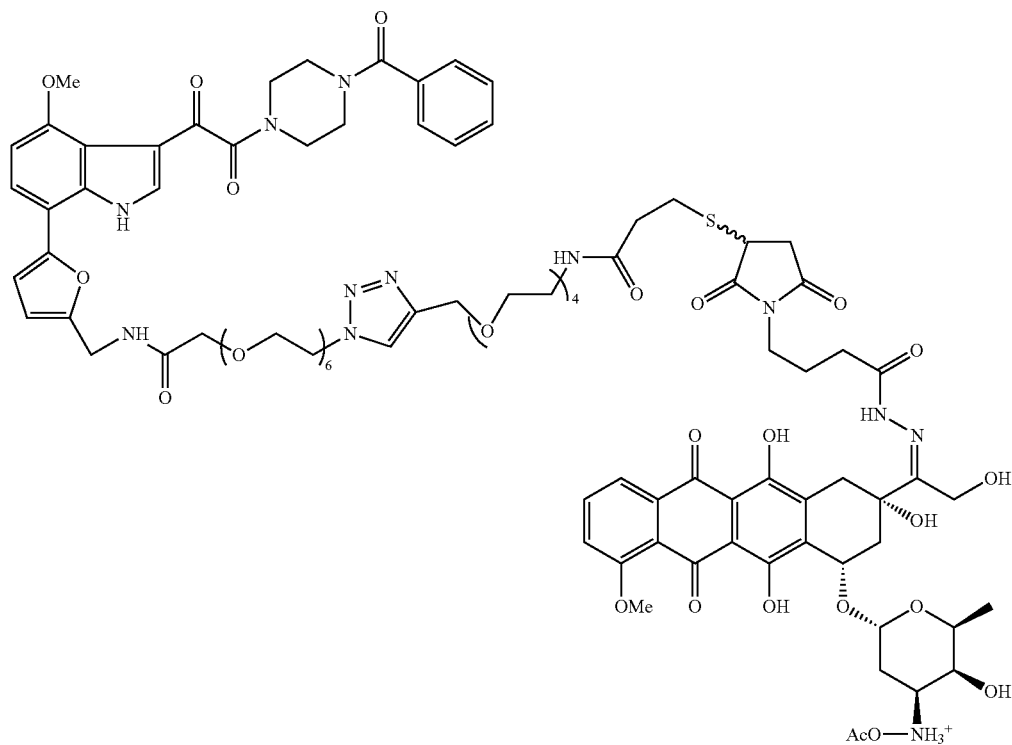

or the free amine or alternative pharmaceutical salt thereof.

9. A pharmaceutical composition comprising an effective amount of a compound according to claim 1 in combination with a pharmaceutically acceptable carrier, additive or excipient.

10. A pharmaceutical composition comprising an effective amount of a compound according to claim 2 in combination with a pharmaceutically acceptable carrier, additive or excipient.

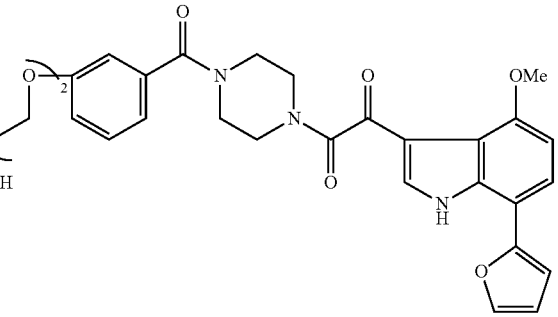

11. A pharmaceutical composition comprising an effective amount of a compound according to claim 3 in combination with a pharmaceutically acceptable carrier, additive or excipient.

12. A pharmaceutical composition comprising an effective amount of a compound according to claim 4 in combination with a pharmaceutically acceptable carrier, additive or excipient.

13. A pharmaceutical composition comprising an effective amount of a compound according to claim 5 in combination with a pharmaceutically acceptable carrier, additive or excipient.

14. A pharmaceutical composition comprising an effective amount of a compound according to claim 6 in combination with a pharmaceutically acceptable carrier, additive or excipient.

15. A pharmaceutical composition comprising an effective amount of a compound according to claim 7 in combination with a pharmaceutically acceptable carrier, additive or excipient.

16. A pharmaceutical composition comprising an effective amount of a compound according to claim 8 in combination with a pharmaceutically acceptable carrier, additive or excipient.

17. The composition according to claim 9 further comprising a latent HIV activator selected from the group consisting of prostratin, bradystatin 1, bryostatin 1, bryostatin 2, IL-7, a histone deacetylase inhibitor, a DNA methylation inhibitor, a compound according to the chemical structure:

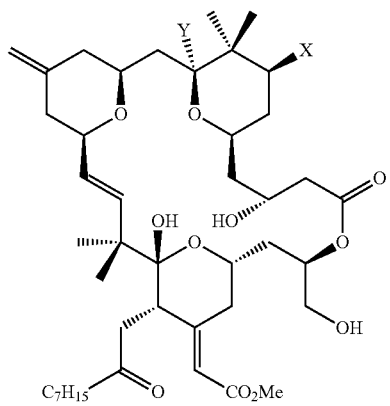

where X and Y are H, X is OH and Y is H, X is OAc and Y is H or X is OAc and Y is OH;
a compound according to the chemical structure:

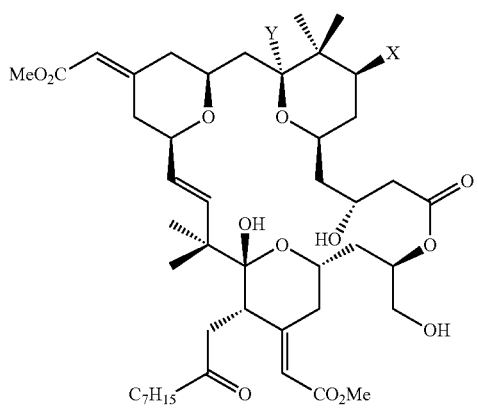

where X and Y are H, X is OAc and Y is H or X is OAc and Y is OH, or a mixture thereof.

18. The composition according to claim 10 further comprising a latent HIV activator selected from the group consisting of prostratin, bradystatin 1, bryostatin 1, bryostatin 2, IL-7, a histone deacetylase inhibitor, a DNA methylation inhibitor, a compound according to the chemical structure:

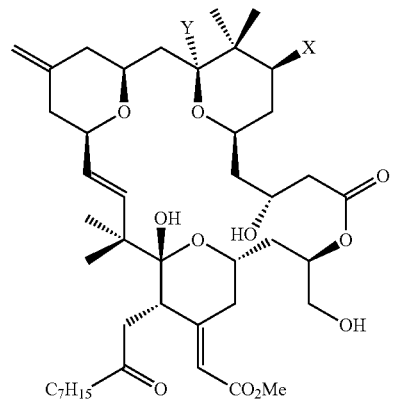

where X and Y are H, X is OH and Y is H, X is OAc and Y is H or X is OAc and Y is OH;
a compound according to the chemical structure:

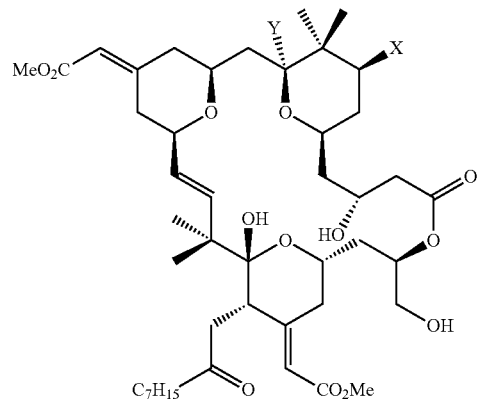

where X and Y are H, X is OAc and Y is H or X is OAc and Y is OH, or a mixture thereof.

19. The composition according to claim 17 wherein said histone deacetylase inhibitor is vorinostat.

20. The composition according to claim 18 wherein said histone deacetylase inhibitor is vorinostat.

21. The composition according to claim 17 wherein said DNA methylation inhibitor is decitabine.

22. The composition according to claim 18 wherein said DNA methylation inhibitor is decitabine.

23. The composition according to claim 9 wherein said composition further comprises an effective amount of an additional anti-HIV agent.

24. The composition according to claim 10 wherein said composition further comprises an effective amount of an additional anti-HIV agent.

25. The composition according to claim 17 wherein said composition further comprises an effective amount of an additional anti-HIV agent.

26. The composition according to claim 18 wherein said composition further comprises an effective amount of an additional anti-HIV agent.

27. The composition according to claim 23 wherein said additional anti-HIV agent is selected from the group consisting of nucleoside reverse transcriptase inhibitors (NRTI), non-nucloeoside reverse transcriptase inhibitors, protease inhibitors and fusion inhibitors.

28. The composition according to claim 24 wherein said additional anti-HIV agent is selected from the group consisting of nucleoside reverse transcriptase inhibitors (NRTI), non-nucleoeoside reverse transcriptase inhibitors, protease inhibitors and fusion inhibitors.

29. The composition according to claim 23 wherein said additional anti-HIV agent is selected from the group consisting of Amprenivir, Abacavir, Acemannan, Acyclovir, AD-439, AD-519, Adefovir dipivoxil, Alpha Interferon, Ansamycin, 097, AR 177, Beta-fluoro-ddA, BMS-232623 (CGP-73547), BMS-234475 (CGP-61755), CI-1012, Cidofovir, Curdlan sulfate, Cytomegalovirus Immune globin, Ganciclovir, Dideoxyinosine, DMP-450, Efavirenz (DMP-266), EL10, Famciclovir, FTC, GS 840, HBY097, Hypericin, Recombinant Human Interferon Beta, Interferon alfa-n3, Indinavir, ISIS-2922, KNI-272, Lamivudine (3TC), Lobucavir, Nelfinavir, Nevirapine, Novapren, Peptide T Octapeptide Sequence, Trisodium Phosphonoformate, PNU-140690, Probucol, RBC-CD4, Ritonavir, Saquinavir, Valaciclovir, Virazole Ribavirin, VX-478, Zalcitabine, Zidovudine (AZT), Tenofovir diisoproxil fumarate salt, Combivir, Abacavir succinate, T-20), AS-101, Bropirimine, CL246, EL10, FP-21399, Gamma Interferon, Granulocyte Macrophage Colony Stimulating Factor (GM-CSF), HIV Core Particle Immunostimulant, Interleukin-2 (IL-2), Immune Globulin Intravenous, IMREG-1, IMREG-2, Imuthiol Diethyl Dithio Carbamate, Alpha-2 Interferon, Methionine-Enkephalin, MTP-PE (Muramyl-Tripeptide), Granulocyte Colony Stimulating Factor (GCSF), Remune, rCD4 (Recombinant Soluble Human CD4-IgG), rCD4-IgG Hybrids, Recombinant Soluble Human CD4, Interferon Alfa 2a, SK&F1-6528, Soluble T4, Thymopentin, Tumor Necrosis Factor (TNF), AK602, Alovudine, Amdoxovir, AMD070, Atazanavir (Reyataz), AVX754 (apricitabine), Bevirimat, BI-201, BMS-378806, BMS-488043, BMS-707035, C31G, Carbopol 974P, Calanolide A, Carrageenan, Cellulose sulfate, Cyanovirin-N, Darunavir, Delavirdine, Didanosine (Videx), Efavirenz, Elvucitabine, Emtricitabine, Fosamprenavir (Lexiva), Fozivudine tidoxil, GS 9137, GSK-873,140 (aplaviroc), GSK-364735, GW640385 (brecanavir), HG0004, HGTV43, INCB9471, KP-1461, Lopinavir, Mifepristone (VGX410), MK-0518, PPL-100, PRO 140, PRO 542, PRO 2000, Racivir, SCH-D (vicriviroc), SPO1A, SPL7013, TAK-652, Tipranavir (Aptivus), TNX-355, TMC125 (etravirine), UC-781, UK-427,857 (Maraviroc), Valproic acid, VRX496, Zalcitabine, Valganciclovir, Clindamycin with Primaquine, Fluconazole Pastille, Nystatin Pastille, Eflornithine, Pentamidine, Isethionate, Trimethoprim, Trimethoprim/sulfa, Piritrexim, Pentamidine isethionate, Spiramycin, Intraconazole-R51211, Trimetrexate, Daunorubicin, Recombinant Human Erythropoietin, Recombinant Human Growth Hormone, Megestrol Acetate, Testosterone, Aldesleukin (Proleukin), Amphotericin B, Azithromycin (Zithromax), Calcium hydroxyapatite, Doxorubicin, Dronabinol, Entecavir, Epoetin alfa, Etoposide, Fluconazole, Isoniazid, Itraconazole (Sporanox), Megestrol, Paclitaxel (Taxol), Peginterferon alfa-2, Poly-L-lactic acid (Sculptra), Rifabutin (Mycobutin), Rifampin, Somatropin and Sulfamethoxazole/Trimethoprim.

30. The composition according to claim 24 wherein said additional anti-HIV agent is selected from the group consisting of 3TC (Lamivudine), AZT (Zidovudine), (–)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), T20, fuseon and mixtures thereof.

31. The composition according to claim 9 in oral dosage form.

32. The composition according to claim 9 in parenteral dosage form.

33. The composition according to claim 9 in topical dosage form.

34. The composition according to claim 32 wherein said parenteral dosage form is an intravenous dosage form.

35. A method of treating an HIV infection in a patient in need thereof comprising administering to said patient an effective amount of a pharmaceutical composition according to claim 9.

36. A method of treating an HIV infection in a patient in need thereof comprising administering to said patient an effective amount of a pharmaceutical composition according to claim 10.

37. A method of treating an HIV infection in a patient in need thereof comprising administering to said patient an effective amount of a pharmaceutical composition according to claim 17.

38. A method of treating an HIV infection in a patient in need thereof comprising administering to said patient an effective amount of a pharmaceutical composition according to claim 18.

39. A method of treating an HIV infection in a patient in need thereof comprising administering to said patient an effective amount of a pharmaceutical composition according to claim 29.

40. A method of treating an HIV infection in a patient in need thereof comprising administering to said patient an effective amount of a pharmaceutical composition according to claim 30.

41. The method according to claim 35 wherein an active compound in said composition inhibits entry of HIV into a target cell by binding to a gp120 envelope protein thereof, and recruits antibodies to form a tertiary complex for attacking the bound HIV, leading to HIV and/or cell death.

42. The method according to claim 37 wherein an active compound in said composition inhibits entry of HIV into a target cell by binding to a gp120 envelope protein thereof, and recruits antibodies to form a tertiary complex for attacking the bound HIV, leading to HIV and/or cell death.

43. A method of reducing the likelihood of an HIV infection in a patient at risk for an HIV infection comprising administering to said patient an effective amount of a pharmaceutical composition according to claim 9.

44. The method according to claim 42 wherein said composition is topically administered to said patient in an area at risk for HIV infection.

45. A method of reducing the likelihood of AIDS or ARC in a patient infected with HIV comprising administering to said patient at risk for AIDS or ARC an effective amount of a composition according to claim 9.

46. A method of reducing or abolishing HIV infected CD cells in a patient comprising administering to an HIV infected patient an effective amount of a composition according to claim 9.

47. A method of inhibiting or abolishing HIV in a patient comprising administering to said patient an effective amount of a composition according to claim 9.

* * * * *

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: protease substrate

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:

```
<223> OTHER INFORMATION: protease substrate
<400> SEQUENCE: 2

Ala Leu Ala Leu
1
```